US 12,054,538 B2

(12) United States Patent
Diskin et al.

(10) Patent No.: US 12,054,538 B2
(45) Date of Patent: Aug. 6, 2024

(54) HIGHLY ACTIVE AGONISTIC CD4 BINDING SITE ANTI-HIV ANTIBODIES (HAADS) COMPRISING MODIFIED CDRH2 REGIONS THAT IMPROVE CONTACT WITH GP120

(71) Applicants: California Institute of Technology, Pasadena, CA (US); The Rockefeller University, New York, NY (US)

(72) Inventors: Ron Diskin, Rehovot (IL); Pamela J. Bjorkman, Altadena, CA (US); Michel Nussenzweig, New York, NY (US); Johannes Scheid, New York, NY (US)

(73) Assignees: California Institute of Technology, Pasadena, CA (US); The Rockefeller University, New York, NY (US)

( * ) Notice: Subject to any disclaimer, the term of this patent is extended or adjusted under 35 U.S.C. 154(b) by 0 days.

(21) Appl. No.: 18/046,481

(22) Filed: Oct. 13, 2022

(65) Prior Publication Data

US 2023/0192823 A1   Jun. 22, 2023

Related U.S. Application Data

(60) Division of application No. 16/786,821, filed on Feb. 10, 2020, now Pat. No. 11,472,868, which is a continuation of application No. 15/851,432, filed on Dec. 21, 2017, now Pat. No. 10,590,187, which is a continuation of application No. 13/558,312, filed on Jul. 25, 2012, now Pat. No. 9,890,207.

(60) Provisional application No. 61/523,244, filed on Aug. 12, 2011, provisional application No. 61/511,425, filed on Jul. 25, 2011.

(51) Int. Cl.
*C07K 16/10* (2006.01)

(52) U.S. Cl.
CPC ...... *C07K 16/1063* (2013.01); *C07K 2317/55* (2013.01); *C07K 2317/565* (2013.01); *C07K 2317/76* (2013.01); *C07K 2317/92* (2013.01); *C12N 2740/16111* (2013.01)

(58) Field of Classification Search
CPC .................................................. C07K 16/1063
See application file for complete search history.

(56) References Cited

U.S. PATENT DOCUMENTS

| 5,229,275 | A   | 7/1993  | Goroff |
|---|---|---|---|
| 5,545,806 | A   | 8/1996  | Lonberg et al. |
| 5,545,807 | A   | 8/1996  | Surani et al. |
| 5,567,610 | A   | 10/1996 | Borrebaeck et al. |
| 5,569,825 | A   | 10/1996 | Lonberg et al. |
| 5,591,669 | A   | 1/1997  | Krimpenfort et al. |
| 5,641,870 | A   | 6/1997  | Rinderknecht et al. |
| 9,493,549 | B2* | 11/2016 | Diskin ............... C07K 16/10 |
| 9,879,068 | B2* | 1/2018  | Diskin ............... C07K 16/1045 |
| 9,890,207 | B2  | 2/2018  | Diskin et al. |
| 10,590,187 | B2* | 3/2020  | Diskin ............... C07K 16/1063 |
| 11,149,081 | B2* | 10/2021 | Diskin ............... A61P 31/18 |
| 2009/0053220 | A1 | 2/2009  | Duensing et al. |
| 2014/0328862 | A1 | 11/2014 | Scheid et al. |

FOREIGN PATENT DOCUMENTS

| WO | 93/19786 A1   | 10/1993 |
|---|---|---|
| WO | 2012158948 A1 | 11/2012 |

OTHER PUBLICATIONS

Li, L., 2019, AbRSA: A robust tool for antibody numbering, Prot. Sci. 28:1524-1531.*
Abhinandan, K.R., et al.; "Analysis and improvements to Kabat and structurally correct numbering of antibody variable domains"; Molecular Immunology, 45; 2008; pp. 3832-3839.
Adams Paul D. et al.; "PHENIX: a comprehensive Python-based system for macromolecular structure solution"; Acta Crystallographica Section D; Biological Crystallography, D66; 2010; pp. 213-221.
Akers and Defilippis, 2000, Peptides and Proteins as Parenteral Solutions. In: Pharmaceutical Formulation Development of Peptides and Proteins. Philadelphia, PA: Taylor and Francis; pp. 149-192.
Akers, Michael J. et al.; "Formulation Development of Protein Dosage Forms"; Development and Manufacture of Protein Pharmaceuticals; 2002; Pharm. Biotechnol. 14; pp. 47-127.
Brüggemann, Marianne et al.; "Designer Mice: The Production of Human Antibody Repertoires in Transgenic Animals", Generation of Antibodies by Cell and Gene Immortalization; Year in Immuno.; 1993; vol. 7; pp. 33-40.
Casadevall, Arturo; "Antibodies for defense against biological attack"; Nature Biotechnology; vol. 20; Feb. 2002; p. 114.
Caskey et al., "Broadly neutralizing anti-HIV-1 monoclonal antibodies in the clinic", Nature Medicine, vol. 25, 2019, pp. 547-553.
Dashti et al., "Broadly Neutralizing Antibodies against HIV: Back to Blood", Trends in Molecular Medicine, vol. 25, No. 3, 2019.
Diskin, Ron et al.; "Increasing the Potency and Breadth of an HIV Antibody by Using Structure-Based Rational Design"; Science; vol. 334; Dec. 2, 2011; pp. 1289-1293.
Diskin, Ron et al.; "Structure of a clade C HIV-1 gp120 bound to CD4 and CD4-induced antibody reveals anti-CD4 polyreactivity"; Nature Structural & Molecular Biology; vol. 17; No. 5; May 2010; pp. 608-613.
Emsley, Paul et al.; "Coot: model-building tools for molecular graphics"; Research Papers; Acta Crystallographica Section D; Biological Crystallography; D60; 2004; pp. 2126-2132.

(Continued)

*Primary Examiner* — Jeffrey S Parkin
(74) *Attorney, Agent, or Firm* — Fox Rothschild LLP

(57) ABSTRACT

Embodiments of the present invention are directed to compositions and methods for anti-HIV (anti-CD4 binding site) potent VRC01-like (PVL) antibodies targeted to gp120 having an amino acid substitution at a residue in the anti-CD4 binding site PVL antibody that is equivalent to Phe43 in CD4, these antibodies having improved potency and breadth.

3 Claims, 33 Drawing Sheets
(22 of 33 Drawing Sheet(s) Filed in Color)
Specification includes a Sequence Listing.

(56) References Cited

OTHER PUBLICATIONS

Igarashi, Tatsuhiko et al.; "Human immunodeficiency virus type 1 newtralizing antibodies accelerate clearance of cell-free virions from blood plasma"; Nature Medicine; vol. 5, No. 2; Feb. 1999; pp. 211-216.
International Search Report and Written Opinion for corresponding PCT Application No. PCT/US2012/048209; mailed Feb. 28, 2013; 8 pp.
Jakobovits, Aya et al.; "Analysis of homozygous mutant chimeric mice: Deletion of the immunoglobulin heavy-chain joining region blocks B-cell development and antibody production"; Proc. Natl. Acad. Sci. USA; Genetics; vol. 90; Mar. 1993; pp. 2551-2555.
Jakobovits, Aya et al.; "Germ-line transmission and expression of a human-derived yeast artificial chromosome"; Letters to Nature; vol. 362; Mar. 18, 1993; pp. 255-258.
Jones, Peter T. et al.; "Replacing the complementarity-determining regions in a human antibody with those from a mouse"; Nature; vol. 321; May 29, 1986; pp. 522-525.
Kabsch, Wolfgang; "XDS"; Acta Crystallographica Section D; Biological Crystallography; D66; 2010; pp. 125-132.
Keller, Margaret A. et al.; "Passive Immunity in Prevention and Treatment of Infectious Diseases"; Clinical Microbiology Reviews; 2000; vol. 13; No. 4; pp. 602-614.
Klein, Joshua S. et al.; "Examination of the contributions of size and avidity to the neutralization mechanisms of the anti-HIV antibodies b12 and 4E10" PNAS; vol. 106; No. 18; May 5, 2009; pp. 7385-7390.
Kwong, Peter D. et al.; "Structure of an HIV gp120 envelope glycoprotein in complex with the CD4 receptor and a neutralizing human antibody"; Nature, vol. 393; Jun. 18, 1998; pp. 648-659.
Li, Yuxing et al.; "Mechanism of Neutralization by the Broadly Neutralizing HIV-1 Monoclonal Antibody VRCO"; Journal of Virology; vol. 85; No. 17; Sep. 2011; pp. 8954-8967.
Liu et al., "Broadly neutralizing antibodies for HIV-1: effecacies, challenges and opportunities", Emerging Microbes & Infections, 2020, vol. 9.
Madani, Navid et al.; "Small-Molecule CD4 Mimics Interact with a Highly Conserved Pocket on HIV-1 gp120"; Structure; 16(11); Nov. 12, 2008; pp. 1689-1701.
Mahomed et al., "Clinical Trials of Broadly Neutralizing Monoclonal Antibodies for Human Immunodeficiency Virus Prevention: A Review", The Journal of Infectious Diseases, 2021, 13;223(3), pp. 370-380.
McCoy, "The expanding array of HIV broadly neutralizing antibodies", Retrovirology, 2018, 15:70.
McGoff and Scher, 2000, Solution Formulation of Proteins/Peptides: In McNally, E.J., ed. Protein Formulation and Delivery. New York, NY: Marcel Dekker; pp. 139-158.
Montefiori, David C.; "Evaluating Neutralizing Antibodies Against HIV, SIV, and SHIV in Luciferase Reporter Gene Assays"; Basic Protocol 1; Detection and Analysis of HIV; Current Protocols in Immunology; Chapter 12; Unit 12.11; 2004; 17pp.
Parsons et al., "Importance of Fc-mediated functions of anti-HIV-1 broadly neutralizing antibodies", Retrovirology, 2018, 15:58.
Possas et al., "HIV cure: global overview of bNAbs' patents and related scientific publications", Expert Opinion on Therapeutic Patents, 2018, vol. 28, No. 7, pp. 551-560.
Reichmann, Lutz et al.; "Reshaping human antibodies for theraph"; Nature; vol. 332; Mar. 24, 1988; pp. 323-327.
Rudicell, R. et al. Enhanced Potency of a Broadly Neutralizing HIV-1 Antibody In Vitro Improves Protection against Lentiviral Infection In Vivo, Journal of Virology, vol. 88, No. 21, pp. 12669-12682 (2014).
Scharf, L., et al.; "Structural basis for HIV-1 gp120 recognition by a germ-line version of a broadly neutralizing antibody," Proc. Natl. Acad. Sci USA, 110(15), Apr. 2013, pp. 6049-6054.
Scheid, Johannes F. et al.; "Sequence and Structural Convergence of Broad and Potent HIV Antibodies That Mimic CD4 Binding"; Science; vol. 333; Sep. 16, 2011; pp. 1633-1637.
Shibata, Riri et al.; "Neutralizing antibody directed against the HIV-1 envelope glycoprotein can completely block HIV-1/SIV chimeric virus infections of macaque monkeys"; Nature Medicine; vol. 5; No. 2; Feb. 1999; pp. 204-210.
Sok et al., "Recent progress in broadly neutralizing antibodies to HIV", Nature Immunology, 2018, vol. 19, pp. 1179-1188.
Verhoeyen, Martine et al.; "Reshaping Human Antibodies: Grafting an Antilysozyme Activity"; Science; vol. 239; 1988; pp. 1534-1536.
Walker, Laura M. et al.; "Broad Neutralization coverage of HIV by multiple highly potent antibodies"; Nature; 2011; 6 pp.
West, Jr., Anthony P. et al.; "Structural basis for germ-line gene usage of a potent class of antibodies targeting the CD4-binding site of HIV-1 gp120"; PNAS; Jun. 27, 2011; pp. E2083-E2090.
Wu, X. et al. Rational Design of Envelope Identifies Broadly Neutralizing Human Monoclonal Antibodies to HIV-1, Science vol. 329, pp. 856-861 (2010).
Wu, Xueling et al.; "Focused Evolution of HIV-1 Neutralizing Antibodies Revealed by Structures and Deep Sequencing"; Science; vol. 333; Sep. 16, 2011; pp. 1593-1602.
Xiang J. et al., "Framework residues 71 and 93 of the chimeric B72.3 antibody are major determinants of the conformation of heavy-chain hypervariable loops," J. Mol. Biol., 1995, vol. 253, pp. 385-390.
Xiang, J et al., "Modification in framework region 1 results in a decreased affinity of chimeric anti-TAG72 antibody," Mol. Immunol., 1991, 28(1/2), pp. 141-148.
Zhou, T., et al., Aug. 2010, Structural basis for broad and potent neutralization of H IV-1 by antibody VRC01, Science 329:811-818.
Zhou, Tongqin et al.; "Structyural Basis for Broad and Potent Neutralization of HIV-1 by Antibody VRC01"; Science; vol. 329; Aug. 13, 2010; pp. 811-817.

\* cited by examiner

FIG. 2

Data collection and refinement statistics

|  | NIH45-46-93TH057 | Fab NIH45-46 |
|---|---|---|
| Data collection | | |
| Wavelength (Å) | 0.953 | 0.953 |
| Space group | $P2_12_12_1$ | $P2_12_12_1$ |
| Cell dimensions | | |
| a, b, c (Å) | 69.1, 70.5, 217.7 | 49.4, 87.4, 166.4 |
| α, β, γ (°) | 90.0, 90.0, 90.0 | 90.0, 90.0, 90.0 |
| Resolution (Å) | 37.05-2.45 (2.51-2.45) | 38.68-2.60 (2.67-2.60) |
| $R_{meas}$ (%) | 7.5 (66.9) | 12.2 (105.6) |
| $R_{mrgd-F}$ (%) | 11.6 (108.1) | 13.1 (78.0) |
| $I/\sigma I$ | 10.8 (1.8) | 12.83 (2.0) |
| Completeness (%) | 98.6 (98.7) | 99.5 (99.9) |
| Multiplicity | 3.7 | 6.6 |
| Reflections | 145342 | 150105 |
| Unique reflections | 39062 | 22795 |
| Refinement | | |
| Resolution (Å) | 37.05-2.45 | 38.68-2.6 |
| No. reflections | 38987 | 22692 |
| $R_{work}/R_{free}$ | 20.7 / 25.6 | 18.4 / 23.8 |
| No. atoms | | |
| Protein | 5989 | 3380 |
| Ligand/ion | 148 | 37 |
| Water | 67 | 125 |
| B-factors | | |
| Protein | 79.9 | 46.0 |
| Ligand/ion | 106.4 | 80.9 |
| Water | 62 | 42.0 |
| Ramachandran | | |
| Favored (%) | 96.12 | 96.49 |
| Allowed (%) | 3.48 | 3.28 |
| Outlier (%) | 0.40 | 0.23 |
| R.m.s. deviations | | |
| Bond lengths (Å) | 0.004 | 0.004 |
| Bond angles (°) | 0.754 | 0.838 |

5% of unique reflections were removed as a test set for the $R_{free}$ calculation.
Values in parentheses are for the highest resolution shell.

CD4-ZM135M.PL10a

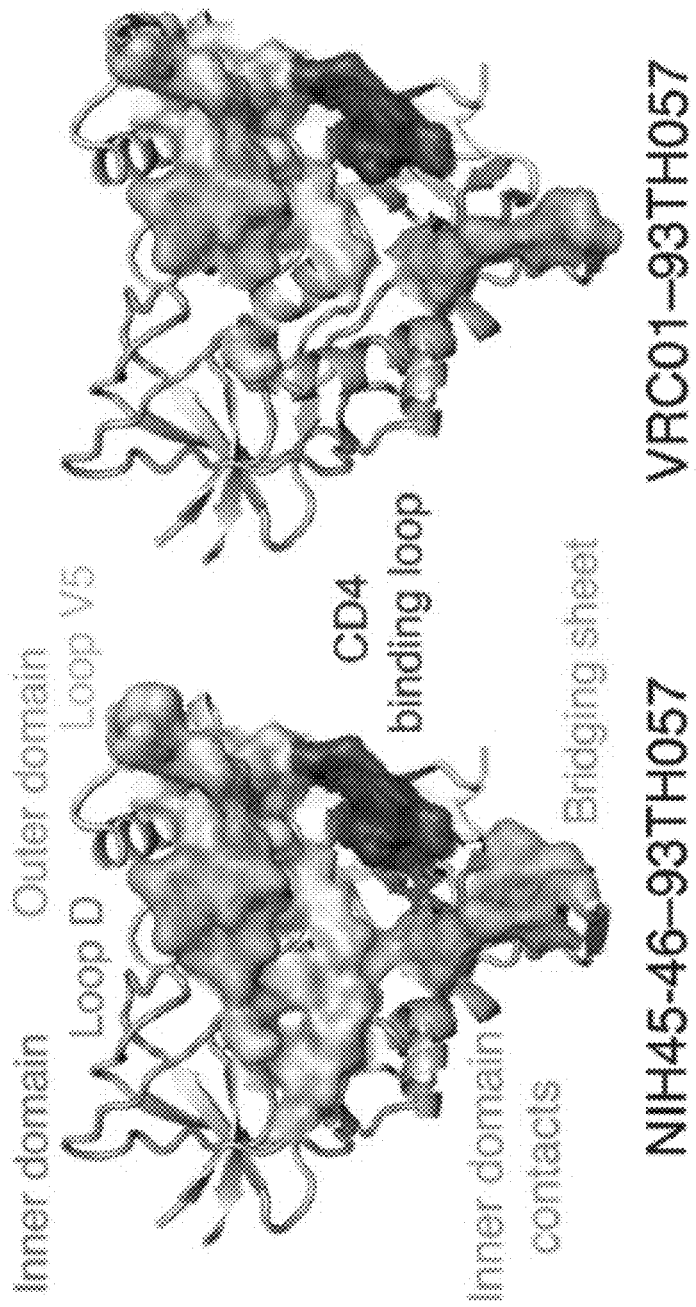

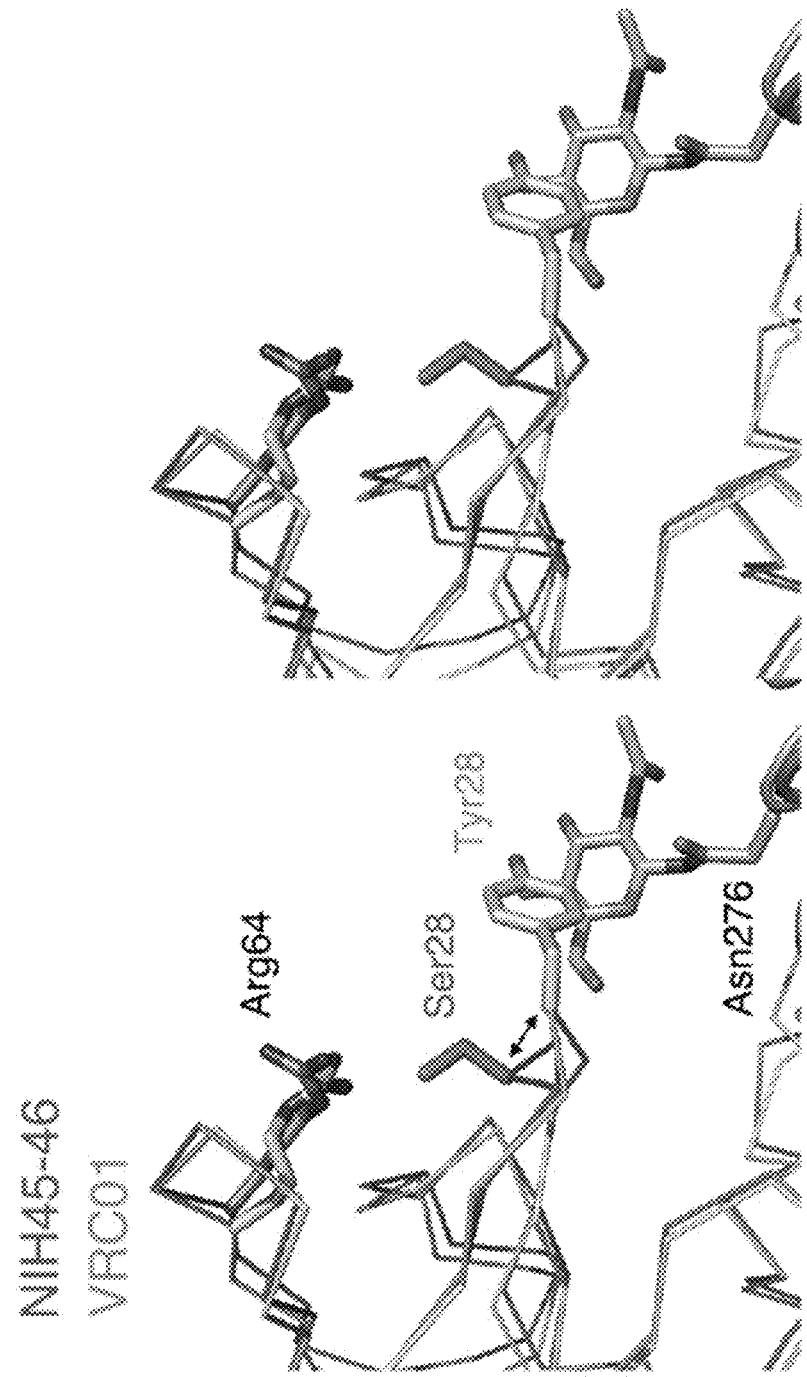

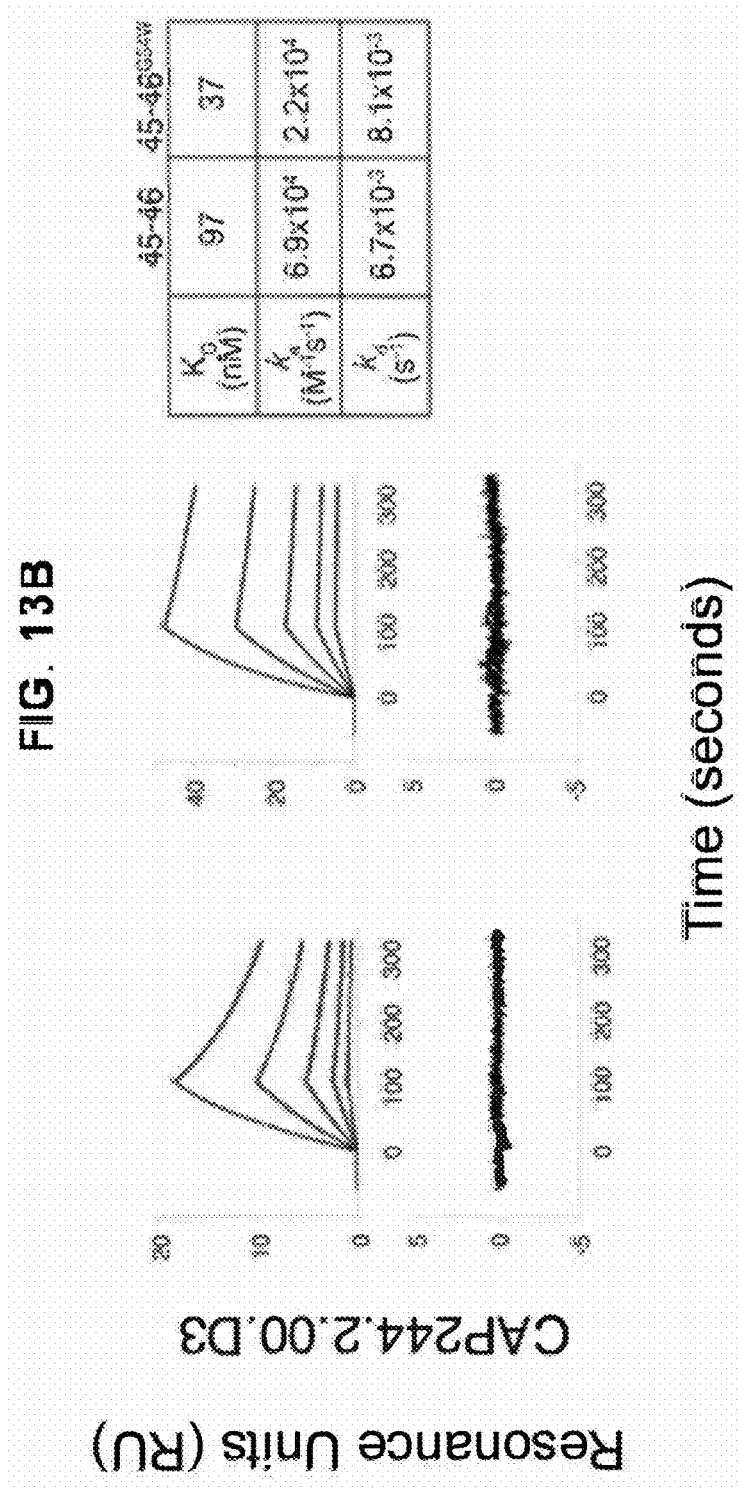

HIGHLY ACTIVE AGONISTIC CD4 BINDING SITE ANTI-HIV ANTIBODIES (HAADS) COMPRISING MODIFIED CDRH2 REGIONS THAT IMPROVE CONTACT WITH GP120

CROSS-REFERENCE TO RELATED APPLICATION(S)

The present application is a divisional application of U.S. patent application Ser. No. 16/786,821, filed Feb. 10, 2020, which is a continuation of U.S. patent application Ser. No. 15/851,432, filed Dec. 21, 2017, issued as U.S. Pat. No. 10,590,187 on Mar. 17, 2020, which is application is a continuation of U.S. patent application Ser. No. 13/558,312 filed on Jul. 25, 2012, issued as U.S. Pat. No. 9,890,207 on Feb. 13, 2018, which claims priority to and the benefit of U.S. Provisional Application Ser. No. 61/511,425 filed on Jul. 25, 2011, and U.S. Provisional Application Ser. No. 61/523,244 filed on Aug. 12, 2011, the entire contents of all of which are incorporated herein by reference.

STATEMENT REGARDING FEDERALLY SPONSORED RESEARCH OR DEVELOPMENT

This invention was made with government support under P01 AI081677-01, RR008862, and RR022220 awarded by the National Institutes of Health. The government has certain rights in the invention.

INCORPORATION BY REFERENCE

The present application is being filed along with a Sequence Listing in electronic format ST.26. The Sequence Listing is provided as a file entitled "070413_20710_Sequence_Listing 09_08_22_ST26, created Sep. 8, 2022 and is 93,100 bytes in size. The information in the electronic format of the Sequence Listing is incorporated herein by reference in its entirety.

TECHNICAL FIELD

This application is directed to a gp120 anti-CD4 binding site (anti-CD4bs) antibody composition that has improved potency and breadth against the human immunodeficiency virus, (HIV) which causes acquired immunodeficiency syndrome (AIDS).

TECHNICAL BACKGROUND

Three decades after the emergence of HIV there is still no vaccine, and AIDS remains a threat to global public health. However, some HIV-infected individuals eventually develop broadly neutralizing antibodies (bNAbs), i.e., antibodies that neutralize a large panel of HIV viruses and that can delay viral rebound in HIV patients. Such antibodies are relevant to vaccine development, as evidenced by the prevention of infection observed after passive transfer to macaques. Antibodies obtained by recent methods target several epitopes on the viral spike gp120 protein. These antibodies show broad and potent activity, and are referred to as highly active agonistic anti-CD4 binding site antibodies (HAADs). HAADS mimic binding of the host receptor CD4 protein by exposing the co-receptor binding site on gp120. Despite isolation from different donors, HAADs are derived from two closely-related Ig $V_H$ genes that share gp120 contact residues (Sheid et al., 2011, Science, 333:1633-1637 and Zhou et al., Science, 2010, 329: 811-817.)

Structural analysis of gp120 complexed with VRCO1 (a highly potent and broad HAAD), and gp120 complexed with each of VRC03 and VRC-PG04, (two new CD4bs antibodies sharing the VRC01 germline $V_H$ gene) revealed convergence of gp120 recognition despite low sequence identities (48-57% in $V_H$; 62-65% in $V_L$) (Wu et al, 2011, Science, 333:1593-1602). However, sequence differences between these clonally-unrelated anti-CD4 antibodies make it difficult to determine the structural features that yield neutralization potency and breadth to thereby obtain a potent HIV antibody that is effective across many HIV strains.

SUMMARY

In some embodiments of the present invention, an isolated anti-CD4 binding site (anti-CD4bs) potentVRC01-like (PVL) antibody composition having a heavy chain and a light chain includes a substituted hydrophobic amino acid in the heavy chain at a position equivalent to Phe43 of a CD4 receptor protein. In some embodiments, the position equivalent to Phe43 of the CD4 receptor protein is position 54 of the heavy chain. In some embodiments, the heavy chain of the anti-CD4bs PVL antibody is selected from SEQ ID NOs: 2, 4, 6, 8, 10, 12, 14, 16, 18, 20, 22, 24, 26, 28, 30, 32, 34, 36, 38, 40, 42, 44, 45, and/or 46. In some embodiments, the light chain of the anti-CD4bs PVL antibody is selected from SEQ ID NOs: 1, 3, 5, 7, 9, 11, 13, 15, 17, 19, 21, 23, 25, 27, 29, 31, 33, 35, 37, 39, 41, and/or 43.

In some embodiments of the present invention, the anti-CD4bs PVL antibody is VRC01, VRC02, NIH-45-46, 3BNC60, 3BNC117, 3BNC62, 3BNC95, 3BNC176, 12A21, VRC-PG04, VRC-CH30, VRC-CH31, VRC-CH32, VRC-CH33, VRC-CH34, VRC03 heavy chain with VRC01 light chain, gVRC-H5(d74) heavy chain with VRC-PG04 light chain, gVRC-H12(d74) heavy chain with VRC-PG04 light chain, VRC03, VRC01 heavy chain with VRC03 light chain, 3BNC55, 3BNC91, 3BNC104, 3BNC89, 12A21, or VRC-PG04b.

In some embodiments, the substituted hydrophobic amino acid is phenylalanine, tryptophan, or tyrosine.

In some embodiments of the present invention, the anti-CD4bs PVL antibody is NIH45-46, and the heavy chain position equivalent to Phe43 of the CD4 receptor protein is 54 of NIH-45-46.

In some embodiments of the present invention, a nucleic acid molecule encodes for the heavy chain and light chain of an anti-CD4bs PVL antibody having a substituted hydrophobic amino acid in the heavy chain at the position equivalent to Phe43 of the CD4 receptor protein. In some embodiments, a vector includes the nucleic acid molecule encoding the anti-CD4bs PVL antibody. In some embodiments, a cell includes the vector of the nucleic acid molecule encoding the anti-CD4bs PVL antibody.

In some embodiments of the present invention, a pharmaceutical composition includes the anti-CD4 bs PVL antibody composition or a fragment thereof and a pharmaceutically acceptable carrier.

In some embodiments of the present invention, a method of preventing or treating an HIV infection or an HIV-related disease includes identifying a patient having an HIV infection or an HIV-related disease, and administering to a patient a therapeutically effective amount of an anti-CD4bs PVL antibody as described.

In some embodiments of the present invention, a method of increasing the potency and breadth of an isolated anti-CD4 binding site (anti-CD4bs) potentVRC01-like (PVL) antibody composition having a heavy chain and a light chain includes substituting a target amino acid on the heavy chain with a substitute hydrophobic amino acid, where the target amino acid is at a position on the heavy chain equivalent to the Phe43 of a CD4 receptor protein.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

FIG. 2 is a table of the data and refinement statistics from the x-ray diffraction data collected from the NIH45-46 Fab crystal structure and the NIH45-46-gp120 (93TH057) complex as depicted in FIGS. 1A and 1B, according to embodiments of the present invention.

FIG. 9D is a structural depiction of a NIH45-46-gp120 (93TH057) complex with the contact interface labeled and colored as in FIG. 1B, and the corresponding Phe43$_{CD4}$ cavity as shown in FIG. 9B is indicated by the asterisk, according to embodiments of the present invention.

FIG. 9E is a structural depiction of a VRC01-gp120 (93TH057) complex with the contact interface labeled and colored as in FIG. 1B, according to embodiments of the present invention.

FIG. 11A is a stereo view of a structural depiction of a NIH45-46-gp120 complex superimposed with a VRC01-gp120 complex showing that Tyr28$_{VRC01\ LC}$ interacts with an N-linked carbohydrate attached to Asn276$_{gp120}$ and the side chain counterpart residue Ser28$_{NIH45-46}$ in the NIH45-46 complex faces away from gp120 to hydrogen bond with Arg64$_{NIH45-46\ LC}$ (the arrowheads point to Cα atoms of residue 28 in each structure), according to embodiments of the present invention.

FIG. 13B shows sensorgrams from surface plasmon resonance (SPR) experiments of binding experiments of the CAP244.2.00 D3 gp120 protein with NIH45-46 and NIH45-46$^{G54W}$ Fabs, as indicated, and a table of the K$_D$ values is shown, according to embodiments of the present invention.

FIG. 18A shows an alignment of the heavy chains of PVL antibodies, their less potent relatives, and their germ-line precursor (SEQ ID NOs. 2, 6, 8, 10, 12, 14, 16, 18, 20, 22, 24, 26, 28, 30, 32, 34, 36, 38, 40, 45, 46, and 47-59), according to embodiments of the present invention.

FIG. 18B shows an alignment of the light chains of PVL antibodies, their less potent relatives, and their germ-line precursors (SEQ ID NOs. 1, 5, 7, 9, 11, 13, 15, 17, 19, 21, 23, 25, 27, 29, 31, 33, 35, 37, 39, and 60-73), according to embodiments of the present invention.

DETAILED DESCRIPTION

Figure 1A:
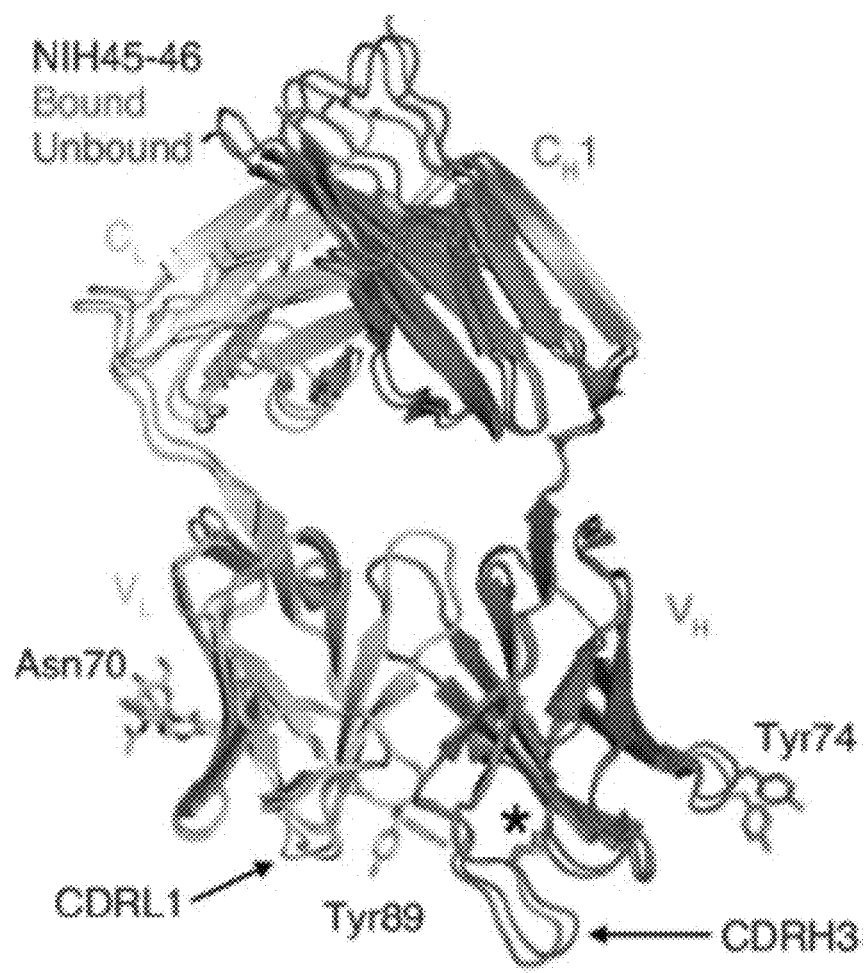
FIG. 1A is a superimposition of a structural depiction of NIH45-46 Fab alone (in blue) and of NIH45-46-gp120 complex (in magenta), according to embodiments of the present invention.

Aspects of the present invention are directed to anti-CD4 binding site (CD4bs) antibodies. Embodiments of the present invention include anti-CD4bs antibodies which are potent VRC01-like (PVL) antibodies as defined herein. In some embodiments of the present invention, an anti-CD4bs PVL antibody has a substituted hydrophobic amino acid residue at a position that is equivalent to phenylalanine at position 43 (Phe43) of the host CD4 receptor protein (CD4). In some embodiments of the present invention, a method for increasing the potency and breadth of a PVL antibody includes identifying a target amino acid at the position on the heavy chain of the PVL antibody that is equivalent to Phe43 on CD4, and substituting the target amino acid with a hydrophobic amino acid. For example, in the PVL antibody, NIH45-46, glycine at position 54 (Gly54) is in the Phe43-equivalent position, and substitution of Gly54 in NIH45-46 (Gly54$^{NM45-46}$) with a hydrophobic amino acid such as tryptophan, results in NIH45-46$^{G54W}$ which has increased potency and breadth compared to NIH45-46.

Abbreviations for amino acids are used throughout this disclosure and follow the standard nomenclature known in the art. For example, as would be understood by those of ordinary skill in the art, Alanine is Ala or A; Arginine is Arg or R; Asparagine is Asn or N; Aspartic Acid is Asp or D; Cysteine is Cys or C; Glutamic acid is Glu or E; Glutamine is Gln or Q; Glycine is Gly or G; Histidine is His or H; Isoleucine is Ile or I; Leucine is Leu or L; Lysine is Lys or K; Methionine is Met or M; Phenylalanine is Phe or F; Proline is Pro or P; Serine is Ser or S; Threonine is Thr or T; Tryptophan is Trp or W; Tyrosine is Tyr or Y; and Valine is Val or V.

Hydrophobic amino acids are well known in the art. Hydrophobic amino acids include alanine, isoleucine, leucine, methionine, phenylalanine, tryptophan, tyrosine, and valine. In some embodiments of the present invention, an anti-CD4bs PVL antibody has a hydrophobic amino acid substituted at a position equivalent to Phe43 of the CD4 receptor protein, wherein the hydrophobic amino acid is alanine, isoleucine, leucine, methionine, phenylalanine, tryptophan, tyrosine, or valine. In other embodiments, an anti-CD4bs PVL antibody has a hydrophobic amino acid substituted at the position equivalent to Phe43 of CD4 receptor protein, wherein the hydrophobic amino acid is tryptophan, phenylalanine, or tyrosine.

Throughout this disclosure and in embodiments of the present invention, the term "antibody" (Ab) as used herein includes monoclonal antibodies, polyclonal antibodies, multispecific antibodies (for example, bispecific antibodies and polyreactive antibodies), and antibody fragments. Thus, the term "antibody" and "isolated antibody" are used interchangeably herein to refer to an isolated antibody according to embodiments of the present invention. An antibody in any context within this specification is meant to include, but is not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from the NH2 terminus to the COOH terminus as follows: FWR1, CDR1, FWR2, CDR2, FWR3, CDR3, FWR4. The variable regions of the heavy and light chains contain a binding domain that interacts with an antigen while, depending on the isotype, the constant region(s) may mediate the binding of the immunoglobulin to host tissues or factors. CDR1, CDR2, and CDR3 of the light chain are referred to as CDRL1, CDRL2 and CDRL3, respectively. CDR1, CDR2, CDR3 of the heavy chain are referred to as CDRH1, CDRH2, and CDRH3, respectively.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan. The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in close proximity by the FRs and, with the hypervariable regions from the other chain, contribute to the formation of the antigen-binding site of antibodies. The term "hypervariable region" as used herein refers to the amino acid residues of an antibody that are responsible for antigen binding. The hypervariable region generally comprises amino acid residues from a "complementarity determining region" ("CDR").

An antibody of the present invention may be a "humanized antibody". A humanized antibody is considered to be a human antibody that has one or more amino acid residues introduced into it from a source that is non-human. These non-human amino acid residues often are referred to as "import" residues, which typically are taken from an "import" variable region. Humanization may be performed following known methods by substituting import hypervariable region sequences for the corresponding sequences of a human antibody. (See, for example, Jones et al., Nature, 321:522-525 20 (1986); Reichmann et al., Nature, 332:323-327 (1988); Verhoeyen et al., Science, 239:1534-1536 (1988)) the entire contents of each are incorporate herein by reference). Accordingly, such "humanized" antibodies are chimeric antibodies in which substantially less than an intact human variable region has been substituted by the corresponding sequence from a non-human species.

An antibody of the present invention includes an "antibody fragment" which includes a portion of an intact antibody, such as the antigen binding or variable region of the intact antibody. Examples of antibody fragments include, but are not limited to, Fab, Fab', F(ab')2, and Fv fragments; diabodies; linear antibodies; single-chain antibody molecules; and multispecific antibodies formed from antibody fragments. (See, for example, U.S. Pat. No. 5,641,870, the entire content of which is incorporated herein by reference.)

Throughout this disclosure and in embodiments of the present invention, a "potent VRC01-like" ("PVL") antibody of the present invention is an anti-CD4 binding site antibody that has the following conserved heavy chain (HC) and light chain (LC) residues: $Arg71_{HC}$, $Trp50_{HC}$, $Asn58_{HC}$, $Trp100B_{HC}$, $Glu96_{LC}$, $Trp67_{LC}/Phe67_{LC}$, as well as exactly 5 amino acids in CDRL3 domain (using Kabat numbering). (The Kabat numbering system is described in Abhinandan, K. R. and Martin, A. C. R. (2008), "Analysis and improvements to Kabat and structurally correct numbering of antibody variable domains," *Molecular Immunology*, 45: 3832-3839, the entire contents of which are herein incorporated by reference.) A PVL antibody of the present invention is any antibody as defined herein, that has the listed PVL features irrespective of the synthesis or derivation of the antibody, irrespective of the other unrestricted domains of the antibody, and irrespective of whether or not other domains of the antibody are present, so long as the antibody has the signature residues and features.

Throughout the disclosure and in embodiments of the present invention, the terms "Phe43-equivalent position" and "$Phe43_{CD4}$ equivalent position" are used interchangeably and refer to an amino acid position within the heavy chain of a PVL antibody that replicates or mimics the binding pocket and interface contributed by Phe43 of the host CD4 receptor when the CD4 receptor protein is complexed with the HIV viral spike protein gp120. As known in the art, assigned amino acid positions of an antibody do not necessarily correspond to the amino acid residue as numbered from the amino-terminus. Following the Kabat antibody residue/position numbering system, the amino acid residue number may be the same as the amino acid position, but is not necessarily so. (See, Abhinandan, K. R. and Martin, A. C. R. (2008) *Molecular Immunology,* 45: 3832-3839.) The structure of the antibody peptide determines the position number. The information for determining position number using the Kabat system for each amino acid in a given sequence can be determined using the information found in Abhinandan and Martin, 2008. Using this position numbering system, the Phe43-equivalent position in a PVL antibody heavy chain sequence can be determined, and substituted with a hydrophobic amino acid to create a similar binding pocket as conferred by Phe43 in CD4. Methods for this mutagenesis are well known in the art (e.g. Example 2).

Subsequent heavy chain sequences can be analyzed using the Kabat numbering system to determine the equivalent position to this position 54. Alternatively, the Phe43CD4-equivalent position can also be determined by structural analysis such as x-ray crystallography. Any means of determining the $Phe43_{CD4}$-equivalent position may be used so long as the Kabat system is followed as applicable.

For example, the Phe43-equivalent position in NIH45-46 is position 54 as determined by x-ray crystallography and shown herein. The native NIH45-46 sequence contains a glycine at position 54 (Gly54). As such, a PVL antibody substituted with a hydrophobic amino acid at this Phe-43 equivalent position mimics the desired contact interface between the CD4 receptor protein and the CD4 binding site of gp120 (see, e.g., Example 2).

In some embodiments of the present invention, position 54 (Kabat numbering) of the heavy chain of a PVL antibody has a substituted hydrophobic amino acid. Position 54 is determined by analyzing a heavy chain amino acid sequence of a PVL antibody using the Kabat numbering system.

In some embodiments of the present invention, a hydrophobic amino acid is substituted for the "native" amino acid present at the $Phe43_{CD4}$-equivalent position on the heavy chain of a PVL antibody, where a PVL antibody is an antibody as defined herein having the PVL signature features as described herein, and "native" refers to the amino acid that is present in the PVL antibody prior to substitution. The native amino acid may also be hydrophobic, and may be substituted with another hydrophobic amino acid.

In some embodiments of the present invention, non-limiting examples of PVL antibodies include VRC01, VRC02, NIH-45-46, 3BNC60, 3BNC117, 3BNC62, 3BNC95, 3BNC176, 12A21, VRC-PG04, VRC-CH30, VRC-CH31, VRC-CH32, VRC-CH33, VRC-CH34, VRC03 heavy chain (HC) with VRC01 light chain (LC), gVRC-H5 (d74)/VRC-$PG04_{LC}$, and gVRC-H12(d74)/VRC-$PG04_{LC}$, VRC03, VRC01 heavy chain (HC) with VRC03 light chain (LC), 3BNC55, 3BNC91, 3BNC104, 3BNC89, 12A21, and VRC-PG04b as listed below in Table 1.

TABLE 1

Examples of PVL Antibodies

| Antibody Name | Light Chain SEQ ID NO: | Heavy Chain SEQ ID NO: |
|---|---|---|
| VRC01 | 1 | 2 |
| VRC02 | 3 | 4 |
| NIH-45-46 | 5 | 6 |
| 3BNC60 | 7 | 8 |
| 3BNC117 | 9 | 10 |
| 3BNC62 | 11 | 12 |
| 3BNC95 | 13 | 14 |
| 3BNC176 | 15 | 16 |
| 12A12 | 17 | 18 |
| VRC-PG04 | 19 | 20 |
| VRC-CH30 | 21 | 22 |
| VRC-CH31 | 23 | 24 |
| VRC-CH32 | 25 | 26 |
| VRC-CH33 | 27 | 28 |
| VRC-CH34 | 29 | 30 |
| VRC03 | 31 | 32 |
| 3BNC55 | 33 | 34 |
| 3BNC91 | 35 | 36 |
| 3BNC104 | 37 | 38 |
| 3BNC89 | 39 | 40 |
| 12A21 | 41 | 42 |
| VRC-PG04b | 43 | 44 |
| VRC03HC-VRC01LC | 1 | 32 |
| VRC01HC/VRC03LC | 31 | 2 |
| gVRC-H5(d74)/ VRC-PG04LC | 19 | 45 |
| gVRC0H12(D74)/ VRC-PG04LC | 19 | 46 |

In some embodiments of the present invention, a PVL antibody has a heavy chain selected from one of the heavy chains listed above in Table 1 (SEQ ID NOs 2, 4, 6, 8, 10, 12, 14, 16, 18, 20, 22, 24, 26, 28, 30, 32, 34, 36, 38, 40, 42, 44, 45, and 46). Any PVL heavy chain may be matched with a PVL light chain so long as the signature PVL residue features are maintained. In some embodiments, any one of the PVL heavy chains of Table 1 is expressed with any one of the PVL light chains of SEQ ID NOs 1, 3, 5, 7, 9, 11, 13, 15, 17, 19, 21, 23, 25, 27, 29, 31, 33, 35, 37, 39, 41, and 43. In other embodiments, any PVL antibody heavy chain can be combined with any PVL antibody light chain.

In embodiments of the present invention, the terms "nucleic acid" and "polynucleotide" are used interchangeably herein to refer to single-stranded or double-stranded RNA, DNA, or mixed polymers. Polynucleotides can include genomic sequences, extra-genomic and plasmid sequences, and smaller engineered gene segments that express, or can be adapted to express polypeptides.

An "isolated nucleic acid" is a nucleic acid that is substantially separated from other genome DNA sequences as well as proteins or complexes such as ribosomes and polymerases, which naturally accompany a native sequence.

In some embodiments of the present invention, nucleic acid molecules encode part or all of the light and heavy chains of the described inventive antibodies, and fragments thereof. Due to redundancy of the genetic code, variants of these sequences will exist that encode the same amino acid sequences.

The present invention also includes isolated nucleic acid molecules encoding the polypeptides of the heavy and the light chain of the PVL antibodies listed in Table 1. In some embodiments, an isolated nucleic acid molecule encodes for any of the PVL heavy chain and light chain polypeptides including those of SEQ ID NOs 2, 4, 6, 8, 10, 12, 14, 16, 18, 20, 22, 24, 26, 28, 30, 32, 34, 36, 38, 40, 42, 44, 45, and 46, and SEQ ID NOs 1, 3, 5, 7, 9, 11, 13, 15, 17, 19, 21, 23, 25, 27, 29, 31, 33, 35, 37, 39, 41, and 43, respectively, in which the $Phe43_{CD4}$-equivalent amino acid (i.e., the target amino acid) of the heavy chain is substituted with a hydrophobic amino acid.

Embodiments of the present invention also include vectors and host cells including a nucleic acid encoding a PVL antibody of the present invention, as well as recombinant techniques for the production of polypeptide of the invention. Vectors of the invention include those capable of replication in any type of cell or organism, including, for example, plasmids, phage, cosmids, and mini chromosomes. In some embodiments, vectors comprising a polynucleotide 5 of the described invention are vectors suitable for propagation or replication of the polynucleotide, or vectors suitable for expressing a polypeptide of the described invention. Such vectors are known in the art and commercially available.

In embodiments of the present invention, "vector" includes shuttle and expression vectors. Typically, the plasmid construct will include an origin of replication (for example, the ColE1 origin of replication) and a selectable marker (for example, ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells.

In some embodiments of the present invention, in order to express a polypeptide of the invention, the nucleotide sequences encoding the polypeptide, or functional equivalents, may be inserted into an appropriate expression vector, i.e., a vector that contains the necessary elements for the transcription and translation of the inserted coding sequence. Methods well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (2001) Molecular Cloning, A Laboratory Manual, Cold Spring Harbor Press, Plainview, N.Y., the entire contents of which are incorporated herein by reference.

As used herein, the term "cell" can be any cell, including, but not limited to, eukaryotic cells, such as, but not limited to, mammalian cells or human cells.

In some embodiments of the present invention, the antibodies disclosed herein are produced recombinantly using vectors and methods available in the art. (see, e.g. Sambrook et al., 2001, supra). Human antibodies also can be generated by in vitro activated B cells (see, for example, U.S. Pat. Nos. 5,567,610 and 5,229,275). Reagents, cloning vectors, and kits for genetic manipulation are available from commercial vendors such as BioRad, Stratagene, Invitrogen, ClonTech and Sigma-Aldrich Co.

In some embodiments of the present invention, human antibodies are produced in transgenic animals (for example, mice) that are capable of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germline mutant mice results in the production of human antibodies upon antigen challenge. See, for example, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669; 5,545,807; and WO 97/17852, the entire contents of all of which are incorporated herein by reference. Such animals can be genetically engineered to produce human antibodies comprising a polypeptide of a PVL antibody of the present invention.

In some embodiments of the present invention, a method includes the preparation and administration of an HIV antibody composition (e.g., a PVL antibody having a hydrophobic amino acid substituted at the $Phe43_{CD4}$-equivalent position of the PVL heavy chain) that is suitable for administration to a human or non-human primate patient having an HIV infection, or at risk of HIV infection, in an amount and according to a schedule sufficient to induce a protective immune response against HIV, or reduction of the HIV virus, in a human.

In some embodiments of the present invention, a vaccine includes at least one antibody as disclosed herein and a pharmaceutically acceptable carrier. In some embodiments of the present invention, the vaccine is a vaccine including at least one PVL antibody as described herein and a pharmaceutically acceptable carrier. The vaccine can include a plurality of the antibodies having the characteristics described herein in any combination and can further include HIV neutralizing antibodies such as a PVL antibody having the $Phe43_{CD4}$-equivalent residue on the heavy chain substituted with a hydrophobic amino acid.

In some embodiments of the present invention, carriers as used herein include pharmaceutically acceptable carriers, excipients or stabilizers that are nontoxic to the cell or mammal being exposed thereto at the dosages and concentrations employed. Often the physiologically acceptable carrier is an aqueous pH buffered solution. Examples of physiologically acceptable carriers include, but are not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to: polyvinylpyrrolidone; amino acids such as, but not limited to: glycine, glutamine, asparagine, arginine or lysine; monosaccharides, disaccharides, and other carbohydrates including, but not limited to: glucose, mannose, or dextrins; chelating agents such as, but not limited to: EDTA (ethylenediaminetetraacetic acid); sugar alcohols such as, but not limited to: mannitol or sorbitol; salt-forming counterions such as, but not limited to: sodium; and/or nonionic surfactants such as, but not limited to TWEEN® (polysorbate); polyethylene glycol (PEG), and PLURONICS® (poloxamers).

In some embodiments of the present invention, the compositions may include a single antibody or a combination of antibodies, which can be the same or different, in order to prophylactically or therapeutically treat the progression of various subtypes of HIV infection after vaccination. Such combinations can be selected according to the desired immunity. When an antibody is administered to an animal or a human, it can be combined with one or more pharmaceutically acceptable carriers, excipients or adjuvants as are known to one of ordinary skilled in the art. The composition can further include broadly neutralizing antibodies known in the art, including, for example, a PVL antibody having the $Phe43_{CD4}$-equivalent residue substituted with a hydrophobic amino acid.

In some embodiments of the present invention, an antibody-based pharmaceutical composition includes a therapeutically effective amount of an isolated HIV antibody which provides a prophylactic or therapeutic treatment choice to reduce infection of the HIV virus. The antibody-based pharmaceutical composition of the present invention may be formulated by any number of strategies known in the art (e.g., see McGoff and Scher, 2000, Solution Formulation of Proteins/Peptides: In McNally, E. J., ed. Protein Formulation and Delivery. New York, N.Y.: Marcel Dekker; pp. 139-158; Akers and Defilippis, 2000, Peptides and Proteins as Parenteral Solutions. In: Pharmaceutical Formulation Development of Peptides and Proteins. Philadelphia, Pa.: Taylor and Francis; pp. 145-177; Akers, et 5 al., 2002, Pharm. Biotechnol. 14:47-127, the entire contents of all of which are incorporated herein by reference).

In some embodiments of the present invention, a method for treating a mammal infected with a virus infection, such as, for example, HIV, comprising administering to said mammal a pharmaceutical composition comprising an HIV antibody composition as disclosed herein. According to some embodiments, the method for treating a mammal infected with HIV includes administering to said mammal a pharmaceutical composition that includes an antibody as disclosed herein, or a fragment thereof. The compositions of embodiments of the present invention may include more than one antibody having the characteristics disclosed herein. For example, a plurality or pool of PVL antibodies, each antibody having the $Phe43_{CD4}$-equivalent residue substituted with a hydrophobic amino acid.

In some embodiments of the present invention, in vivo treatment of human and non-human patients includes administering or providing a pharmaceutical formulation including an HIV antibody according to embodiments of the present invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies can be administered parenterally, when possible, at the target cell site, or intravenously. In some embodiments, a PVL antibody composition as described herein is administered by intravenous or subcutaneous administration.

In some embodiments of the present invention, a therapeutically effective amount of an antibody is administered to a patient. In some embodiments, the amount of antibody administered is in the range of about 0.1 mg/kg to about 50 mg/kg of patient body weight. Depending on the type and severity of the infection, about 0.1 mg/kg to about 50 mg/kg body weight (for example, about 0.1-15 mg/kg/dose) of antibody is an 5 initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

In some embodiments of the present invention, passive immunization using a PVL antibody as disclosed herein, is used as an effective and safe strategy for the prevention and treatment of HIV disease. (See, for example, Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference).

The following Examples are presented for illustrative purposes only, and do not limit the scope or content of the present application.

Examples

Figure 18A:
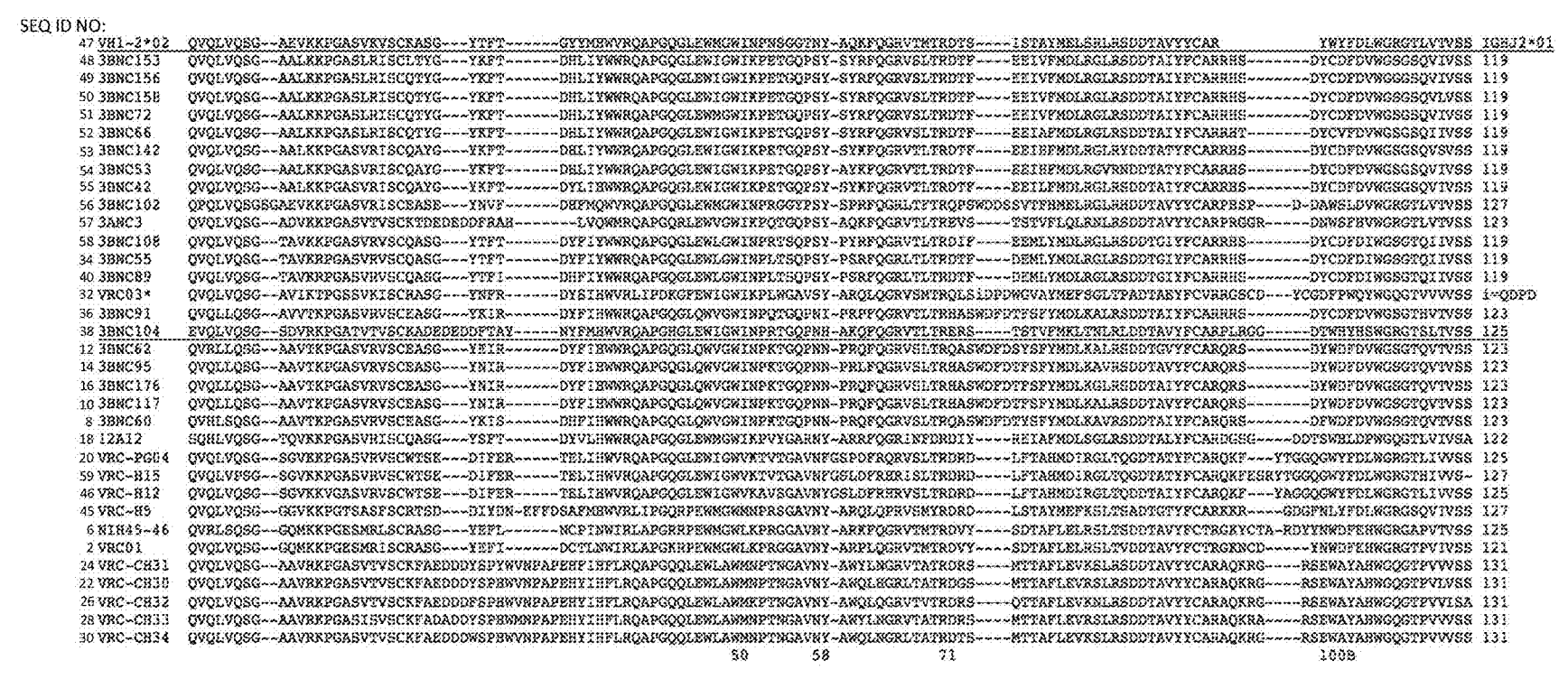
Figure 18B:
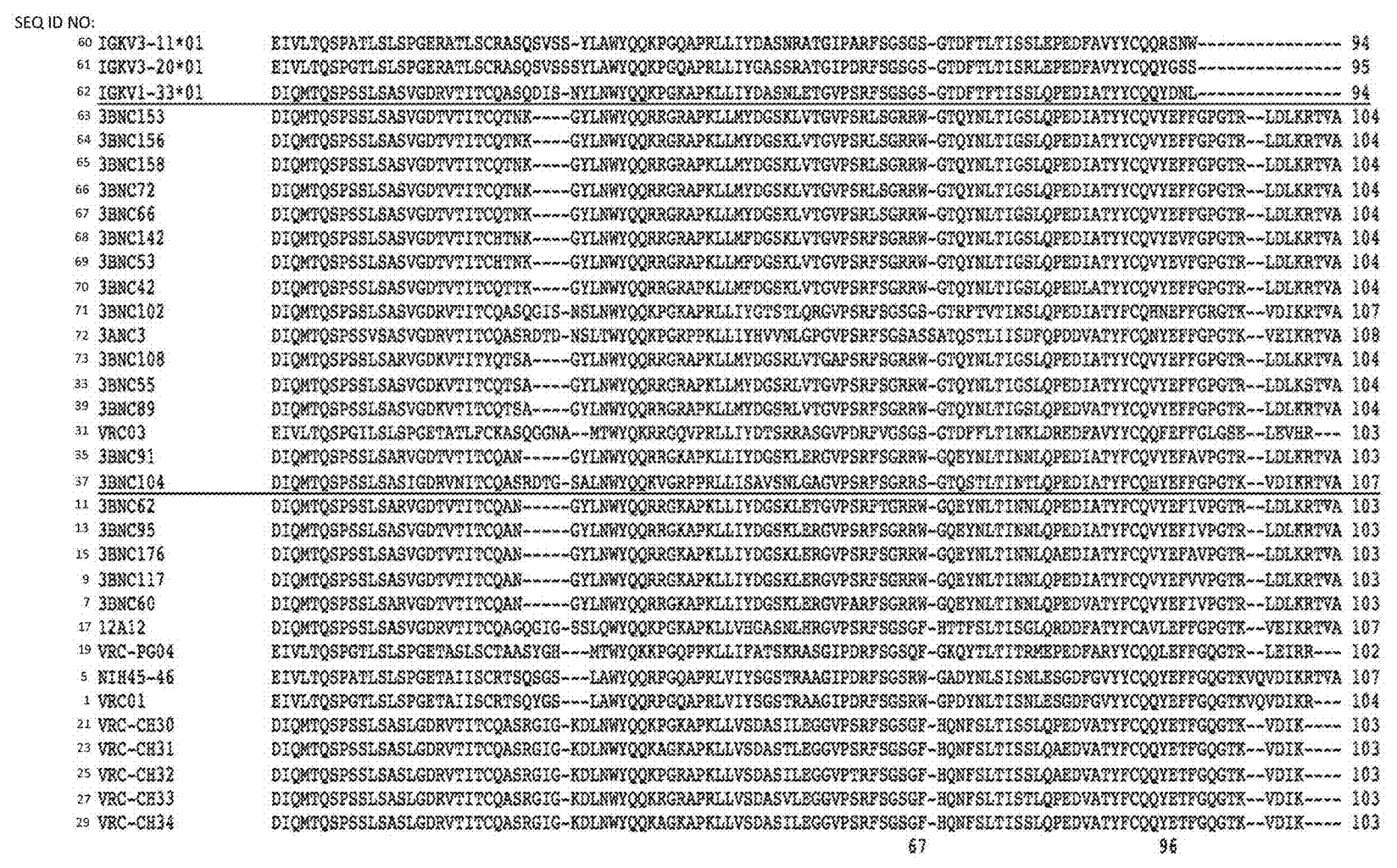

Reference is made to Diskin et al. 2013, JEM, 210: 1235-1249; Diskin et al., 2011, Science, 334:12989-1293; and West et al., 2012, PNAS, (doi: 10.1073/pnas.1208984109), the entire contents of all of which are incorporated herein by reference. FIGS. 18A and 18B show the heavy chain (SEQ ID NOs. 2, 6, 8, 10, 12, 14, 16, 18, 20, 22, 24, 26, 28, 30, 32, 34, 36, 38, 40, 45, 46, and 47-59) and light chain (SEQ ID NOs. 1, 5, 7, 9, 11, 13, 15, 17, 19, 21, 23, 25, 27, 29, 31, 33, 35, 37, 39, and 60-73) amino acid sequence alignments of several related variant groups of PVL antibodies as presented in FIG. 2 of West et al. with CDRs defined using the Chothia definition of the Abysis database.

Figure 1B:
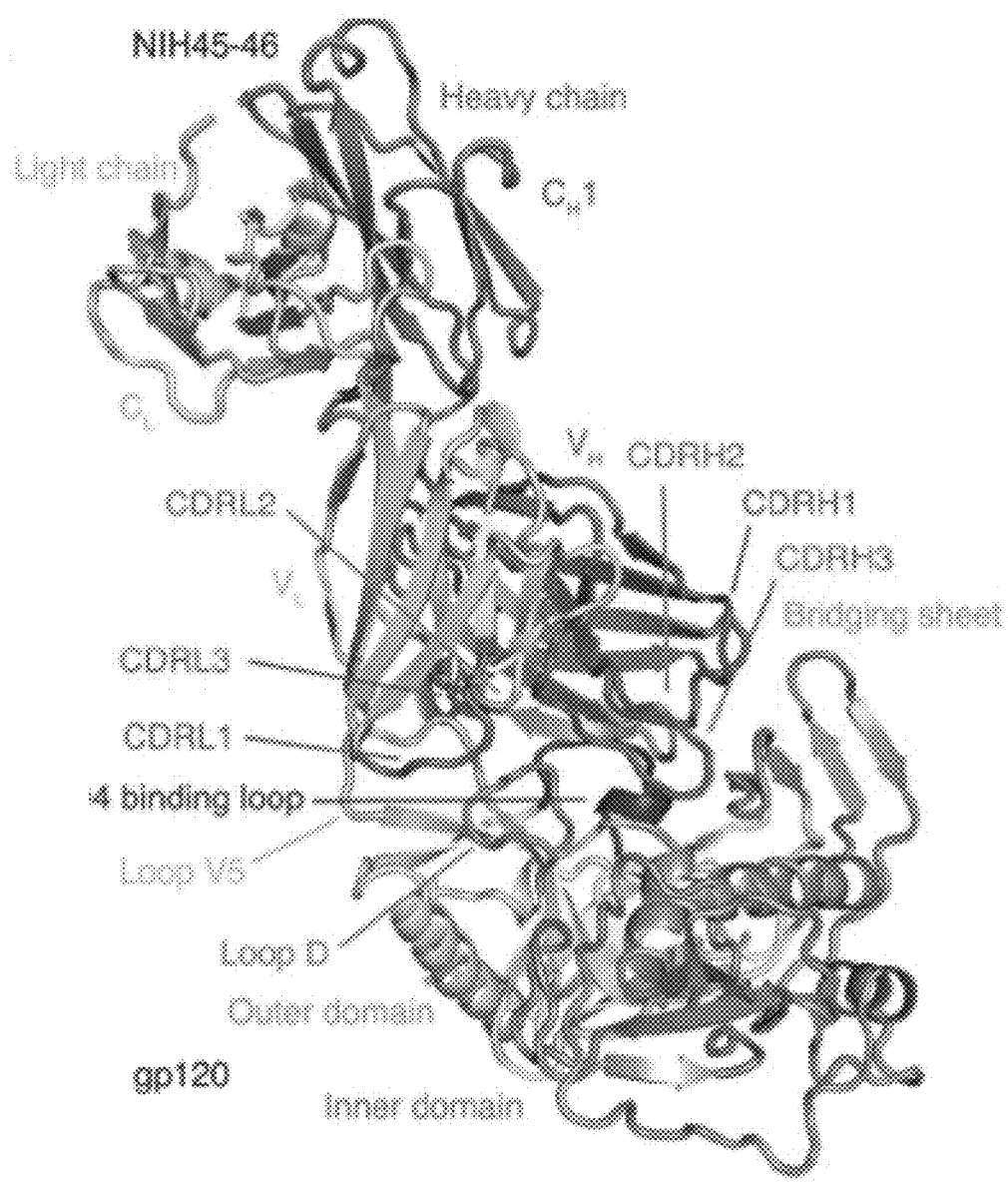
FIG. 1B is a structural depiction of NIH45-46-gp120 (93TH053) complex and the binding interface and domains labeled and colored as indicated, with NIH45-46 Fab shown in magenta (heavy chain) and light purple (light chain), and gp120 shown in yellow (inner domain) and grey (outer domain), according to embodiments of the present invention.
Figure 3A:
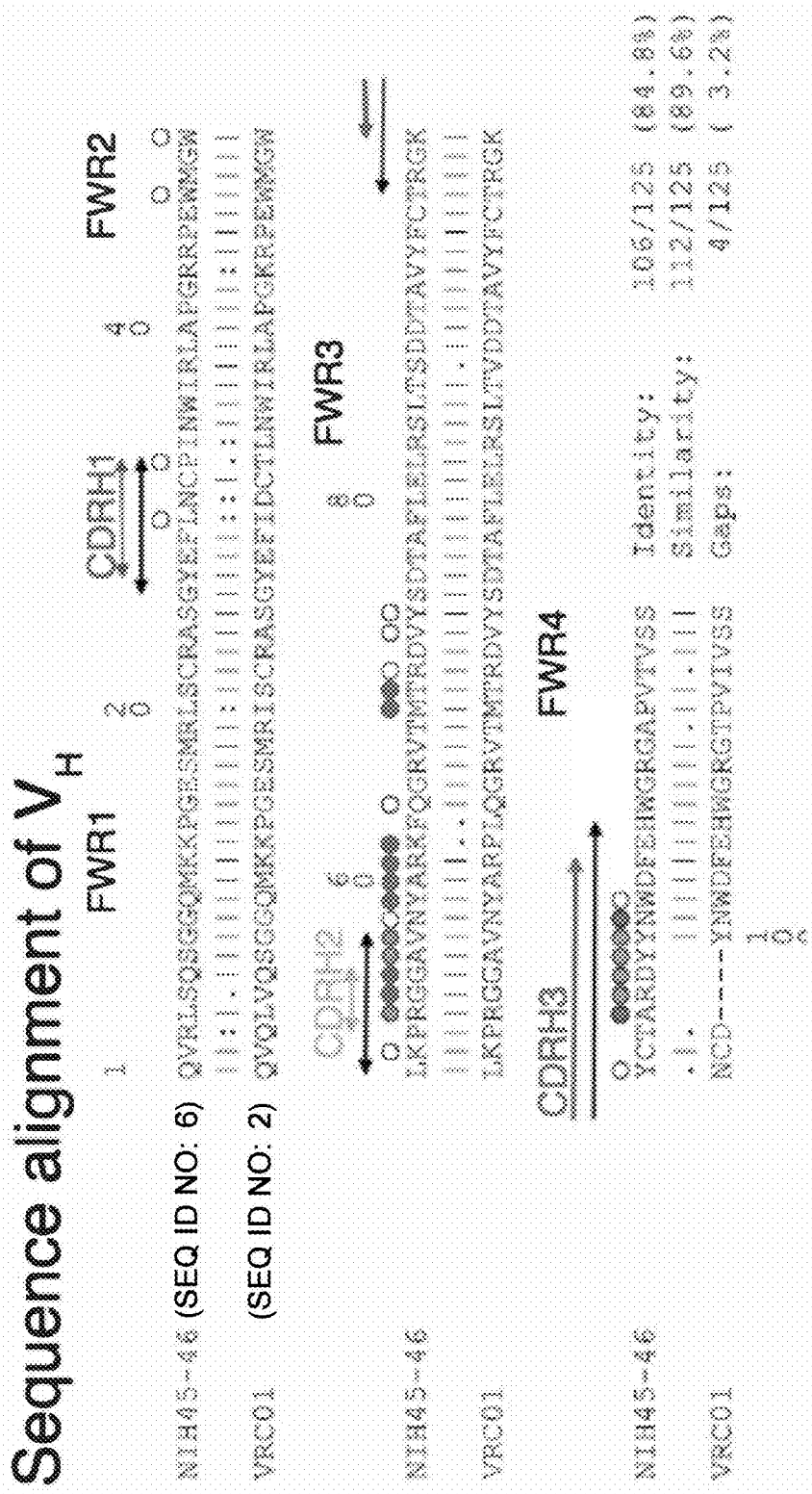
FIG. 3A is a sequence alignment of the heavy chain variable ($V_H$) domains of NIH45-46 (SEQ ID NO: 6) and VRC01 (SEQ ID NO: 2) antibodies, in which the open circles indicate NIH45-46 side chain residues that contact gp120 and closed circles indicate NIH45-46 main-chain, or main-chain and side chain residues that contact gp120, according to embodiments of the present invention.
Figure 3B:
FIG. 3B is a sequence alignment of the light chain variable ($V_L$) domains of NIH45-46 (SEQ ID NO: 5) and VRC01 (SEQ ID NO: 1) antibodies, in which the open circles indicate NIH45-46 side chain residues that contact gp120 and closed circles indicate NIH45-46 main-chain, or main-chain and side chain residues that contact gp120, according to embodiments of the present invention.
Figure 4A:
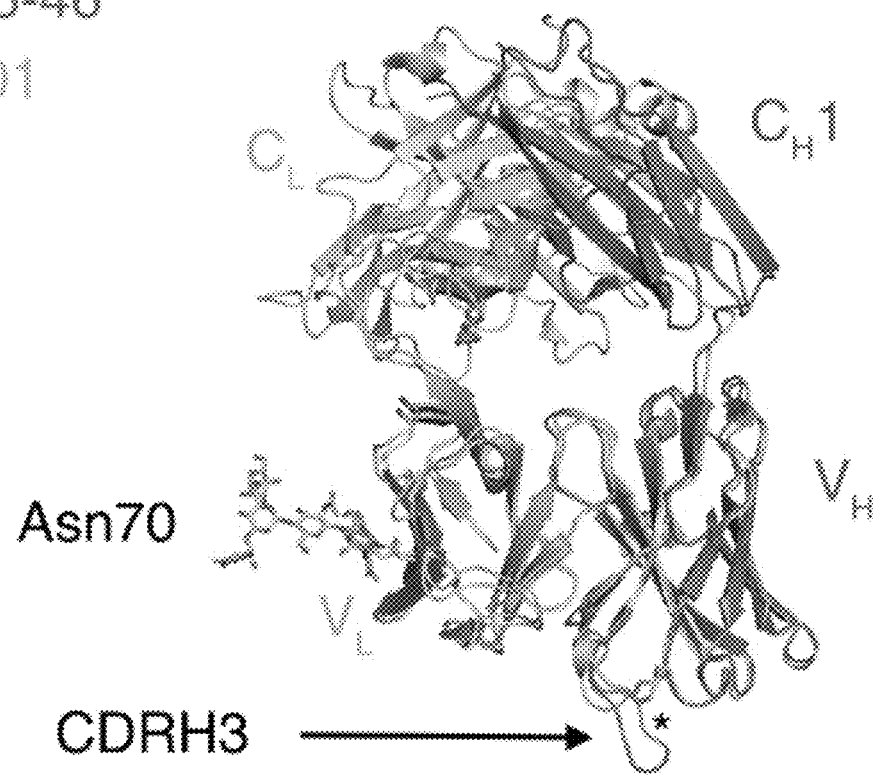
FIG. 4A is a superimposition and comparison of a structural depiction of NIH45-46-gp120 complex (shown in magenta) and a structural depiction of VRCO1-gp120 complex (shown in blue), according to embodiments of the present invention.
Figure 4B:
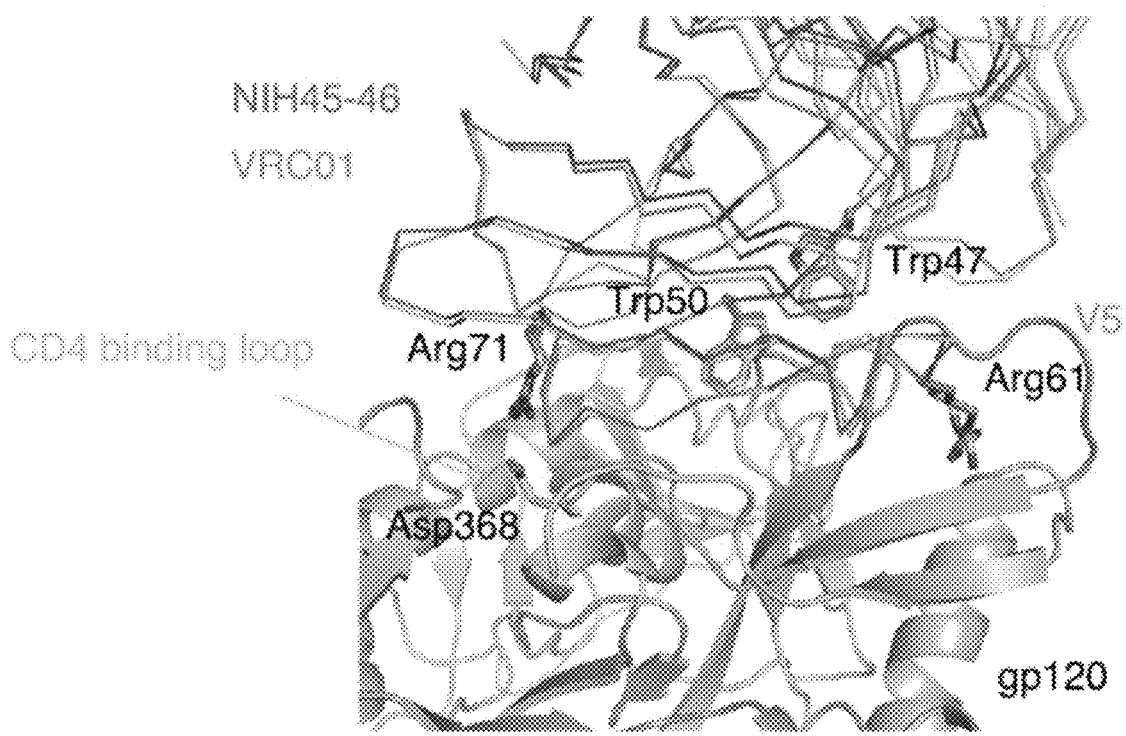
FIG. 4B is close-up view of the conserved interactions in the gp120 contacts of NIH45-46 and VRCO1, with the CD4 binding loop of gp120 labeled and shown in yellow, according to embodiments of the present invention.

Example 1. Structural Comparisons of NIH45-46 and VRC01. To determine structural correlates of high potency and breadth in HAADs, structures of NIH45-46 alone and bound to the clade A/E 93TH057 gp120 core were solved (FIGS. 1A, 1B and 2). NIH45-46 is a more potent clonal variant of VRC01 that was isolated from the same donor using a YU2 trimer (Sheid et al., 2011, supra), instead of a resurfaced gp120 core (RSC3) as a bait. Comparisons of NIH45-46 Fab in its free versus gp120-bound states demonstrate that gp120 binding does not require major conformational changes (FIG. 1A). However, gp120 binding induced minor conformational in CDRL1, CDRH3, and in heavy chain framework region 3 (FWR3). As predicted by high sequence identity (85% in $V_H$; 96% in $V_L$) (FIGS. 3A and 3B), NIH45-46 resembles VRC01 (FIGS. 4A and 4B). However, relative to VRC01, NIH45-46 includes a four-residue insertion within CDRH3 (FIG. 5) that was acquired by somatic hypermutation. (See, Sheid et al., 2011, Science, 333:1633-1637, the entire contents of which are incorporated herein by reference.)

Figure 5:
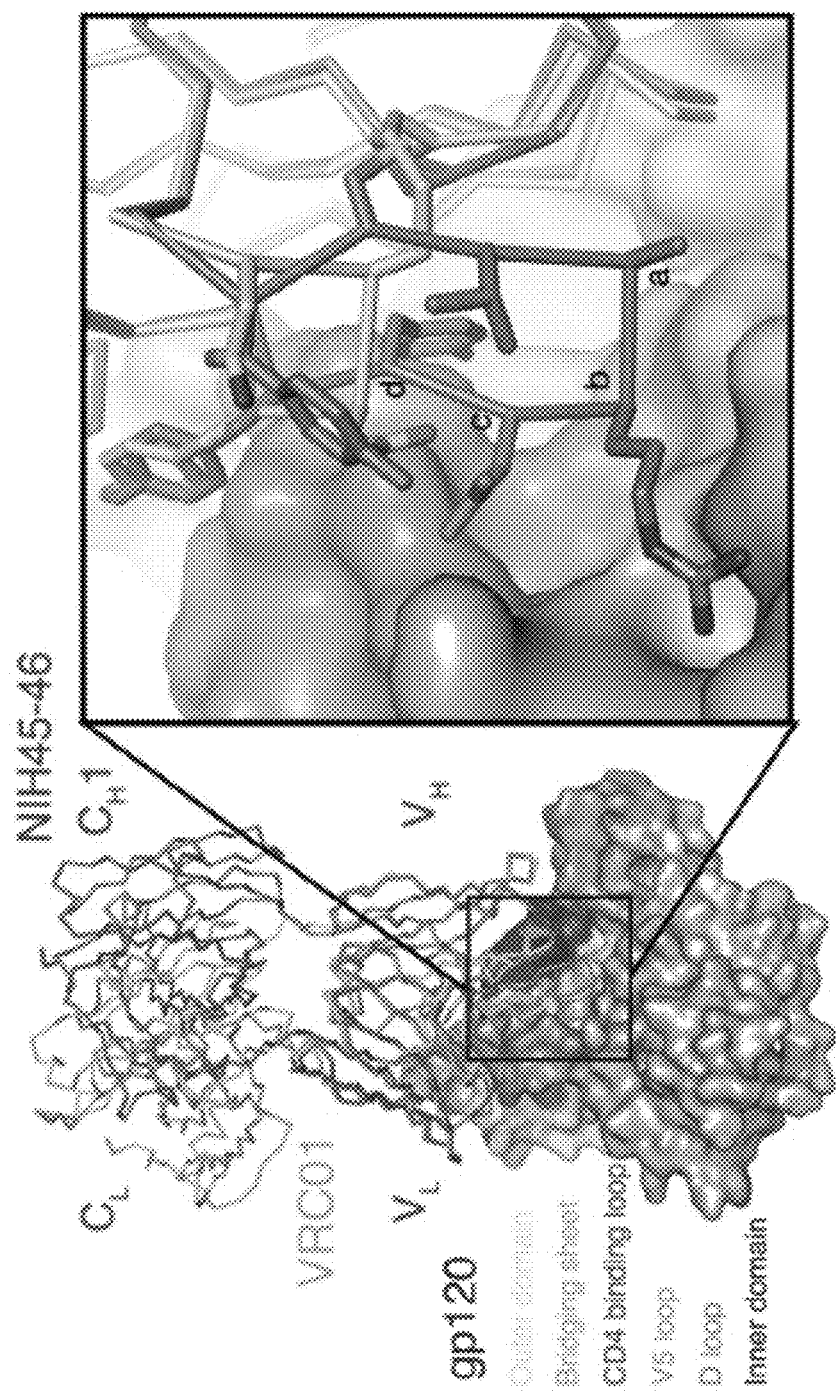
FIG. 5 is a depiction of the interactions of NIH45-46-gp120 complex and VRC01-gp120 complex with NIH45-46 shown in magenta, VRC01 in blue, and domains of gp120 shown as follows: outer domain (yellow), bridging sheet (orange), CD4 binding loop (blue), V5 loop and D Loop (green), and inner domain (grey); with the contact region between CDRH3 insertion residues of NIH45-46 and gp120 shown in the close-up box with insertion residues 99a-99b labeled alphabetically, according to embodiments of the present invention.
Figure 6A:
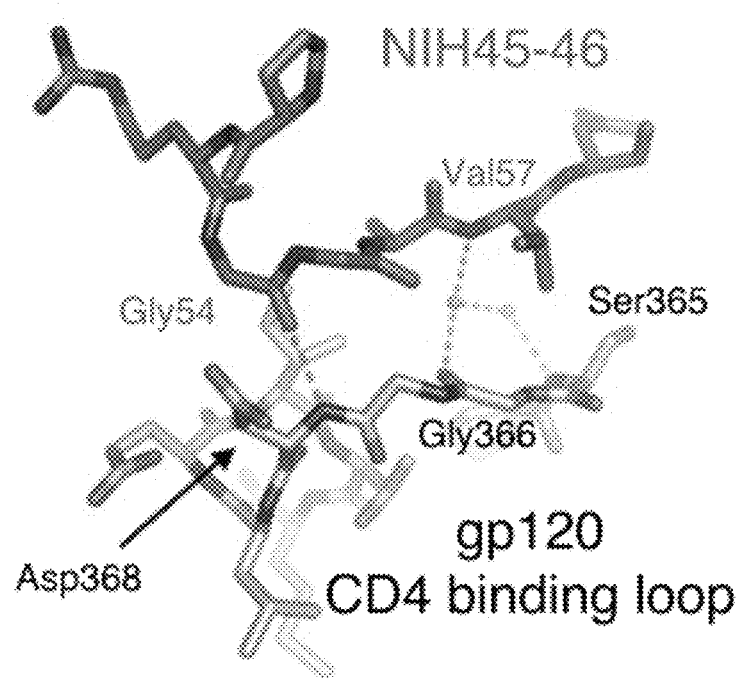
FIG. 6A is a structural depiction of the binding interface of a NIH45-46-gp120 complex characterized by the direct hydrogen bond (dotted line) between the main-chain atom of Gly54$_{NIH45-46}$ (magenta) and Asp368$_{gp120}$ (gray) and two water molecules (larger spheres in dotted line), according to aspects of the present invention.
Figure 6B:
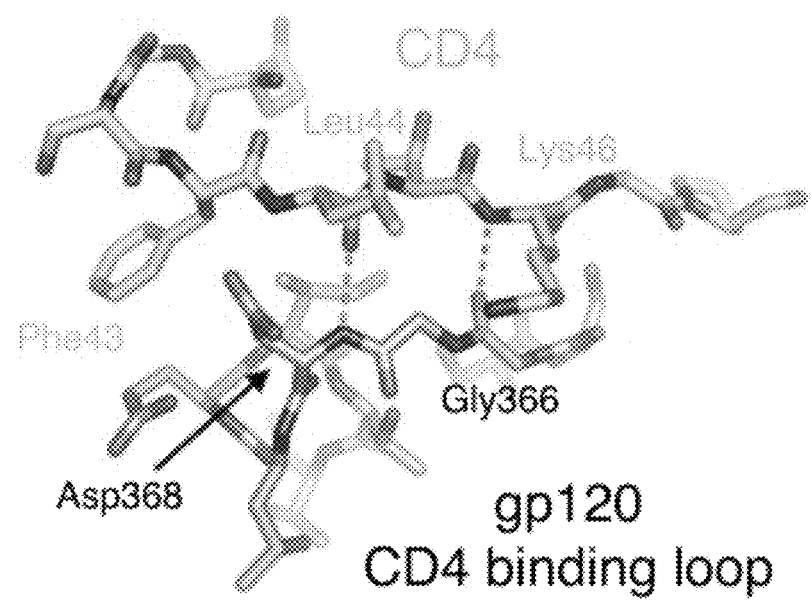
FIG. 6B is a structural depiction of the contact interface of a CD4-gp120 complex, characterized by CD4 (yellow) forming two direct hydrogen bonds (dotted lines) with the CD4-binding loop on gp120, according to embodiments of the present invention.
Figure 6C:
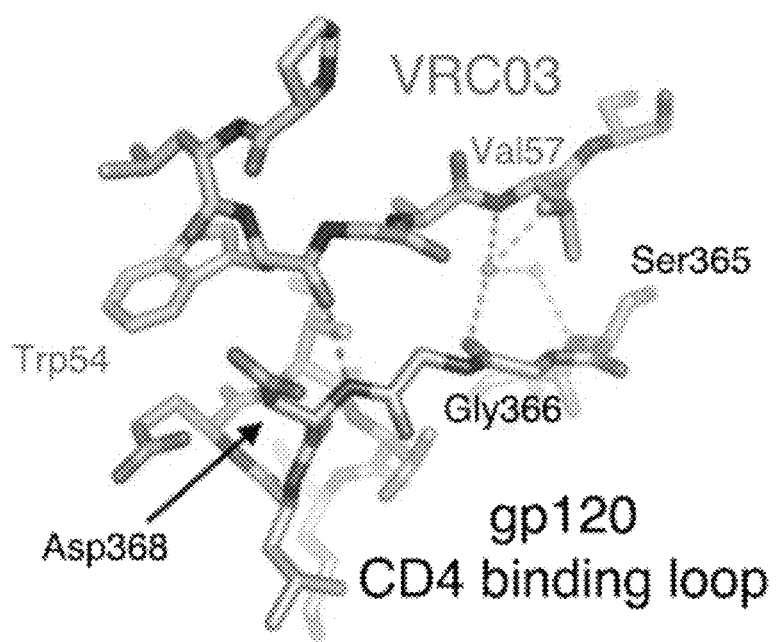
FIG. 6C is a structural depiction of the contact interface of a VRC03-gp120 complex, characterized by a carbonyl oxygen of Trp54$_{VRC03}$ forming a hydrogen bond with Asp368$_{gp120}$, according to embodiments of the present invention.
Figure 9A:
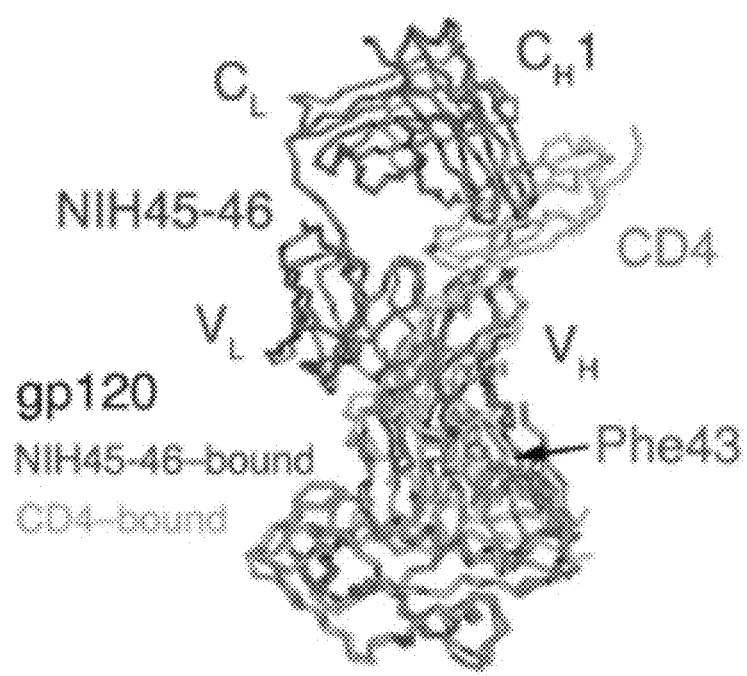
FIG. 9A is a structural depiction of NIH45-46-gp120 complex (with NIH45-46 shown in magenta and gp120 shown in grey) superimposed with a structural depiction of CD4-gp120 complex (with CD4 shown in yellow and gp120 shown in orange), with an arrow and label of Phe43 of CD4, according to embodiments of the present invention.
Figure 9B:
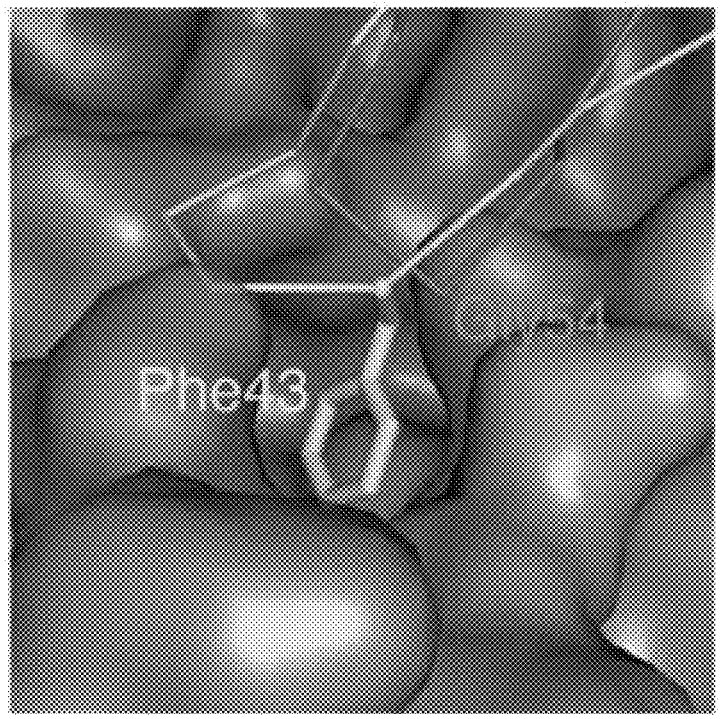
FIG. 9B is a close-up view of the superimposition of FIG. 9A with the CDRH2 loop of NIH45-46 (magenta) and the CDR2-like loop of CD4 (yellow) interacting with gp120 (grey surface), according to embodiments of the present invention.

The crystal structure of the NIH45-46-93TH057 gp120 complex verified that NIH45-46 targets the CD4bs on gp120 (FIGS. 1B and 5). The primary binding surface is the outer domain, including the CD4 binding loop (FIG. 6A), loop D and loop V5, but $CDRH3_{NIH45-46}$ reaches toward the gp120 inner domain (FIG. 1B, 2A-C). Important interactions in the VRC01-93TH057 structure are conserved in NIH45-46 (FIG. 4B); e.g., residues C-terminal to CDRH2 of VRC01 and NIH45-46 mimic the interaction of main-chain atoms in the C" β-strand of CD4 domain, which hydrogen bond with the CD4-binding loop of gp120 (FIGS. 6A, 6B,and 6C). In both NIH45-46 and VRC01, hydrogen bonds between CDRH2 and gp120 are water-mediated (except for the $Gly54_{NIH45-46}/Gly54_{VRC01}$ carbonyl oxygen-$Asp368_{gp120}$ backbone nitrogen H-bond (FIGS. 6A, 6B, and 6C)), and $Arg71_{VRC01}/Arg71_{NIH45-46}$ preserves the $Arg59_{CD4}$ interaction with $Asp368_{gp120}$. However, the $Phe43_{CD4}$ interaction with a hydrophobic pocket between α-helix $3_{gp120}$ (CD4 binding loop) and 0-strand $21_{gp120}$ (bridging sheet) (FIGS. 9A and 9B) is not mimicked by either antibody. Differences between VRC01 and NIH45-46 include the conformation of heavy chain residue Tyr74, a FWR3 residue that was substituted during somatic hypermutation (Sheid et al., 2011, supra), and a tyrosine to serine substitution in CDRL1 (FIGS. 10A, 10B, 11A, and 11B).

A notable difference between VRC01 and NIH45-46 is the four-residue insertion (residues 99a-99d) in CDRH3. Three inserted residues contribute to binding to gp120 (FIG. 5—inset), consistent with deletion of the insertion resulting in about 10-fold reduced neutralization potencies (Tables 2 and 3, below).

TABLE 2

| In vitro neutralization $IC_{50}$ values (µg/mL) | | | | |
|---|---|---|---|---|
| Virus | Clade | NIH45-46 WT | NIH45-46 Y99dA | NIH45-46 Δ99a-99d |
| AC10.0.29 | B | 0.9 | 4.4 | 13 |
| TRO.11 | B | 1.9 | >50 | >50 |
| SC422661.8 | B | 0.05 | 0.08 | 1.4 |
| QH0692.42 | B | 0.7 | 2.1 | 3.7 |
| ZM214M.PL15.11 | C | 0.3 | 1.1 | 2.2 |
| CAP45.2.00.G3 | C | >50 | >50 | >50 |
| T257-31 | CRF02 (A/G) | 0.5 | 2.4 | 7.0 |

TABLE 3

| | CDRH3 sequence |
|---|---|
| NIH45-46 WT | FCTRGKYCTARDYYNWDFEHWGRGAP |
| NIH45-46 Y99dA | FCTRGKYCTARDAYNWDFEHWGRGAP |
| NIH45-46 Δ99a-99d | FCTRGKYCT----YNWDFEHWGRGAP |

Figure 7:
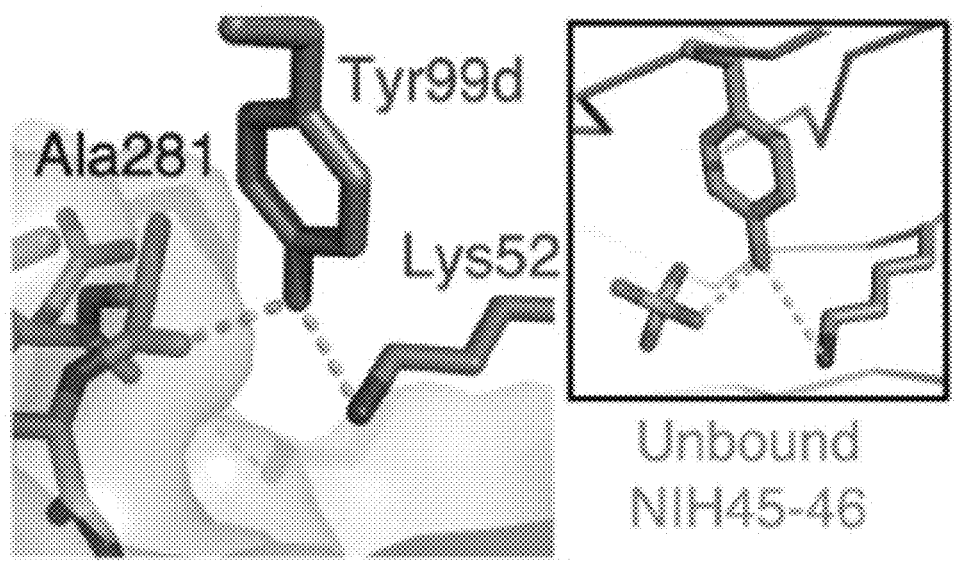
FIG. 7 is a structural depiction of the binding interface of a NIH45-46-gp120 complex, as shown by a hydrogen bond network between the main-chain carbonyl oxygen of Ala281$_{gp120}$, Tyr99d$_{NIH45-46}$ in CDRH3, and Lys52$_{NIH45-46}$ in CDRH2, in which yellow dots represent hydrogen bonds, and as shown in the inset box: a sulfate ion (yellow) substitutes for Ala281$_{gp120}$ in the unbound NIH45-46, according to embodiments of the present invention.

First, the $Tyr99d_{NIH45-46}$ sidechain hydrogen bonds with the loop D $Ala281_{gp120}$ carbonyl oxygen (FIG. 7), a main-chain atom, thus preventing escape through mutation. Indeed, NIH45-46-sensitive strains accommodate different sidechains at position $281_{gp120}$ (Table 4, below).

TABLE 4

Comparison of in vitro neutralization for viral strains with differences at $281_{gp120}$

| Strain | gp120 sequence surrounding residue 281 | Residue $28_{gp120}$ | $IC_{50}$* µg/mL |
|---|---|---|---|
| Du156.12 | QLLLNGSLAEEEIIIKSENLTDNIKTIIVQLNQSIGINCTRPNNNTRKSV | I | 0.01 |
| ZM197M.PB7 | QLLLNGSLAEEEIIIRSENLTDNTKTIIVHLNESVEIECVRPNNNTRKSV | T | 0.14 |
| ZM214M.PL15 | QLLLNGSLAEKEIMIRSENLTNNAKTIIVQLTEAVNITCMRPGNNTRRSV | A | 0.05 |
| ZM249M.PL1 | QLLLNGSLAEKEIIIRSENITDNVKIIIVHLNESVEINCTRPNNNTRKSI | V | 0.02 |
| ZM53M.PB12 | QLLLNGSTAEEDIIIRSENLTNNAKTIIVHLNESIEIECTRPGNNTRKSI | A | 0.65 |
| ZM109F.PB4 | QLLLNGSLAEEEIVIRSENLTDNAKTIIVHLNKSVEIECIRPGNNTRKSI | A | 0.22 |
| ZM135M.PL10a | QLLLNGSLSEEGIIIRSKNLTDNTKTIIVHLNESVAIVCTRPNNNTRKSI | T | 0.36 |

Figure 8:
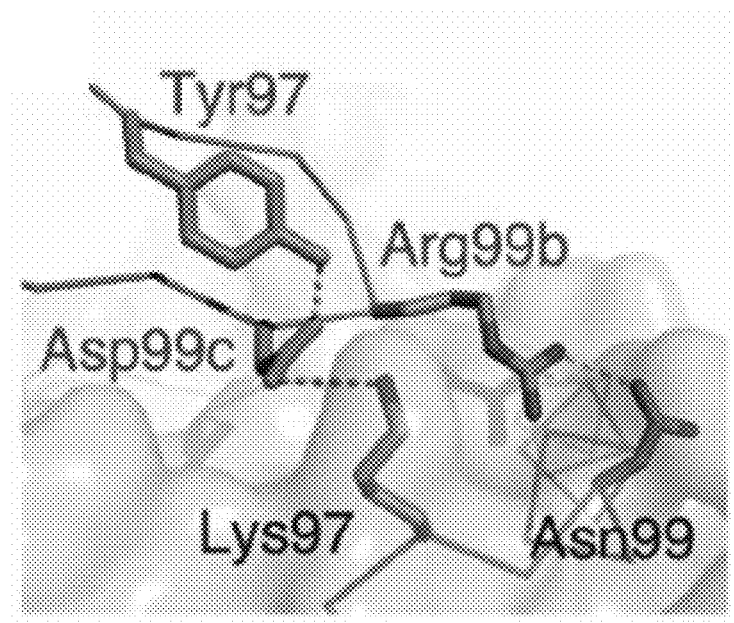
FIG. 8 is a structural depiction of the binding interface of a NIH45-46-gp120 complex, as shown by the electrostatic interactions between Asp99c$_{NIH45-46}$ and Lys97$_{gp120}$ (lower left dotted line) and hydrogen bonds between Asp99c$_{NIH45-46}$-Tyr97$_{NIH45-46}$ (upper left dotted line) and Arg99b$_{NIH45-46}$-Asn99$_{gp120}$ (lower right dotted line), according to embodiments of the present invention.
Figure 9C:
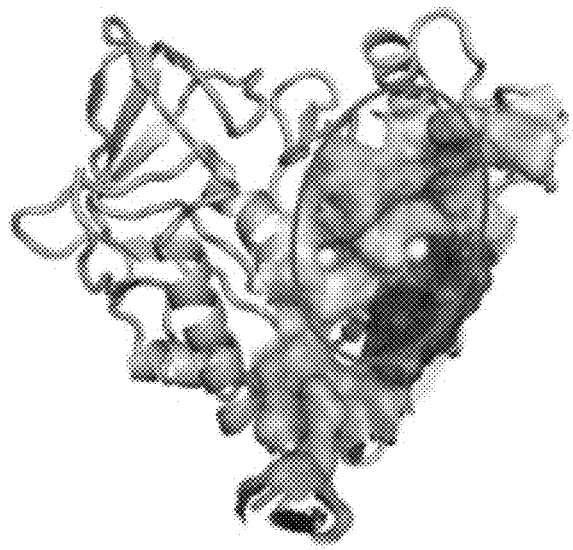
FIG. 9C is a structural depiction of a CD4-gp120 (ZM135M.PL10a) complex with the contact interface labeled and colored as in FIG. 1B, and the initial site of CD4 attachment is indicated with the oval, according to embodiments of the present invention.
Figure 10A:
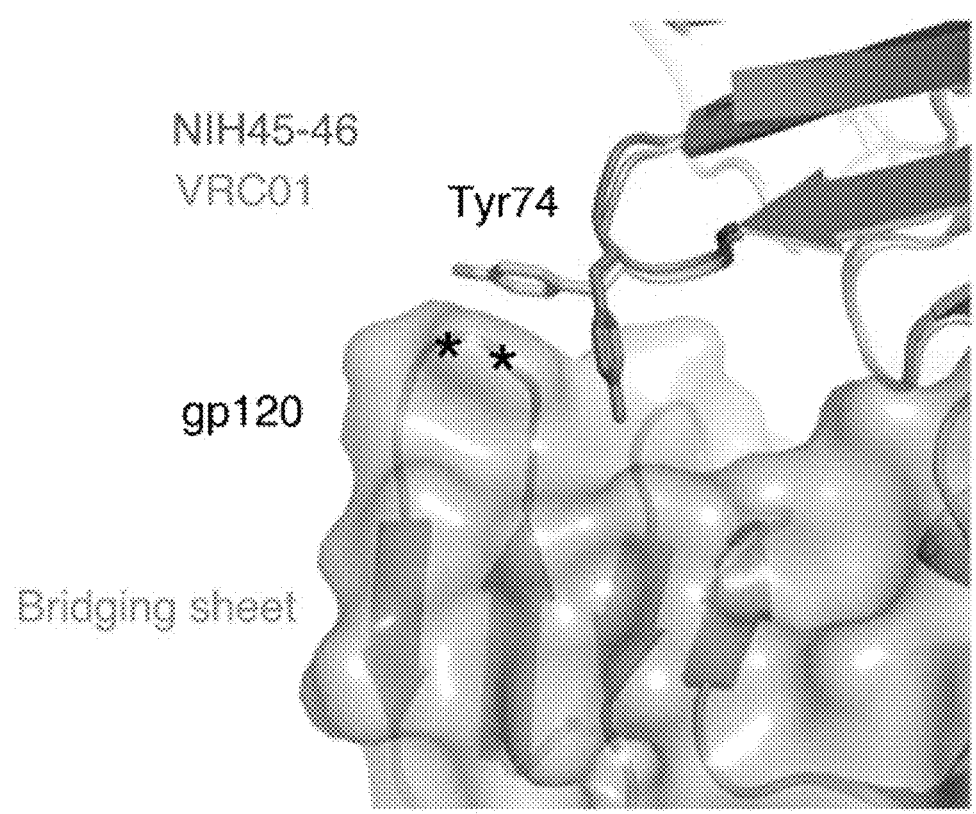
FIG. 10A is a structural depiction of a NIH45-46-gp120 complex superimposed with a VRC01-gp120 complex, in which the Tyr74 shows different interactions with gp120, and the gp120 bridging sheet is depicted with the broad arrows in gp120 and the asterisks indicate a recombinant Gly$_2$ linker, according to embodiments of the present invention.
Figure 10B:
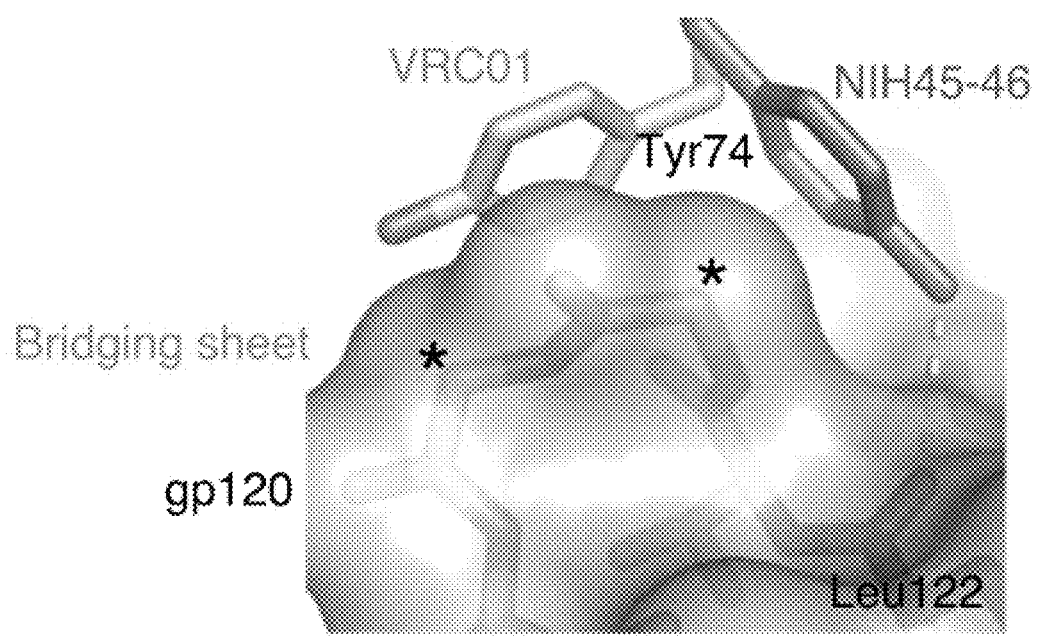
FIG. 10B is a close-up view of the structural depiction of FIG. 10A showing the hydrogen bond between Tyr74$_{NIH45-46}$ and the main-chain carbonyl oxygen of Leu122$_{gp120}$, according to embodiments of the present invention.
Figure 12:
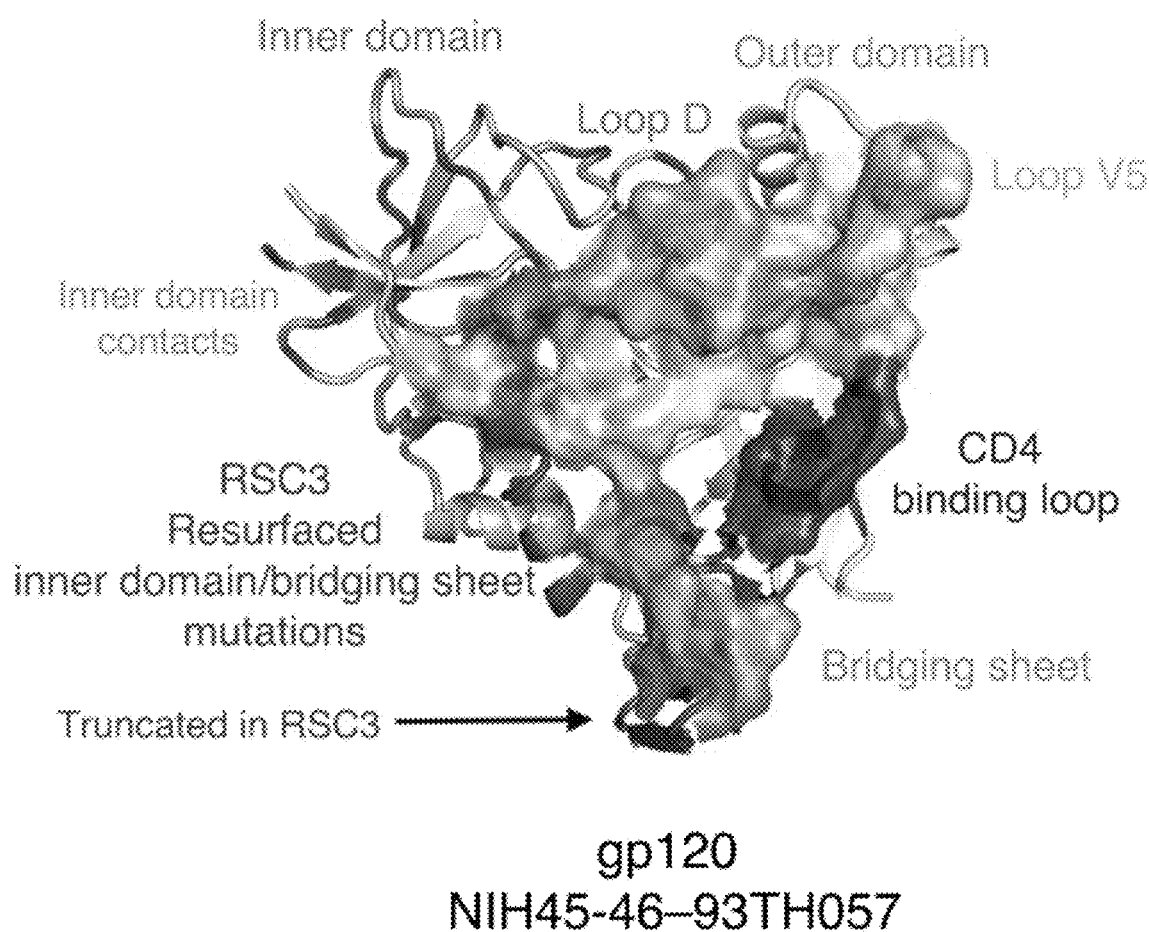
FIG. 12 is a structural depiction of gp120 and highlighted differences in the gp120 resurfaced stabilized core 3 (RSC3) variant, in which the NIH45-46 contact surfaces are shown and the RSC3 mutations shown, with labeling and coloring as in FIG. 1B, according to embodiments of the present invention.

The importance of Tyr99d$_{NIH45-46}$ for potency is demonstrated by alanine substitution (NIH45-46 Y99dA), which reduces the neutralization potency of NIH45-46 to values intermediate between wild-type NIH45-46 and the deletion mutant (Table 2). Second, Asp99c$_{NIH45-46}$ interacts electrostatically with Lys97$_{gp120}$ at the base of α-helix 1$_{gp120}$, and third, Arg99b$_{NIH45-46}$ hydrogen bonds with Asn99$_{gp120}$ (FIG. 8). The conformation of the insertion is stabilized by two intramolecular hydrogen bonds. In one, the Tyr99d$_{NIH45-46}$ sidechain hydrogen bonds with the ε-amino group of Lys52$_{NIH45-46}$ within CDRH2 (FIG. 7), also seen in the unbound structure of NIH45-46 (FIG. 7—inset), thus the Tyr99d$_{NIH45-46}$ hydroxyl is poised for interacting with Ala281$_{gp120}$. A second hydrogen bond between Tyr97$_{NIH45-46}$ and Asp99c$_{NIH45-46}$ in the gp120-bound Fab positions the negatively-charged aspartic acid for interaction with Lys97$_{gp120}$ (FIG. 8). The region of gp120 with which CDRH3$_{NIH45-46}$ interacts was not included in the previously-defined vulnerable site of initial CD4 attachment on the gp120 outer domain (FIG. 9C). Thus, gp120 residues that contact CDRH3$_{NIH45-46}$ residues required for potent neutralization (Table 2), e.g., Lys97$_{gp120}$, were mutated in RSC3 (FIG. 12), the resurfaced gp120 used for isolating bNAbs and as a candidate HIV immunogen.

The insertion in CDRH3 contributes to a higher total buried surface area between the NIH45-46 heavy chain and gp120 compared with VRC01 (Table 5, below). The extra contacts with gp120 created by the CDRH3 insertion allow the NIH45-46 footprint on gp120 to more closely resemble the CD4 footprint on gp120 than does the VRCO1 footprint (FIGS. 9C, 9D, and 9E, and Tables 5A and 5B, below).

TABLE 5A

| | Buried Surface Area (Å$^2$) | | | | | | | | |
|---|---|---|---|---|---|---|---|---|---|
| | FWR1 | CDR1 | FWR2 | CDR2 | FWR3 | CDR3 | Total Fab | Interface on gp120 | CDR2 + FWR3$_{56-65}$* |
| NIH45-46 HC | 0 | 35 | 51 | 181 | 551 | 326 | 1144 | 1097 | 576 |
| VRC01 HC | 0 | 20 | 98 | 136 | 521 | 117 | 892 | 882 | 545 |
| NIH45-46 LC | 35 | 8 | 0 | 0 | 0 | 159 | 203 | 192 | 0 |
| VRC01 LC | 36 | 114 | 0 | 0 | 0 | 165 | 314 | 367 | 0 |

*Residues that correspond to the CDR2 region as defined in Zhou et al., *Science*, 2010, 329: 811-817.

TABLE 5B

| | Inner domain & bridging sheet | Loop D + NAG | β-15/α-3 + NAG | V5 | β-24 | Outer domain exit loop | Total gp120 | Interface on Fab or CD4 |
|---|---|---|---|---|---|---|---|---|
| NIH45-46 | 328 | 335 | 222 | 292 | 81 | 35 | 1290 | 1346 |
| VRC01 | 157 | 433 | 208 | 328 | 43 | 57 | 1225 | 1206 |
| CD4 | 400 | 136 | 263 | 155 | 14 | 97 | 973 | 1059 |

The observation that NIH45-46 shows more extensive contacts relative to VRC01 with the inner domain and bridging sheet of gp120 (FIGS. 9D and 9E), yet exhibits higher potency and breadth (Sheid et al., 2001, supra), is inconsistent with the suggestion that increased contact area with regions outside of the outer domain of gp120 correlate with decreased neutralization potency and/or breadth (Zhou et al., 2010 supra; and Wu et al, 2011, *Science*, 333:1593-1602). Indeed, the observed CDRH3 contacts with the inner domain imply that the crystallographically-observed conformation of this region, whether pre-existing or induced, actively played a role in the affinity maturation events that resulted in the four-residue insertion with CDRH3.

Example 2. Hydrophobic amino acid substitution at position 54 of NIH45-46. Although NIH45-46 increases its contacts with the inner domain/bridging sheet area of gp120, like VRC01, it lacks a critical CD4 contact to a hydrophobic pocket at the boundary between the gp120 bridging sheet and outer domain made by burying Phe43$_{CD4}$. This residue alone accounts for 23% of the interatomic contacts between CD4 and gp120, serving as a "linchpin" that welds CD4 to gp120 (Kwong et al., 1998, *Nature*, 393:648-659). On gp120, the Phe43 binding cavity is a binding site of small-molecule CD4 mimics (Madani et al., 2008, *Structure*, 16:1689-1701), and a desirable target for compounds to disrupt CD4-gp120 interactions (Kwong et al., 1998, supra), yet it remains unfilled in the 93TH057 complexes with VRC01 (Zhou et al., 2010, supra) and NIH45-46. In a superimposition of a CD4-gp120 structure and NIH45-46-gp120 (FIG. 9B), the Cα atom of heavy chain residue Gly54$_{NIH45-46}$ is only about 1.4 Å from the Phe43$_{CD4}$ Cα, suggesting that this important interaction might be mimicked by substituting Gly54$_{NIH45-46}$ with a large hydrophobic residue. Indeed, residue 54 of VRC03 is a tryptophan, and Trp54$_{VRC03}$ is accommodated within gp120's Phe43 binding cavity to mimic Phe43$_{CD4}$, while still maintaining its main-chain hydrogen bond with Asp368$_{gp120}$ (PDB 3SE8) (FIGS. 6A-6C). If increasing contacts with the inner domain/bridging sheet enhances antibody activity, as suggested by analysis of the NIH45-46-gp120 structure, then substituting Gly54$_{NIH45-46}$ with a large hydrophobic residue should increase the potency and breadth of NIH45-46.

Figure 13A:
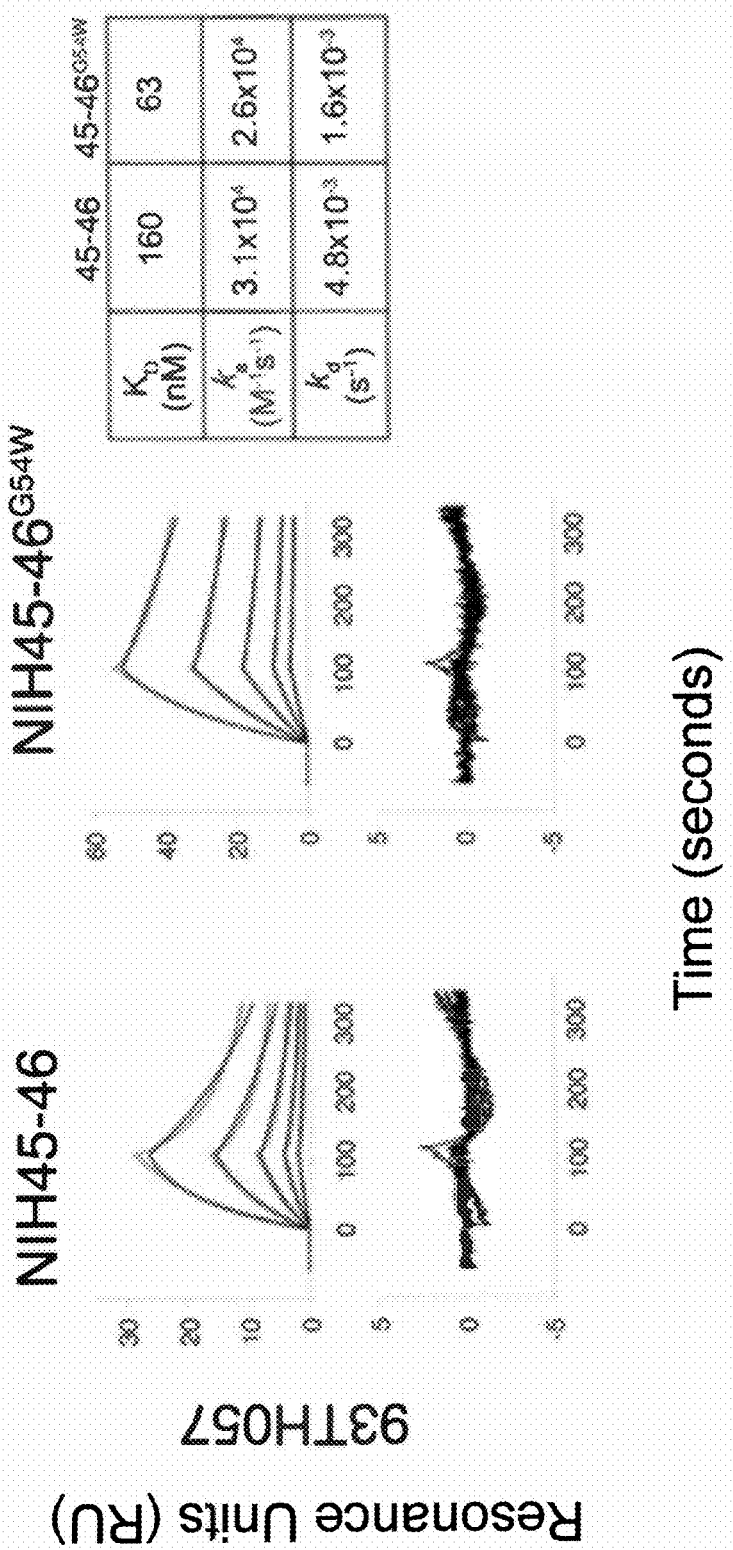
FIG. 13A shows sensorgrams from surface plasmon resonance (SPR) experiments of binding experiments of the 93TH057 gp120 protein with NIH45-46 and NIH45-46$^{G54W}$ Fabs, as indicated, and a table of the K$_D$ values is shown, according to embodiments of the present invention.
Figure 13C:
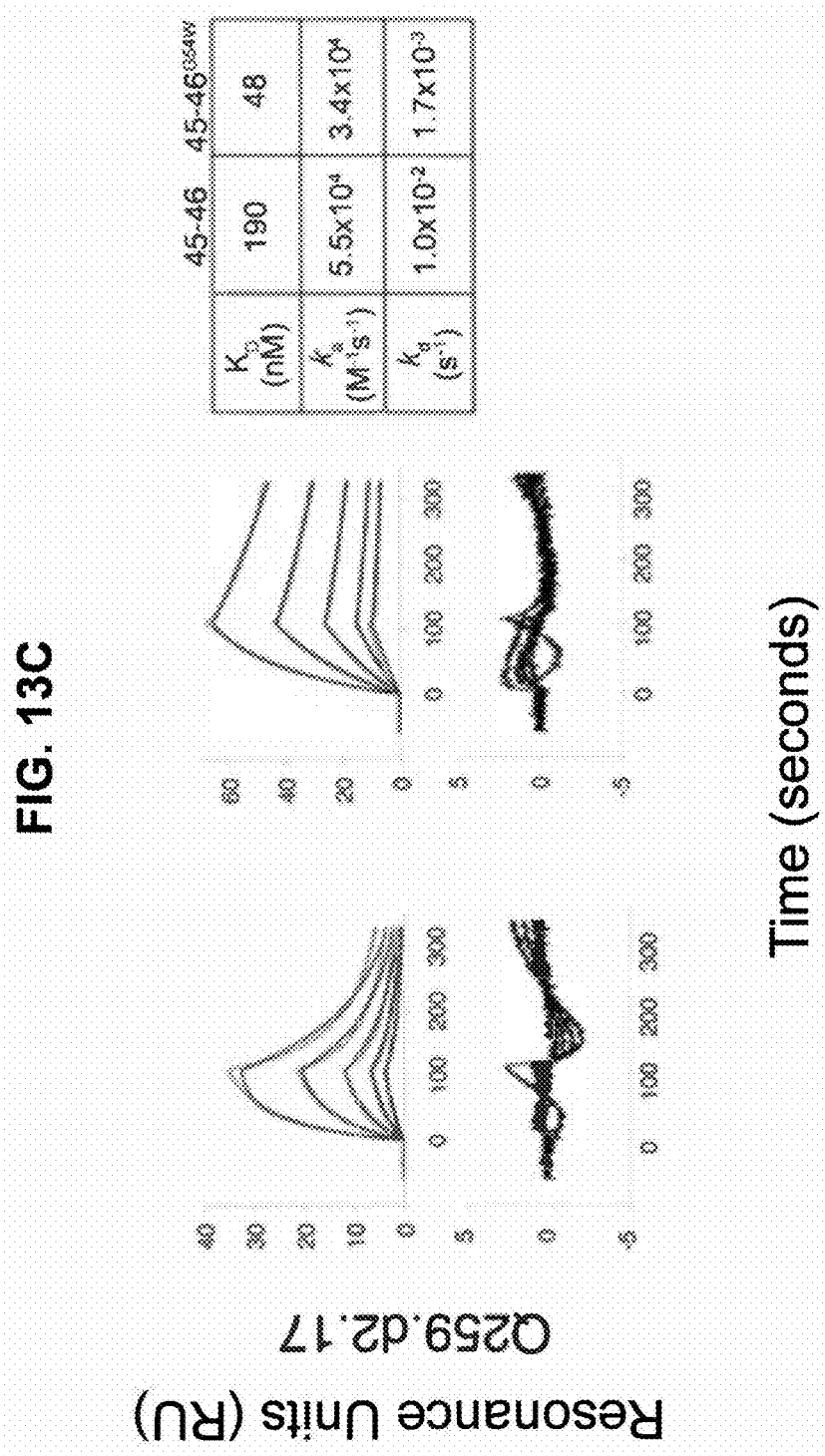
FIG. 13C shows sensorgrams from surface plasmon resonance (SPR) experiments of binding experiments of the Q259.d2.17 gp120 protein with NIH45-46 and NIH45-46$^{G54W}$ Fabs, as indicated, and a table of the K$_D$ values is shown, according to embodiments of the present invention.

A series of NIH45-46 mutants were constructed to test the possibility that a hydrophobic sidechain at position 54 in NIH45-46 would improve activity. First it was verified that substitutions at residue 54 did not interfere with antigen binding by assessing the ability of one mutant, NIH45-46$^{G54W}$, to bind core gp120s. Surface plasmon resonance (SPR) binding analyses demonstrated that NIH45-46$^{G54W}$ Fab bound core gp120s with slightly higher affinities than did NIH45-46 Fab, with differences largely due to slower dissociation rates (FIGS. 13A, 13B, and 13C). Next mutant IgGs were evaluated in neutralization assays using a panel of six viruses chosen to include NIH45-46-sensitive and resistant strains (Table 6, below).

TABLE 6

| Virus | Clade | NIH45-46 IC$_{50}$ (μg/mL) | | | | | | |
|---|---|---|---|---|---|---|---|---|
| | | WT | G54W | G54F | G54Y | G54I | G54M | G54L | G54H |
| SC422661.8 | B | 0.06 | 0.03 | 0.02 | 0.06 | 0.1 | 0.06 | 0.1 | 0.09 |
| AC10.0.29 | B | 0.9 | 0.2 | 0.3 | 0.4 | 8.6 | 1.5 | 1.7 | 0.6 |
| TRO.11 | B | 1.0 | 0.09 | 0.08 | 0.1 | 10 | 0.3 | 0.3 | 0.2 |
| Du172.17 | C | >50 | 0.9 | 16 | >50 | >50 | >50 | >50 | >50 |
| CAP210.2.00.E8 | C | >50 | 41 | >50 | >50 | >50 | >50 | >50 | >50 |
| CAP45.2.00.G3 | C | >50 | 6.6 | >50 | 45 | >50 | >50 | >50 | >50 |

Figure 14:
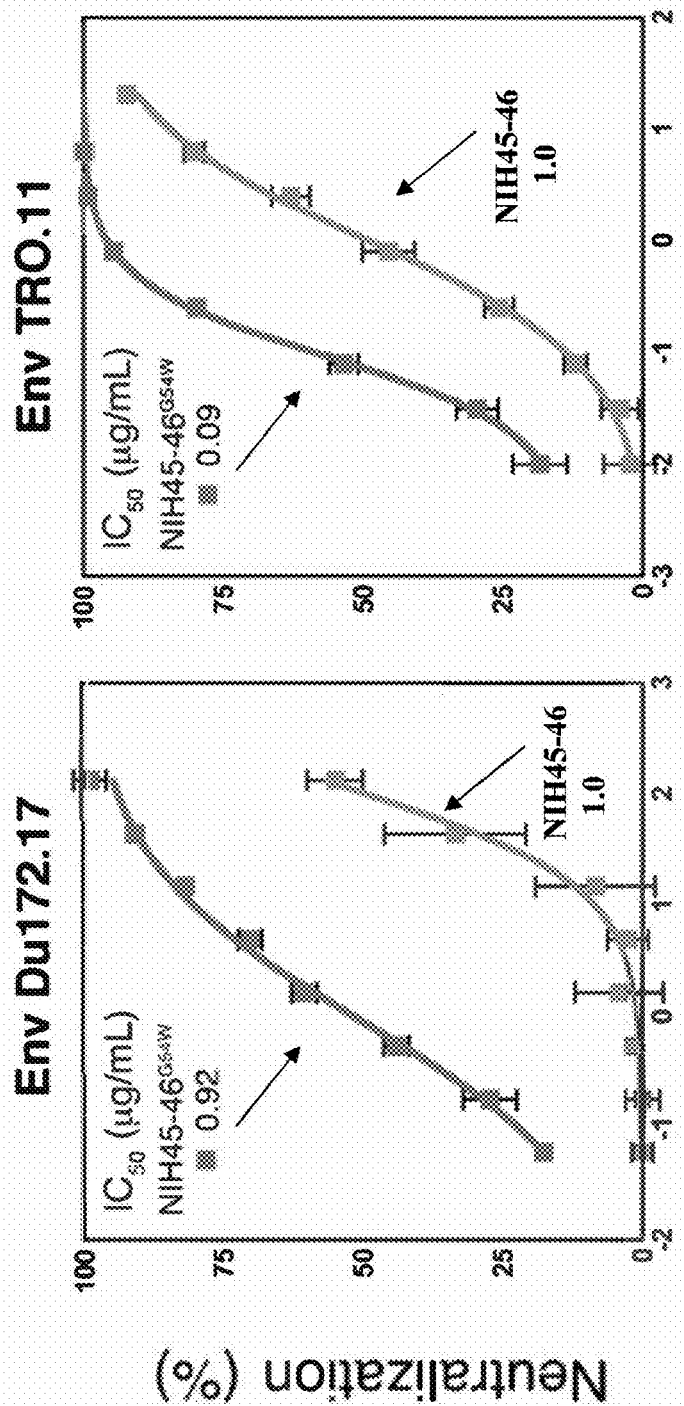
FIG. 14 shows neutralization curves for NIH45-46$^{G54W}$ and NIH45-46 in strains DU172.17 and TRO.11, as indicated, according to embodiments of the present invention.

NIH45-46$^{G54W}$ and NIH45-46$^{G54F}$ showed increased potencies and NIH45-46$^{G54W}$ increased breadth by neutralizing three strains that are resistant to >50 μg/mL of NIH45-46. The apparent increase in breadth is likely due to increased potency as evidenced by the extrapolated IC$_{50}$ for NIH45-46 against strain DU172.17 (FIG. 14).

Figure 15A:
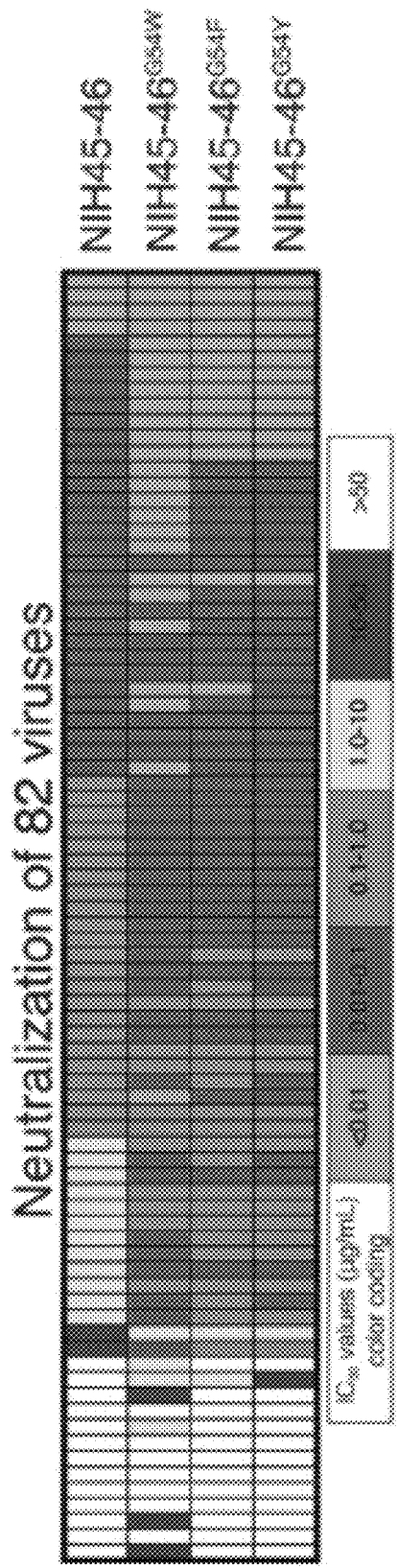
FIG. 15A shows a schematic comparing neutralization potencies of NIH45-46, NIH45-46$^{G54W}$, NIH45-46$^{G54F}$, and NIH45-464, with IC$_{50}$ values for each color-coded as shown, according embodiments of the present invention.

An additional 82 viruses were tested including 13 NG54-46-resistant, 14 weakly-neutralized, and 55 sensitive strains representing all clades, of which 12 are transmitted founder viruses (FIG. 15A, and Tables 7 and 8, below).

TABLE 7

In vitro neutralization IC$_{50}$ values (μg/mL) in the "hard panel" of viruses

| Virus | Clade | Category | NIH45-46 IC$_{50}$ (μg/mL) | | | |
|---|---|---|---|---|---|---|
| | | | WT | G54W | G54F | G54Y |
| 6545.v4.c1 | AC | R | >50 | 18.92 | >50 | >50 |
| 6540.v4.c1 | AC | R | >50 | >50 | >50 | >50 |
| CAP45.2.00.G3 | C | R | >50 | 32.25 | >50 | >50 |
| Du422.1 | C | R | >50 | >50 | >50 | >50 |
| CAP210.2.00.E8 | C | R | >50 | >50 | >50 | >50 |
| 3817.v2.c59 | CD | R | >50 | >50 | >50 | >50 |
| 89-F1_2_25 | CD | R | >50 | >50 | >50 | >50 |
| 620345.c01 | CRF01_AE | R | >50 | >50 | >50 | >50 |
| T250-4 | CRF02_AG | R | >50 | 1.33 | >50 | >50 |
| T278-50 | CRF02_AG | R | >50 | >50 | >50 | >50 |
| 211-9 | CRF02_AG | R | >50 | 16.41 | >50 | >50 |

TABLE 7-continued

In vitro neutralization IC$_{50}$ values (μg/mL) in the "hard panel" of viruses

| | | | NIH45-46 IC$_{50}$ (μg/mL) | | | |
|---|---|---|---|---|---|---|
| Virus | Clade | Category | WT | G54W | G54F | G54Y |
| 3016.v5.c45 | D | R | >50 | 1.47 | 5.82 | 17.89 |
| Du172.17 | C | R | >50 | 3.65 | >50 | >50 |
| 3718.v3.c11 | A | P | 19.61 | 0.01 | 0.32 | 0.30 |
| 703357.C02 | CRF01_AE | P | 19.17 | 3.43 | 7.91 | 5.60 |
| CNE20 | BC | P | 7.83 | 0.04 | 0.53 | 0.33 |
| CNE21 | BC | P | 6.01 | 0.03 | 0.12 | 0.07 |
| HIV-16845-2.22 | C | P | 5.00 | 0.45 | 0.59 | 0.59 |
| C2101.c01 | CRF01_AE | P | 4.24 | 0.04 | 0.11 | 0.09 |
| ZM247v1(Rev-) | C | P, T/F | 2.94 | 0.32 | 0.28 | 0.42 |
| ZM233M.PB6 | C | P | 2.50 | 0.02 | 0.22 | 0.16 |
| C1080.c03 | CRF01_AE | P | 2.48 | 0.20 | 0.36 | 0.29 |
| THRO4156.18 | B | P | 1.91 | 0.54 | 0.89 | 0.66 |
| 3103.v3.c10 | ACD | P | 1.770 | 0.200 | 0.370 | 0.300 |
| 231966.c02 | D | P | 1.640 | 0.020 | 0.060 | 0.060 |
| TRO.11 | B | P | 1.610 | 0.040 | 0.110 | 0.080 |
| T251-18 | CRF02_AG | P | 1.350 | 0.260 | 0.410 | 0.350 |
| Ce1176_A3 | C | S, T/F | 0.930 | 0.160 | 0.240 | 0.210 |
| QH0692.42 | B | S | 0.720 | 0.370 | 0.560 | 0.520 |
| T255-34 | CRF02_AG | S | 0.710 | <0.001 | 0.030 | 0.040 |
| ZM135M.PL10a | C | S | 0.590 | 0.040 | 0.130 | 0.090 |
| AC10.0.29 | B | S | 0.560 | 0.130 | 0.240 | 0.190 |
| T257-31 | CRF02_AG | S | 0.490 | 0.130 | 0.170 | 0.180 |
| CNE58 | BC | S | 0.430 | 0.020 | 0.040 | 0.040 |
| Ce0393_C3 | C | S, T/F | 0.334 | 0.013 | 0.040 | 0.036 |
| R1166.c01 | CRF01_AE | S | 0.310 | 0.130 | 0.400 | 0.240 |
| CNE30 | BC | S | 0.309 | 0.052 | 0.100 | 0.099 |
| CNE17 | BC | S | 0.261 | 0.036 | 0.075 | 0.073 |
| X2131_C1_B5 | G | S | 0.230 | 0.050 | 0.100 | 0.100 |
| 928-28 | CRF02_AG | S | 0.230 | 0.060 | 0.110 | 0.120 |
| 6535.3 | B | S | 0.230 | 0.030 | 0.070 | 0.080 |
| ZM53M.PB12 | C | S | 0.175 | 0.040 | 0.080 | 0.060 |
| ZM214M.PL15 | C | S | 0.170 | 0.030 | 0.090 | 0.060 |
| Ce703010054_2A2 | C | S, T/F | 0.159 | 0.027 | 0.020 | 0.022 |
| ZM197M.PB7 | C | S | 0.150 | 0.040 | 0.090 | 0.070 |
| CAAN5342.A2 | B | S | 0.150 | 0.070 | 0.100 | 0.100 |
| Q23.17 | A | S | 0.140 | 0.010 | 0.030 | 0.020 |
| PVO.4 | B | S | 0.120 | 0.050 | 0.070 | 0.060 |
| 1054_07_TC4_1499 | B | S, T/F | 0.113 | 0.040 | 0.076 | 0.064 |
| Ce2010_F5 | C | S, T/F | 0.101 | 0.038 | 0.046 | 0.049 |
| ZM109F.PB4 | C | S | 0.095 | 0.002 | 0.022 | 0.026 |
| 1056_10_TA11_1826 | B | S, T/F | 0.094 | 0.024 | 0.064 | 0.044 |
| 0330.v4.c3 | A | S | 0.090 | 0.030 | 0.040 | 0.030 |
| P1981_C5_3 | G | S | 0.080 | 0.020 | 0.030 | 0.040 |
| Q461.e2 | A | S | 0.076 | 0.009 | 0.030 | 0.023 |
| P0402_c2_11 | G | S | 0.073 | 0.003 | 0.008 | 0.012 |
| SC422661.8 | B | S | 0.060 | 0.020 | 0.040 | 0.040 |
| 62357_14_D3_4589 | B | S, T/F | 0.060 | 0.020 | 0.040 | 0.030 |
| WITO4160.33 | B | S | 0.060 | 0.010 | 0.020 | 0.030 |
| Ce2060_G9 | C | S, T/F | 0.058 | 0.005 | 0.022 | 0.021 |
| Ce0682_E4 | C | S, T/F | 0.054 | 0.010 | 0.011 | 0.017 |
| 231965.c01 | D | S | 0.051 | <0.001 | 0.022 | 0.025 |
| Q259.d2.17 | A | S | 0.043 | <0.001 | 0.009 | 0.009 |
| TRJO4551.58 | B | S | 0.040 | 0.010 | 0.030 | 0.030 |
| 6811.v7.c18 | CD | S | 0.035 | <0.001 | 0.017 | 0.011 |
| R2184.c04 | CRF01_AE | S | 0.034 | 0.005 | 0.015 | 0.015 |
| 6480.v4.c25 | CD | S | 0.032 | 0.004 | 0.014 | 0.018 |
| X1254_c3 | G | S | 0.032 | 0.002 | 0.011 | 0.013 |
| Q842.d12 | A | S | 0.031 | 0.005 | 0.011 | 0.015 |
| C3347.c11 | CRF01_AE | S | 0.029 | <0.001 | 0.015 | 0.011 |
| 1006_11_C3_1601 | B | S, T/F | 0.027 | <0.001 | 0.003 | 0.005 |
| 3415.v1.c1 | A | S | 0.022 | <0.001 | <0.001 | <0.001 |
| X1193_c1 | G | S | 0.021 | <0.001 | <0.001 | 0.006 |
| Du156.12 | C | S | 0.020 | <0.001 | <0.001 | 0.007 |
| RHPA4259.7 | B | S | 0.017 | <0.001 | 0.005 | 0.007 |
| ZM249M.PL1 | C | S | 0.017 | 0.002 | 0.004 | 0.003 |
| 0815.v3.c3 | ACD | S | 0.014 | <0.001 | <0.001 | <0.001 |
| REJO4541.67 | B | S | 0.014 | 0.002 | 0.007 | 0.007 |
| 3301.v1.c24 | AC | S | 0.009 | <0.001 | 0.001 | 0.003 |
| Q769.d22 | A | S | 0.009 | <0.001 | 0.005 | 0.007 |

TABLE 7-continued

In vitro neutralization IC$_{50}$ values (µg/mL) in the "hard panel" of viruses

| | | | NIH45-46 IC$_{50}$ (µg/mL) | | | |
|---|---|---|---|---|---|---|
| Virus | Clade | Category | WT | G54W | G54F | G54Y |
| CNE53 | BC | S | 0.008 | <0.001 | 0.005 | 0.006 |
| WEAU_d15_410_787 | B | S, T/F | 0.005 | <0.001 | <0.001 | 0.002 |
| Geometric means | | | 0.417 | 0.046 | 0.120 | 0.124 |

Category
R—Resistant
P—Poorly sensitive
S—Sensitive
T/F—Transmitted Founder

TABLE 8

In vitro neutralization IC$_{80}$ values (µg/mL) in the "hard panel" of viruses

| | | | NIH45-46 IC$_{80}$ (µg/mL) | | | |
|---|---|---|---|---|---|---|
| Virus | Clade | Category | WT | G54W | G54F | G54Y |
| T250-4 | CRF02_AG | R | >50 | 44.94 | >50 | >50 |
| 703357.C02 | CRF01_AE | R | >50 | 17.61 | >50 | 30.58 |
| CAP45.2.00.G3 | C | R | >50 | >50 | >50 | >50 |
| CNE20 | BC | R | >50 | 0.48 | 3.91 | 2.40 |
| CAP210.2.00.E8 | C | R | >50 | >50 | >50 | >50 |
| T278-50 | CRF02_AG | R | >50 | >50 | >50 | >50 |
| 211-9 | CRF02_AG | R | >50 | >50 | >50 | >50 |
| 620345.c01 | CRF01_AE | R | >50 | >50 | >50 | >50 |
| 3016.v5.c45 | D | R | >50 | 15.37 | 36.97 | >50 |
| 3817.v2.c59 | CD | R | >50 | >50 | >50 | >50 |
| 89-F1_2_25 | CD | R | >50 | >50 | >50 | >50 |
| 6540.v4.c1 | AC | R | >50 | >50 | >50 | >50 |
| 6545.v4.c1 | AC | R | >50 | >50 | >50 | >50 |
| Du422.1 | C | P | >50 | >50 | >50 | >50 |
| 3718.v3.c11 | A | P | >50 | 0.04 | 4.620 | 3.85 |
| Du172.17 | C | P | >50 | 42.85 | >50 | >50 |
| CNE21 | BC | P | 38.07 | 0.16 | 0.66 | 0.29 |
| C2101.c01 | CRF01_AE | P | 31.37 | 0.17 | 0.42 | 0.27 |
| ZM247v1(Rev-) | C | P, T/F | 24.50 | 2.60 | 2.45 | 3.57 |
| HIV-16845-2.22 | C | P | 22.61 | 2.10 | 2.75 | 2.75 |
| ZM233M.PB6 | C | P | 14.18 | 0.11 | 0.99 | 0.78 |
| C1080.c03 | CRF01_AE | P | 11.56 | 0.91 | 2.26 | 1.83 |
| 231966.c02 | D | P | 9.64 | 0.11 | 0.24 | 0.23 |
| THRO4156.18 | B | P | 8.22 | 1.81 | 3.01 | 2.14 |
| TRO.11 | B | P | 7.49 | 0.13 | 0.30 | 0.22 |
| 3103.v3.c10 | ACD | P | 6.15 | 0.56 | 1.28 | 0.81 |
| T251-18 | CRF02_AG | P | 3.68 | 0.92 | 1.38 | 1.16 |
| T255-34 | CRF02_AG | S | 3.442 | 0.099 | 0.198 | 0.174 |
| Ce1176_A3 | C | S, T/F | 3.17 | 0.45 | 0.83 | 0.58 |
| ZM135M.PL10a | C | S | 2.79 | 0.16 | 0.43 | 0.30 |
| CNE58 | BC | S | 2.08 | 0.05 | 0.11 | 0.11 |
| AC10.0.29 | B | S | 1.93 | 0.63 | 1.12 | 0.90 |
| QH0692.42 | B | S | 1.71 | 1.12 | 1.65 | 1.50 |
| T257-31 | CRF02_AG | S | 1.38 | 0.45 | 0.51 | 0.67 |
| R1166.c01 | CRF01_AE | S | 1.21 | 0.51 | 1.32 | 0.84 |
| CNE30 | BC | S | 1.067 | 0.196 | 0.348 | 0.263 |
| Ce0393_C3 | C | S, T/F | 0.936 | 0.089 | 0.173 | 0.134 |
| X2131_C1_B5 | G | S | 0.88 | 0.24 | 0.41 | 0.39 |
| CNE17 | BC | S | 0.734 | 0.127 | 0.287 | 0.264 |
| 928-28 | CRF02_AG | S | 0.64 | 0.25 | 0.41 | 0.33 |
| ZM53M.PB12 | C | S | 0.61 | 0.16 | 0.23 | 0.22 |
| ZM214M.PL15 | C | S | 0.59 | 0.15 | 0.30 | 0.23 |
| ZM197M.PB7 | C | S | 0.55 | 0.18 | 0.23 | 0.21 |
| 6535.3 | B | S | 0.54 | 0.13 | 0.27 | 0.24 |
| Ce703010054_2A2 | C | S, T/F | 0.538 | 0.077 | 0.070 | 0.070 |
| Q23.17 | A | S | 0.50 | 0.03 | 0.07 | 0.06 |
| 1056_10_TA11_1826 | B | S, T/F | 0.447 | 0.160 | 0.283 | 0.189 |
| ZM109F.PB4 | C | S | 0.437 | 0.070 | 0.17 | 0.168 |
| PVO.4 | B | S | 0.41 | 0.16 | 0.25 | 0.18 |
| 1054_07_TC4_1499 | B | S, T/F | 0.404 | 0.165 | 0.283 | 0.236 |
| CAAN5342.A2 | B | S | 0.40 | 0.21 | 0.28 | 0.27 |
| Ce2010_F5 | C | S, T/F | 0.357 | 0.187 | 0.186 | 0.235 |
| 0330.v4.c3 | A | S | 0.3 | 0.11 | 0.13 | 0.09 |
| Q461.e2 | A | S | 0.291 | 0.091 | 0.135 | 0.103 |

TABLE 8-continued

In vitro neutralization IC$_{80}$ values (μg/mL) in the "hard panel" of viruses

| Virus | Clade | Category | NIH45-46 IC$_{80}$ (μg/mL) | | | |
|---|---|---|---|---|---|---|
| | | | WT | G54W | G54F | G54Y |
| Ce2060_G9 | C | S, T/F | 0.290 | 0.042 | 0.085 | 0.068 |
| WITO4160.33 | B | S | 0.26 | 0.04 | 0.14 | 0.09 |
| P1981_C5_3 | G | S | 0.24 | 0.07 | 0.11 | 0.09 |
| P0402_c2_11 | G | S | 0.214 | 0.023 | 0.047 | 0.049 |
| 1006_11_C3_1601 | B | S, T/F | 0.196 | 0.008 | 0.024 | 0.021 |
| 62357_14_D3_4589 | B | S, T/F | 0.19 | 0.07 | 0.14 | 0.09 |
| Ce0682_E4 | C | S, T/F | 0.155 | 0.039 | 0.056 | 0.065 |
| Q259.d2.17 | A | S | 0.154 | 0.014 | 0.036 | 0.034 |
| SC422661.8 | B | S | 0.13 | 0.07 | 0.10 | 0.09 |
| TRJO4551.58 | B | S | 0.13 | 0.05 | 0.08 | 0.07 |
| R2184.c04 | CRF01_AE | S | 0.127 | 0.036 | 0.054 | 0.045 |
| 231965.c01 | D | S | 0.126 | 0.035 | 0.062 | 0.054 |
| 6811.v7.c18 | CD | S | 0.113 | 0.033 | 0.063 | 0.059 |
| X1254_c3 | G | S | 0.107 | 0.018 | 0.043 | 0.041 |
| 6480.v4.c25 | CD | S | 0.100 | 0.021 | 0.046 | 0.051 |
| C3347.c11 | CRF01_AE | S | 0.094 | 0.028 | 0.059 | 0.052 |
| 3415.v1.c1 | A | S | 0.086 | 0.023 | 0.029 | 0.037 |
| Q842.d12 | A | S | 0.073 | 0.025 | 0.039 | 0.045 |
| X1193_c1 | G | S | 0.064 | 0.009 | 0.026 | 0.024 |
| Du156.12 | C | S | 0.054 | 0.005 | 0.019 | 0.026 |
| ZM249M.PL1 | C | S | 0.053 | 0.007 | 0.016 | 0.011 |
| 0815.v3.c3 | ACD | S | 0.052 | 0.003 | 0.014 | 0.015 |
| RHPA4259.7 | B | S | 0.047 | 0.007 | 0.020 | 0.020 |
| CNE53 | BC | S | 0.039 | 0.005 | 0.024 | 0.027 |
| REJO4541.67 | B | S | 0.035 | 0.013 | 0.028 | 0.020 |
| 3301.v1.c24 | AC | S | 0.033 | 0.004 | 0.011 | 0.014 |
| Q769.d22 | A | S | 0.033 | 0.009 | 0.023 | 0.024 |
| WEAU_d15_410_787 | B | S, T/F | 0.015 | 0.003 | 0.004 | 0.008 |
| Geometric means | | | 1.231 | 0.225 | 0.437 | 0.393 |

Category
R—Resistant
P—Poorly sensitive
S—Sensitive
T/F—Transmitted Founder

Figure 15B:
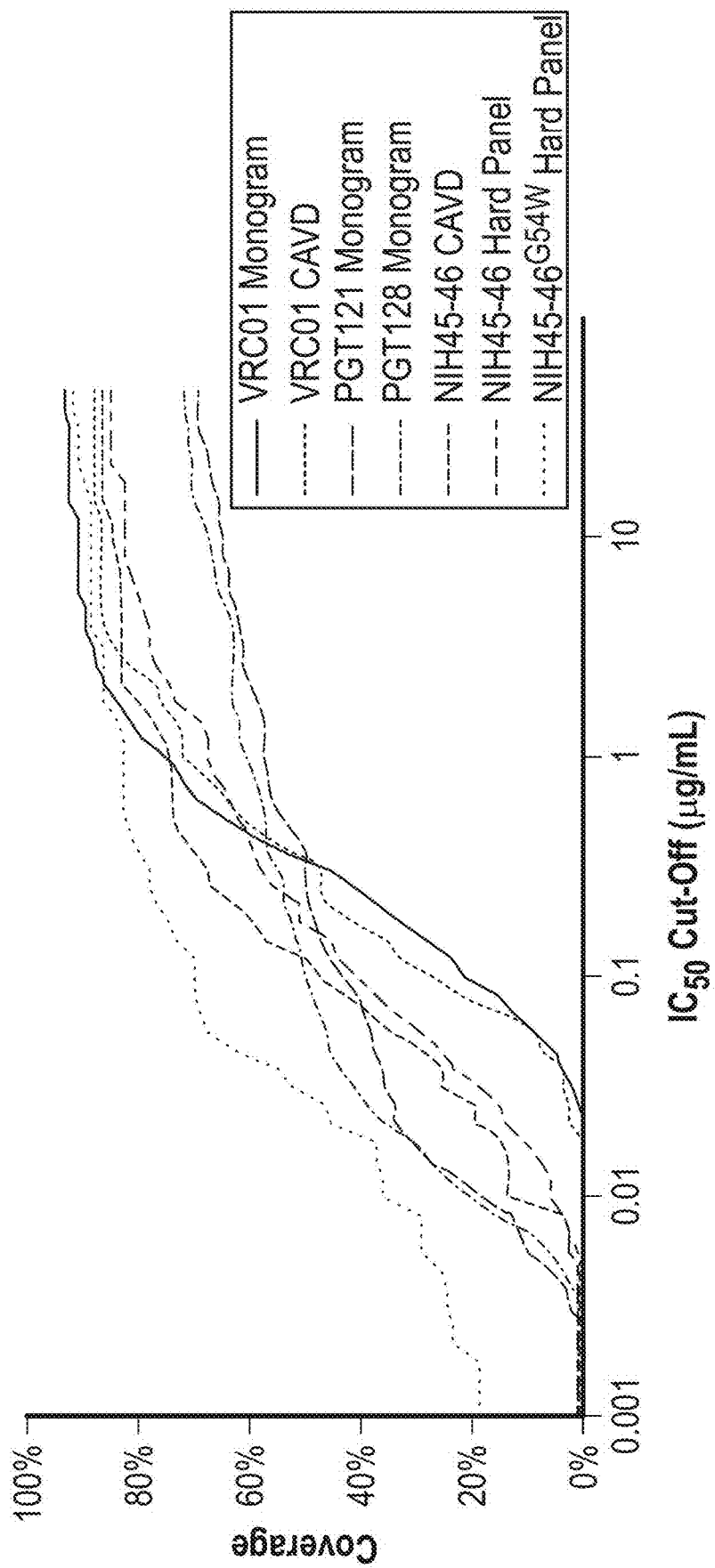
FIG. 15B shows a graphical comparison of neutralization coverage and potency for VRC01 Monogram (Monogram is a panel of 162 viral strains), VRC01 CAVD (CAVD is a panel of 118 viral strains), PGT121 Monogram, PGT128 Monogram, NIH45-46 CAVD, NIH45-46 hard panel (See Tables 7 and 8), and NIH45-46G54W hard panel, according to embodiments of the present invention.
Figure 15C:
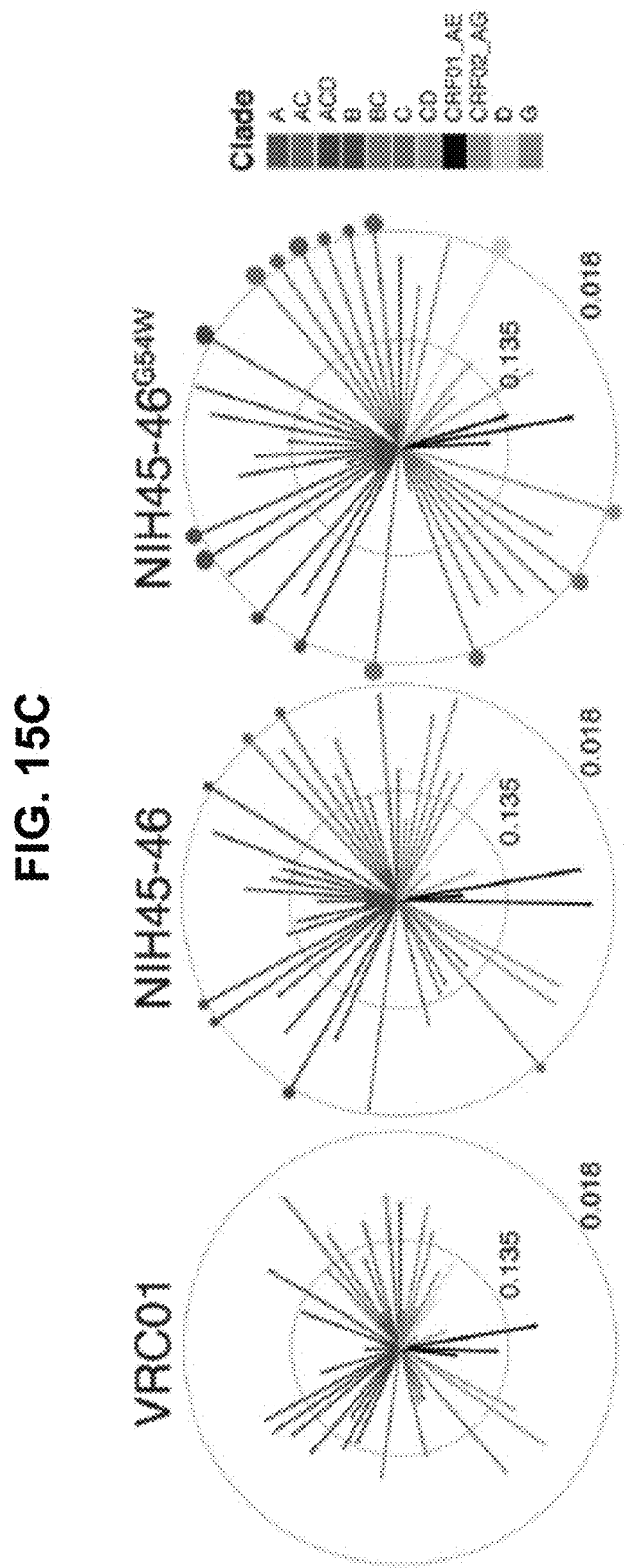
FIG. 15C shows neutralization summary spider graphs comparing IC$_{50}$ values for VRC01, NIH45-46, and NIH45-46$^{G54W}$ for 65 common viruses, in which each color represents a different HIV clade, the length of the lines and size of circles are inversely proportional to the IC$_{50}$ value, the distance between the outer and the inner circle and the distance from the inner circle to the center of a spider graph each span two natural logs in IC$_{50}$ concentration, the dots on the outer circle indicate strains with IC$_{50}$ values less than 0.018 μg/ml whose lines were truncated in the graph, and the size of each dot is inversely proportional to the IC$_{50}$ value, according to embodiments of the present invention.

The above panel of viruses in Tables 7 and 8 (referred to as the "hard panel") is more difficult for NIH45-46 to neutralize than a recently-published panel (Sheid et al, 2011, supra) (FIG. 15B). NIH45-46$^{G54W}$ showed increased potency and breadth compared to NIH45-46 and VRC01: geometric mean IC$_{50}$s of 0.04 μg/mL for NIH45-464W, 0.41 μg/mL for NIH45-46, and 0.92 μg/mL for VRC01 (calculated for 65 viruses against which VRC01 was previously evaluated (Sheid et al, 2011, supra) (Tables 7 and 8, and FIG. 15C). (Geometric IC$_{50S}$ values were calculated without excluding resistant strains by entering values of 50 μg/ml for strains with IC$_{50}$ values greater than 50 μg/ml).

TABLE 9

Sequence correlates of resistance to NIH45-46

| Strain | | | |
|---|---|---|---|
| 620345_c1 | Ser456 (Arg) | Asp459 (Gly) | Lys279 (Asn/Asp) |
| 89_F1_2_25 | Ser456 (Arg) | Asn458 (Gly) | |
| 6540_v4_c1 | Ser456 (Arg) | Tyr458 (Gly) | Ser280 (Asn) |
| 6545_v4_c1 | Ser456 (Arg) | Tyr458 (Gly) | Ser280 (Asn) |
| Du422.1 | Trp456 (Arg) | | |
| T250_4 | Pro459 (Gly) | | |
| T278_50 | Glu459 (Gly) | Ala279 (Asn/Asp) | |
| Ce1172_H1 | deletion of Gly459 | | |
| X2088_c9 | Val459 (Gly) | | |
| H086.8 | Asp459 (Gly) | Lys279 (Asn/Asp) | |

As shown in Table 9, above, 10 of 17 NIH45-46-resistant strains (5 of 7 NIH45-46$^{G54W}$-resistant strains) have amino acid variations at NIH45-46-contacting residues that have a fully conserved residue (shown in parenthesis) in all NIH45-46 sensitive strains. These mutations occur in the β23 strand immediately preceding V5 and in loop D. The positions of underlined sites have been shown to be important in resistance to VRC01 as reported in Li et al., 2011, *J. Virol.*, 85:8954-8967.

The largest difference between sensitivity to NIH45-46 and sensitivity to VRC01 was in strain 3016.v5.c45 (IC$_{50}$s of >30 and 0.16 μg/mL, respectively). The most notable residue in 3016.v5.c45 is Tyr282 in loop D. This large residue may alter the conformation of loop D, which is closely contacted by the four-residue insertion in the NIH45-46 CDRH3. The absence of the insertion may permit VRC01 to better accommodate an altered loop D. The next largest NIH45-46/VRC01 difference, for strain C2101.c1 (12.78 vs. 0.36 μg/mL), may similarly relate to the unusual Lys99$_{gp120}$ residue replacing the asparagine that favorably interacts with Arg99b$_{NIH45-46}$ in the NIH45-46-gp120 crystal structure.

From the neutralization assays, it is noted that NIH45-46$^{G54W}$ gained de novo neutralization activity against six NIH45-46 resistant strains, including the only three that were sensitive to VRC01 but resistant to NIH45-46 in the panel tested in Sheid et al, 2011, supra. For some strains that NIH45-46 neutralizes poorly, NIH45-46$^{G54W}$ was significantly more potent (e.g., improvements of >700-fold for T255-34 and 2000-fold for 3718.v3.c11). The enhanced neutralization activity of NIH45-46$^{G54W}$ implies that Trp54 forms a favorable hydrophobic interaction with Phe43 cavity of gp120 as seen in VRC03-gp120 (PDB 3SE8). NIH45-46$^{G54F}$ showed some increased activity (Tables 6, 7 and 8). Substituting Gly54 with tryptophan adds about 140 Å$^2$ of buried surface area on V$_H$ when complexed with gp120, and is consistent with the reduced dissociation rates observed in surface plasmon resonance (SPR) experiments (FIGS. 13a, 13B, and 13C). By providing a tryptophan in the Phe43 cavity of gp120, NIH45-46$^{G54W}$ may use higher affinities and/or slower dissociation rates to overcome incompatible surface variations that render some viruses less sensitive or resistant to its effects.

Heavy chain residue 54 is not conserved in HAADs; in addition to glycine (NIH45-46 and VRC01), residue 54 can be threonine (3BNC60, 3BNC117, 3BNC115; VRC-PG04), tyrosine (12A12), phenylalanine (12A21), or arginine (1B2530 and 1NC9), as reported in Sheid et al., 2011, supra; and Wu et al., 2011, supra. Tryptophan substitution in some HAADs was tested and shown in Table 10, below.

TABLE 10

| | | \multicolumn{8}{c}{In vitro neutralization IC$_{50}$ values (μg/mL)} |
| Virus | Clade | 3BNC60 WT | 3BNC60 T54W | 3BNC117 WT | 3BNC117 T54W | 3BNC55 WT | 3BNC55 T54W | 12A12 WT | 12A12 Y54W |
|---|---|---|---|---|---|---|---|---|---|
| SC422661.8 | B | 0.1 | 0.1 | 0.07 | 0.07 | 0.3 | 0.6 | 0.2 | 0.2 |
| AC10.0.29 | B | 13 | 3.1 | 6.5 | 2.8 | >50 | >50 | 0.6 | 0.5 |
| TRO.11 | B | 0.07 | 0.06 | 0.6 | 0.6 | 7.6 | >50 | 0.3 | 0.2 |
| Du172.17 | C | 0.05 | 0.04 | 0.04 | 0.9 | 2 | >50 | 0.2 | 0.1 |
| CAP210.2.00.E8 | C | 4.7 | 5.0 | 11 | 2.8 | >50 | >50 | >50 | >50 |
| CAP45.2.00.G3 | C | 10 | 19 | 16 | 23 | >50 | >50 | 0.4 | 0.2 |

Passive immunization and/or gene therapy to deliver HIV antibodies is increasingly being considered as an option for prevention of HIV infection. To reduce the concentrations and numbers of antibodies required for protection to realistic and affordable levels, highly potent and broadly neutralizing antibodies are the reagents of choice for passive delivery. Although it is difficult to compare the potencies and breadth of antibodies characterized using different virus panels, the natural form of NIH45-46 exhibits superior potency to VRC01 when compared against a panel of 82 Tier 2 and 3 viruses representing all known HIV clades (Sheid et al., 2011, supra). One set of HIV antibodies, the PGT antibodies that recognize the gp120 V3 loop and associated carbohydrates, exhibited median $IC_{50}$s up to 10-fold lower than VRCO1 (Walker et al., 2011, *Nature*, 477:466-471, the entire contents of which are incorporated herein by reference), but are less potent and broad than NIH45-46$^{G54W}$ (FIG. 15B, and Table 11, below).

TABLE 11

$IC_{50}$ from PGT antibodies and VRC01 using the same virus panel

| | Isolate | PGT-121 | PGT-122 | PGT-123 | PGT-125 | PGT-126 | PGT-127 | PGT-128 | PGT-130 | PGT-131 | PGT-135 | PGT-136 |
|---|---|---|---|---|---|---|---|---|---|---|---|---|
| Include >50 (µg/mL) | Geometric mean | 0.53 | 1.03 | 0.66 | 1.85 | 1.05 | 2.92 | 0.39 | 3.07 | 7.27 | 9.53 | 30.39 |
| | Arithmetic mean | 16.63 | 19.39 | 18.29 | 25.81 | 21.75 | 26.19 | 15.31 | 25.39 | 31.06 | 34.91 | 44.02 |
| | Median | 0.31 | 2.02 | 0.35 | 34.97 | 1.08 | 42.83 | 0.10 | 22.98 | 50.00 | 50.00 | 50.00 |
| Exclude >50 (µg/mL) | Geometric mean | 0.07 | 0.13 | 0.08 | 0.09 | 0.08 | 0.17 | 0.06 | 0.24 | 0.41 | 0.32 | 2.25 |
| | Arithmetic mean | 2.17 | 3.21 | 2.44 | 3.34 | 2.82 | 2.39 | 1.56 | 3.09 | 2.80 | 3.88 | 12.74 |
| | Median | 0.03 | 0.05 | 0.03 | 0.04 | 0.04 | 0.08 | 0.02 | 0.16 | 0.52 | 0.17 | 7.81 |
| | % viruses <50 (µg/mL) | 70% | 65% | 67% | 52% | 60% | 50% | 72% | 52% | 40% | 33% | 16% |

| | Isolate | PGT-137 | PGT-141 | PGT-142 | PGT-143 | PGT-144 | PGT-145 | VRC01 | VRC-PG04 | PG9 |
|---|---|---|---|---|---|---|---|---|---|---|
| Include >50 (µg/mL) | Geometric mean | 23.53 | 3.15 | 2.40 | 3.14 | 13.62 | 0.91 | 0.45 | 0.57 | 1.27 |
| | Arithmetic mean | 41.22 | 24.62 | 23.30 | 24.62 | 33.76 | 12.83 | 4.41 | 7.92 | 15.89 |
| | Median | 50.00 | 16.01 | 9.46 | 13.76 | 50.00 | 0.86 | 0.34 | 0.30 | 0.62 |
| Exclude >50 (µg/mL) | Geometric mean | 1.68 | 0.33 | 0.24 | 0.34 | 1.58 | 0.30 | 0.32 | 0.30 | 0.36 |
| | Arithmetic mean | 10.51 | 3.80 | 2.99 | 4.32 | 6.87 | 2.59 | 1.04 | 1.99 | 4.33 |
| | Median | 3.46 | 0.35 | 0.21 | 0.31 | 2.06 | 0.29 | 0.32 | 0.20 | 0.23 |
| | % viruses <50 (µg/mL) | 22% | 55% | 57% | 56% | 38% | 78% | 92% | 88% | 75% |

Table 11 above shows a comparison of mean and median $IC_{50}$ (µg/mL) values for PGT antibodies and VRCO1. A direct comparison between NIH45-46 and the PGT antibodies is not available. However, VRC01 (which was shown in a direct comparison to be less potent than NIH45-46) was directly compared to the PGT antibodies using the same virus panel. (Sheid et al., 2011, supra.) Mean $IC_{50}$ values were calculated using data taken from Sheid et al., 2011, supra. Geometric and arithmetic means were calculated to include data for all viral strains (listed as Include >50, in which case, values reported as $IC_{50}$>50 µg/mL were entered as 50 µg/mL in the calculation) and to exclude viral strains in which the $IC_{50}$ was >50 µg/mL (listed as Exclude >50, in which case the percent of viral strains with $IC_{50}$S <50 µg/mL is also reported). Mean $IC_{50}$S are compared with the median $IC_{50}$S as reported in Sheid et al., 2011, supra.

Figure 11B:
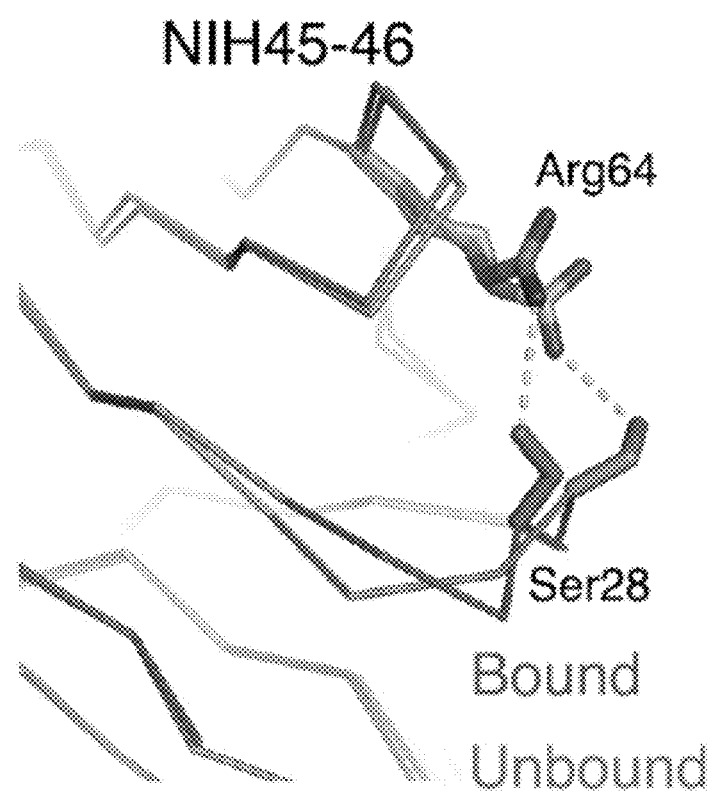
FIG. 11B is a superimposition of NIH45-46$_{LC}$ bound to gp120 (magenta) and unbound (green) showing the hydrogen bonds between Ser28 and Arg64, according to embodiments of the present invention.

Contacts between the antibody light chain and gp120 are mostly conserved between the NIH45-46-93TH057 and VRCO1-93THO57 structures with a notable exception: Ser28$_{NIH45-46\ LC}$ in CDRL1 replaces a solvent-exposed tyrosine (Tyr28$_{VRC01\ LC}$) that interacts with ordered N-linked carbohydrate attached to Asn276$_{93TH057}$. By contrast, the Ser28$_{NIH45-46\ LC}$ sidechain does not contact gp120 carbohydrates; instead it faces away from gp120, hydrogen bonding with Arg64$_{NIH45-46\ LC}$ (FWR3) and creating a 2.7 Å displacement of the main-chain Cα atoms (FIG. 11A). The Ser28$_{NIH45-46\ LC}$-Arg64$_{NIH45-46\ LC}$ interaction is maintained in unbound NIH45-46 (FIG. 11B). The position 28 substitution of serine for tyrosine largely accounts for the burial of more surface area in gp120's interaction with the VRC01 versus NIH45-46 light chain (681 A2 versus 395 A2 total buried surface area; 314 Å$^2$ versus 203 Å$^2$ buried surface area on the light chain) (Tables 5A, 5B). The larger contact area for the VRC01 light chain may account for the ability of VRC01, but not NIH45-46, to neutralize the clade C CAP45.2.00.G3 strain, given that the NIH45-46 heavy chain paired with the VRC01 light chain neutralizes this strain, whereas the VRC01 heavy chain paired with the NIH45-46 light chain does not (Table 12). However, the VRC01 light chain did not increase the potency of NIH45-46 against three other viral strains (Table 12), suggesting that the Tyr28 interaction with gp120 carbohydrate is not obligatory.

TABLE 12

In vitro neutralization $IC_{50}$ values (µg/mL)

| Virus | Clade | NIH45-46 | NIH45-46 HC VRC01 LC | VRC01 HC NIH45-46 LC | VRC01 |
|---|---|---|---|---|---|
| AC10.0.29 | B | 0.9 | 1.0 | 4.5 | 0.8 |
| TRO.11 | B | 1.9 | 0.3 | 24 | 0.5 |
| SC422661.8 | B | 0.05 | 0.2 | 0.4 | 0.2 |
| QH0692.42 | B | 0.7 | 0.9 | 1.2 | 0.7 |
| ZM214M.PL15.11 | C | 0.5 | 0.6 | 1.8 | 0.8 |
| CAP45.2.00.G3 | C | >50 | 2.1 | >50 | 1.8 |
| T257-31 | CRF02 (A/G) | 0.5 | 0.6 | 15 | 1.0 |

Example 3. Protein expression and purification. Proteins were produced and purified using previously-described methods (Diskin et al., 2010, *Nat. Struct. Mol. Biol.*, 17:608-613, the entire contents of which are incorporated herein by reference). Briefly, NIH45-46 IgG was expressed by transient transfection in HEK293-6E cells. Secreted IgG was purified from cell supernatants using protein A affinity chromatography (GE Healthcare). Fab fragments were prepared by digesting purified IgG with immobilized papain (Pierce) at 10 mg/mL and then separating Fabs from Fc-containing proteins using protein A chromatography and Superdex 200 16/60 size exclusion chromatography. For crystallization trials, the NIH45-46 Fab for crystallization experiments was concentrated to 11 mg/mL in 20 mM Tris pH 8.0, 150 mM sodium chloride, 0.02% sodium azide (TBS). Substitutions in heavy chain residue 54 of NIH45-46, 3BNC55, 12A12, 3BNC117 and 3BNC60 were introduced using a Quikchange II kit (Agilent technologies). Wild type, mutant forms and chain swapped versions of these proteins were expressed as IgGs in HEK293-6E cells and purified by protein A chromatography as described for NIH45-46 IgG. Proteins were stored at a concentration of 1 mg/mL for neutralization assays in either 10 mM sodium citrate pH 3.05, 50 mM sodium chloride, 0.02% sodium azide or in TBS (12A12 and 12A12$^{Y54W}$) or in phosphate buffered saline (NIH45-46 mutated/truncated in CDRH3 and NIH45-46/VRC01 heavy and light chain swapped antibodies (Abs)) prior to dilution into neutral pH cell media. For SPR analyses, NIH45-46 and NIH45-46$^{G54W}$ heavy chains were subcloned into the pTT5 (NRC-BRI) expression vector to encode C-terminal 6x-His tagged Fab heavy chains ($V_H$—CH1-6x-His tag), and the heavy chain expression vectors were co-transfected with the appropriate light chain vector into HEK293-6E cells. Supernatants were collected after 7 days, buffer exchanged into TBS and loaded on a $Ni^{2+}$-NTA affinity column (Qiagen). Fabs were eluted using TBS supplemented with 250 mM imidazole and further purified by Superdex200 10/300 size exclusion chromatography (GE Healthcare) in TBS.

Genes encoding truncated 93TH053, CAP244.2.00.D3, and Q259.d2.17 gp120 cores including the deletions and modifications described in Zhou et al., 2010, supra (the entire contents of which are incorporated herein by reference), were chemically synthesized (BlueHeron). An extra disulfide bond was introduced into 93TH053 by changing the Val65 and Ser115 codons into cysteines.

The modified core genes were subcloned into the pACgp67b expression vector (BD Biosynthesis) to include a C-terminal 6x-His tag, expressed in baculovirus-infected insect cells, and purified from insect cell supernatants as previously described in Diskin et al., 2010, supra. For crystallization experiments, purified NIH45-46 Fab and 93TH057 gp120 were incubated at a 1:1 molar ratio and treated with 40 kU of Endoglycosidase H (New England Biolabs) for 16 hours at 37° C. The complex was purified after the incubation by Superdex 200 10/300 size exclusion chromatography (GE Healthcare) and then concentrated to $OD_{280}$=9.6 in 20 mM Tris pH 8.0, 300 mM sodium chloride, 0.02% sodium azide.

Example 4. Crystallization. Crystallization screening was done by vapor diffusion in sitting drops by a Mosquito® crystallization robot (TTP labs) using 400 nL drops (1:1 protein to reservoir ratio) utilizing commercially available crystallization screens (Hampton). Initial crystallization hits for Fab NIH45-46 and for NIH45-46-93TH057 complex were identified using the PEGRx HT™ (Hampton) screen and then manually optimized. Thin needle-like crystals of Fab NIH45-46 (space group $P2_12_12_1$, a=49.4 Å, b=87.4 Å, c=166.4 Å; one molecule per asymmetric unit) were obtained upon mixing a protein solution at 11 mg/mL with 12% polyethylene glycol 20,000, 0.1 M sodium acetate pH 5.0, 0.1 M sodium/potassium tartrate, 0.02 M ammonium sulfate at 20° C. Crystals were briefly soaked in mother liquor solution supplemented with 15% and then 30% glycerol before flash cooling in liquid nitrogen. Crystals of the NIH45-46-93TH057 complex (space group $P2_12_12_1$, a=69.1 Å, b=70.5 Å, c=217.7 Å; one molecule per asymmetric unit) were obtained upon mixing a protein solution at $OD_{280}$=9.6 with 12% isopropanol, 10% polyethylene glycol 10,000, 0.1 M sodium citrate pH 5.0 at 20° C. Complex crystals were cryo-cooled by covering the crystallization drops with paraffin oil to prevent evaporation and then adding an excess of 20% isopropanol, 5% glycerol, 10% polyethylene glycol, 0.1 M sodium citrate pH 5.0 to the drops prior to mounting and flash cooling the crystals in liquid nitrogen.

Example 5. Data collection, structure solution and refinement. X-ray diffraction data were collected at the Stanford Synchrotron Radiation Lightsource (SSRL) beamline 12-2 using a Pilatus 6M pixel detector (Dectris). The data were indexed, integrated and scaled using XDS as described in Kabsch, 2010, *Acta Crystallogr D Biol Crystallogr*, 66:125-132, the entire contents of which are incorporated herein by reference. The Fab NIH45-46 structure was solved by molecular replacement using Phaser as described in McCoy et al., 2007, *J. Appl. Cryst.*, 40:658-674, the entire contents of which are incorporated herein by reference, and the $V_H V_L$ and $C_H 1 C_L$ domains of the VRC01 Fab (PDB code 3NGB) as separate search models. The model was refined to 2.6 Å resolution using an iterative approach involving refinement using the Phenix crystallography package Adams et al., 2010, *Acta Crystallogr D Biol Crystallogr*, 66:213-221, the entire contents of which are incorporated herein by reference, and manually fitting models into electron density maps using Coot (Emsley et al., 2004, *Acta Crystallogr D Biol Crystallogr*, 60:2126-2132, the entire contents of which are incorporated herein by reference). The final model ($R_{work}$=18.4%; $R_{free}$=23.8%) includes 3380 protein atoms, 125 water molecules and 37 ligand atoms, including N-Acetylglucosamine, glycerol and a sulfate ion (FIG. 2). 96.5%, 3.3% and 0.2% of the residues were in the favored, allowed and disallowed regions, respectively, of the Ramachandran plot. The first glutamine of the NIH-145-46 heavy chain was modeled as 5-pyrrolidone-2-carboxylic acid.

A search model for solving the NIH45-46-93TH057 complex was created by superimposing the refined structure of the NIH45-46 Fab on the VRC01 Fab in the structure of VRC01-93TH057 (PDB code 3NGB). A molecular replacement solution was found as described above using separate search models for the $V_H V_L$ domains of NIH45-46 complexed with 93TH057 and the $C_H 1 C_L$ domains of NIH45-46. (FIG. 2). The complex structure was refined to 2.45 Å resolution as described for the Fab structure. To reduce model bias, the CDRH3 of NIH45-46 was omitted from the model and then built into electron density maps after a few rounds of refinement. The final model ($R_{work}$=20.7%; $R_{free}$=25.6%) includes 5989 protein atoms, 67 water molecules and 148 atoms of carbohydrates, citrate and chloride ions (FIG. 2). 96.1%, 3.5% and 0.4% of the residues were in the favored, allowed and disallowed regions, respectively, of the Ramachandran plot. Disordered residues that were not included in the model were residues 1-2 of the NIH45-46 light chain, residues 133-136 and 219-221 of the heavy chain, and residues 302-308 (V3 substitution), residues 397-408 (a total of 6 residues from V4) and the 6×-His tag of 93TH057. The first glutamine of the NIH45-46 heavy chain was modeled as 5-pyrrolidone-2-carboxylic acid.

Buried surface areas were calculated using AreaIMol in CCP4 and a 1.4 Å probe. Superimposition calculations were done and molecular representations were generated using PyMol (The PyMOL Molecular Graphics System, Schrödinger, LLC).

Example 6. Surface Plasmon Resonance (SPR) measurements. The binding of gp120 core proteins to wild-type NIH45-46 Fab and to mutant (NIH45-46$^{G54W}$) Fab was compared using a Biacore T100 instrument (GE Healthcare). Purified NIH45-46 and NIH45-46$^{G54W}$ Fabs were immobilized at coupling densities of 500 resonance units (RU) or 1500 RU on a CM5 sensor chip (Biacore) in 10 mM acetate pH 5.0 using primary amine coupling chemistry as described in the Biacore manual. One of the four flow cells on each sensor chip was mock-coupled using buffer to serve as a blank. Experiments were performed at 25° C. in 20 mM HEPES, pH 7.0, 150 mM sodium chloride and 0.005% (v/v) surfactant P20, and the sensor chips were regenerated using 10 mM glycine, pH 2.5. gp120 core proteins were injected in a two-fold dilution series at concentrations ranging from 500 nM to 31.2 nM at a flow rate of 70 μL/min. After subtracting the signal from the mock-coupled flow cell, kinetic data were globally fit to a 1:1 binding model (Biacore evaluation software) to derive on- and off-rate constants, which were used to calculate affinities as $K_D$ $k_d/k_a$.

Example 7. In vitro neutralization assays. A previously-described pseudovirus neutralization assay was used to compare the neutralization potencies of wild-type and mutant IgGs as previously described in Montefiori, 2005, Current protocols in immunology, Edited by John E. Coligan et al., Chapter 12, Unit 12.11, the entire contents of which are incorporated herein by reference. Briefly, pseudoviruses were generated in HEK293T cells by co-transfection of an Env-expressing vector and a replication-incompetent backbone plasmid. Neutralization was assessed by measuring the reduction in luciferase reporter gene expression in the presence of a potential inhibitor following a single round of pseudovirus infection in TZM-b1 cells. Antibodies were pre-incubated with 250 infectious viral units in a three or four-fold dilution series for one hour at 37° C. before adding 10,000 TZM-b1 cells per well for a two-day incubation. Cells were then lysed and luciferase expression was measured using BrightGlo (Promega) and a Victor3 luminometer (PerkinElmer). Nonlinear regression analysis using the program Prism (GraphPad) was used to calculate the concentrations at which half-maximal inhibition was observed ($IC_{50}$ values) as described in Klein et al., 2009, *PNAS*, 106:7385-7390, the entire contents of which are incorporated herein by reference. Samples were initially screened in duplicates. Reagents that showed enhanced activity were tested again as triplicates. Values for NIH45-46 and NIH45-46$^{G54W}$ in FIG. 14 were obtained from three independent experiments. Similar $IC_{50}$ values were obtained in two independent neutralization experiments using different dilution series.

Example 8. Signature Features of PVL Antibodies. The correlation between neutralization potency and the length of two of the light chain CDR loops was analyzed in CD4bs antibodies. The relatively small CDRL1 of VRC01, which has a 2-residue deletion relative to its germline precursor, was previously correlated with increased neutralization potency (Zhou et al., 2010, supra). It was noted that sequences of VRC01, NIH45-46, and VRC-PG04 revealed a more striking correlation for the length of CDRL3, which is only 5 residues in these antibodies. Examination of the large Abysis database for human Ab sequences (http://www.bioinf.org.uk/abs/) showed that only about 1% of $V_L$ domains have a CDRL3 length of 5 amino acids, compared with more typical 9-11 residue lengths. Larger CDRL3 loops would place critical side chains at the tip of CDRL3 in different locations, thus not able to interact with gp120 in the same manner. In antibodies with longer CDRL3s, the tip of CDRL3 interacts with Trp47$_{HC}$, a highly conserved residue (found in 63 of 69 germline $V_H$ gene segments) that plays a similar role as Trp102$_{HC}$ in the Abs with 5-residue CDRL3s to stabilize the $V_H$-$V_L$ interface.

V domain alignments revealed the following sequence characteristics of the most potent of the VRC01-like Abs: complete conservation of heavy chain Arg71$_{HC}$, Trp50$_{HC}$, Asn58$_{HC}$, and Trp102$_{HC}$, and light chain Glu90$_{LC}$, Trp65$_{LC}$/Phe65$_{LC}$ and a CDRL3 length of exactly 5 amino acids (residues are numbered here as in the structure of NIH45-46; pdb code 3U7Y). Analysis of the per residue variability of VH1-2*02-derived Abs indicates that the conservation of Trp50$_{HC}$ and Asn58$_{HC}$ is unlikely to be coincidental.

Figure 16:
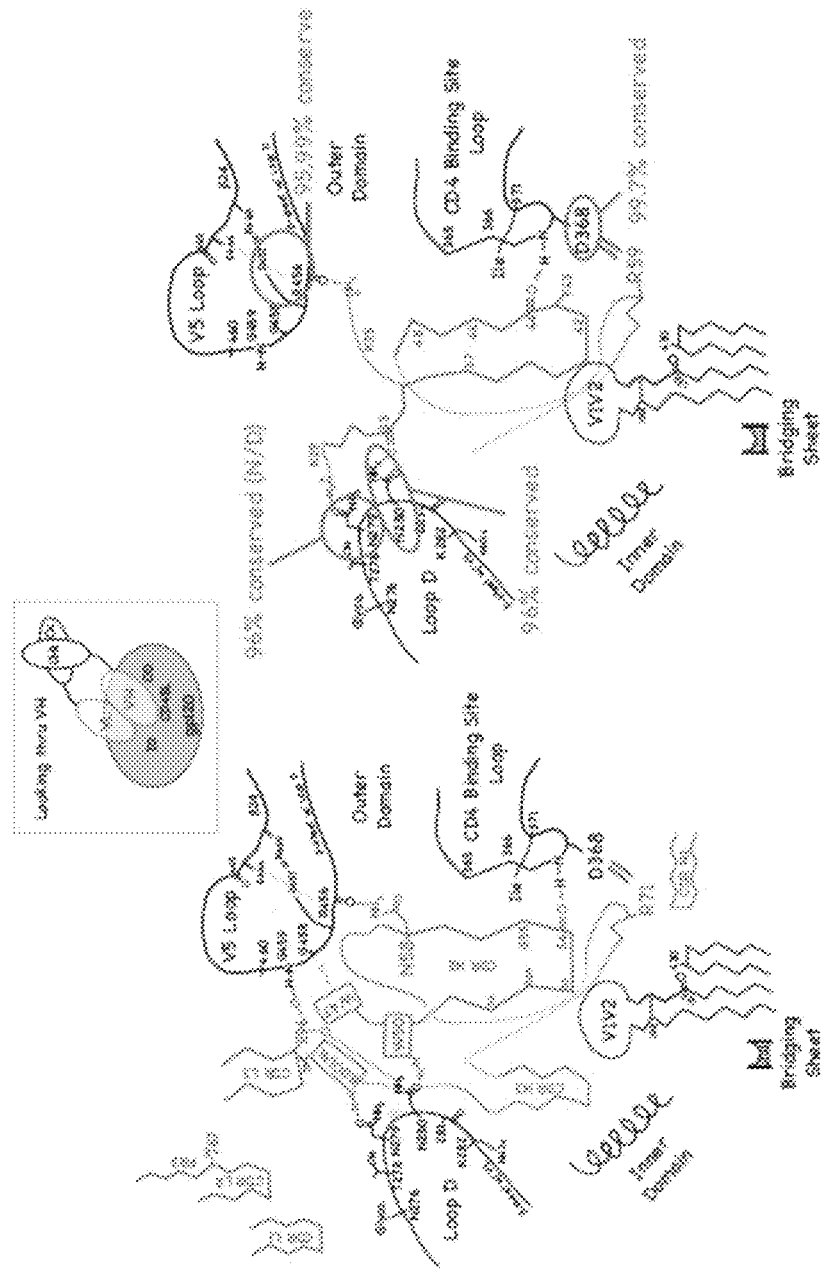
FIG. 16 is a schematic illustration of, on the left: PVL antibody interactions (magenta and blue-gray) made with gp120 (black); and on the right: CD4 (magenta) with gp120 (black), with the viewpoint of the diagram shown in the inset box, according to embodiments of the present invention.

The roles that conserved residues play in the $V_H$ domain structure and in binding to the CD4bs on gp120 are shown schematically in FIG. 16 and Table 13, below. The figures are based on interactions present in the gp120 complexes of VRC01, NIH45-46, and VRC-PG04 (Wu et al., 2011, *Science*, 333:1593-1602; Diskin et al., 2011, *Science*, 334:1289-1293; and Zhou et al., 2010, *Science*, 329:811-817, the entire contents of all of which are incorporated herein by reference.

TABLE 13

PVL Features

| PVL Characteristic feature | Role |
|---|---|
| Trp50$_{HC}$ | H bond with Asn280$_{gp120}$ |
| Asn58$_{HC}$ | H bond with Arg456$_{gp120}$ |
| Arg71$_{HC}$ | H bond/salt bridge with Asp368$_{gp120}$ |
| Trp102*$_{HC}$ | H bond with Asn/Asp279$_{gp120}$ |
| Glu90**$_{LC}$ | H bond with Gly459$_{gp120}$ |
| Trp65***$_{LC}$/Phe65***$_{LC}$ | interaction with Asn276$_{gp120}$ glycan |
| 5-residue CDRL3 | prevent steric clashes, position 89$_{LC}$ & 90$_{LC}$ side chains |

*Position Trp100B;
**Postion Glu96; and
***Trp67/Phe67 using Kabat numbering system.

The side chains of Trp50$_{HC}$, Trp102$_{HC}$, and Trp47$_{HC}$ form an unusual propeller-like arrangement on the surface the V$_H$ domain. (Although Trp47$_{HC}$ participates in the "propeller," it is not considered to be a signature residue of potent CD4bs antibodies because it is commonly found in V$_H$ domains.) The main interactions of the characteristic V$_H$ domain residues with gp120 are as follows: Trp50$_{HC}$: indole N—H hydrogen bonds with the side chain oxygen of Asn280$_{gp120}$; Asn58$_{HC}$: side chain N—H hydrogen bonds with the backbone carbonyl of Arg456$_{gp120}$; Arg71$_{HC}$: side chain hydrogen bonds/salt bridges with the side chain of Asp368$_{gp120}$; and Trp102$_{HC}$: indole N—H hydrogen bonds with the side chain oxygen of Asn/Asp279$_{gp120}$. Trp102$_{HC}$ also buries 85 Å$^2$ of surface area at the V$_H$/V$_L$ interface—contacting residues Tyr89$_{LC}$ and Glu90$_{LC}$.

In the light chains, the side chain of Glu90$_{LC}$ forms a hydrogen bond with the backbone nitrogen of Gly459$_{gp120}$ and/or the side chain of Asn280$_{gp120}$. The conservation of Trp65$_{LC}$/Phe65$_{LC}$ is surprising as this position is distant from gp120 in the available crystal structures.

For those interactions that depend on specific gp120 side chains, the degree of conservation of the relevant gp120 residues is 96.4% for Asn/Asp279$_{gp120}$, 96.4% for Asn280$_{gp120}$, and 99.7% for Asp368$_{gp120}$ (based on the 2010 filtered web alignment of 2869 HIV-1 sequences in the Los Alamos HIV database; http://www.hiv.lanl.gov/). Arg456$_{gp120}$, which is involved in a main-chain hydrogen bond with the sidechain of Asn58$_{HC}$, is also highly conserved (95.0%).

An SPR-based binding assay demonstrated detectable binding of the germline heavy chain/mature light chain IgG to immobilized gp140 trimers. Binding of germline heavy chain IgGs was analyzed with substitutions in the four signature heavy chain residues (W50S, N58S, R71T, and W102S) (again paired with the mature 3BNC60 light chain). The W50S, R71T, and W102S mutants showed little or no gp140 binding, and the N58S mutation diminished binding by about 20-fold, consistent with the corresponding PVL characteristic residues playing key roles in recognition of the HIV-1 envelope spike by the germline PVL B cell receptor.

To examine the importance of the signature PVL residues to their activity, the gp120 sequences of HIV-1 strains resistant to neutralization by NIH45-46 were analyzed. The gp120 residue variants associated with resistance were identified by three criteria: first, they are contact residues with NIH45-46; second, they are absent in NIH45-46-resistant viruses; third, they do not appear in NIH45-46-sensitive viruses. The critical positions identified were 279$_{gp120}$, 280$_{gp120}$, 456$_{gp120}$, 458$_{gp120}$, and 459$_{gp120}$; the common (i.e., sensitive) residues at these positions are Asx, Asn, Arg, Gly, and Gly, respectively, where Asx is Asp or Asn. These sites make significant contacts with the characteristic PVL residues (FIG. 16). Viral stains with variations at these sites are generally neutralized poorly by all PVL antibodies, as expected if substitutions at these positions interfere with common interactions.

Figure 17:
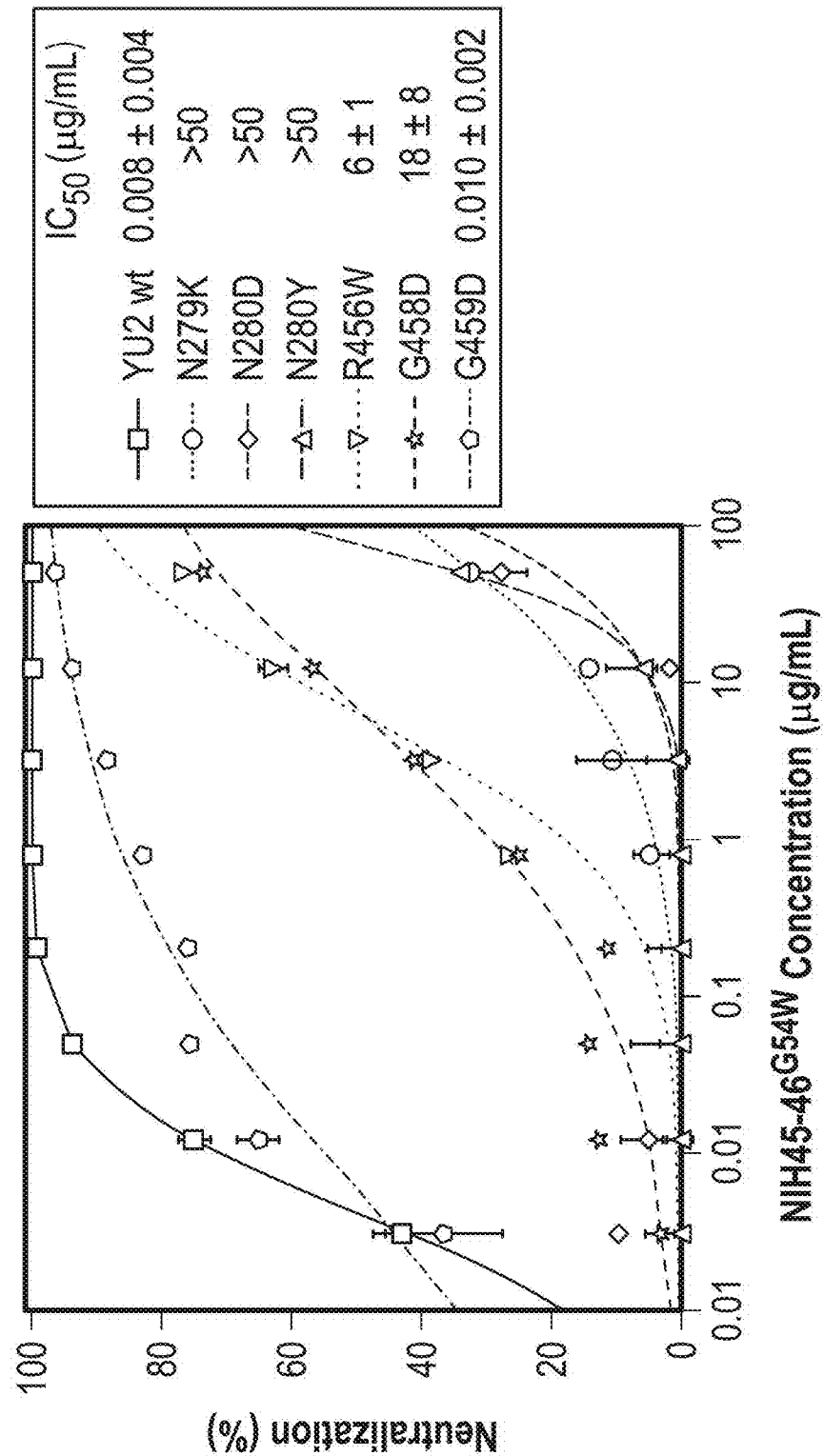
FIG. 17 is a graph of a neutralization assay showing the effects of mutations at critical residues in YU2 gp120 on neutralization by PVL antibody NIH45-46$^{G54W}$ in which the IC$_{50}$ values are the mean of several independent experiments, and the graph shows one experiment, according to embodiments of the present invention.

To verify the significance of gp120 variations at these positions, point mutants within the gp160 gene of HIV-1 strain YU2 were engineered, created pseudoviruses carrying the mutant gp160s, and determined the neutralization potencies of the PVL NIH45-46$^{G54W}$ (Diskin et al., 2011, supra) (as characterized by IC$_{50}$ values). Mutations at 279$_{gp120}$ and 280$_{gp120}$ rendered the virus resistant to neutralization by NIH45-46$^{G54W}$, and substitution of 458$_{gp120}$ diminished the neutralization potency by >1500-fold (FIG. 17).

As disclosed throughout and evidenced by, for example, the neutralization assays of FIG. 14, a PVL antibody such as NIH45-46, having a hydrophobic amino acid (Trp) substituted at the Phe43$_{CD4}$-equivalent residue (position 54) has increased potency and breadth in HIV strains. Furthermore, methods are provided for identifying a PVL antibody and the Phe43$_{CD4}$-equivalent residue for substitution with a hydrophobic amino acid.

While the present invention has been illustrated and described with reference to certain exemplary embodiments, those of ordinary skill in the art will understand that various modifications and changes may be made to the described embodiments without departing from the spirit and scope of the present invention, as defined in the following claims.

SEQUENCE LISTING

```
Sequence total quantity: 90
SEQ ID NO: 1            moltype = AA  length = 104
FEATURE                 Location/Qualifiers
source                  1..104
                        mol_type = protein
                        organism = Homo sapiens
SEQUENCE: 1
EIVLTQSPGT LSLSPGETAI ISCRTSQYGS LAWYQQRPGQ APRLVIYSGS TRAAGIPDRF   60
SGSRWGPDYN LTISNLESGD FGVYYCQQYE FFGQGTKVQV DIKR                   104

SEQ ID NO: 2            moltype = AA  length = 121
FEATURE                 Location/Qualifiers
source                  1..121
                        mol_type = protein
```

```
                                organism = Homo sapiens
SEQUENCE: 2
QVQLVQSGGQ MKKPGESMRI SCRASGYEFI DCTLNWIRLA PGKRPEWMGW LKPRGGAVNY      60
ARPLQGRVTM TRDVYSDTAF LELRSLTVDD TAVYFCTRGK NCDYNWDFEH WGRGTPVIVS     120
S                                                                    121

SEQ ID NO: 3            moltype = AA   length = 104
FEATURE                 Location/Qualifiers
source                  1..104
                        mol_type = protein
                        organism = Homo sapiens
SEQUENCE: 3
EIVLTQSPGT LSLSPGETAI ISCRTSQYGS LAWYQQRPGQ APRLVIYSGS TRAAGIPDRF      60
SGSRWGPDYN LTIRNLESGD FGLYYCQQYE FFGQGTKVQV DIKR                     104

SEQ ID NO: 4            moltype = AA   length = 121
FEATURE                 Location/Qualifiers
source                  1..121
                        mol_type = protein
                        organism = Homo sapiens
SEQUENCE: 4
QVQLVQSGGQ MKKPGESMRI SCQASGYEFI DCTLNWVRLA PGRRPEWMGW LKPRGGAVNY      60
ARPLQGRVTM TRDVYSDTAF LELRSLTADD TAVYYCTRGK NCDYNWDFEH WGRGTPVTVS     120
S                                                                    121

SEQ ID NO: 5            moltype = AA   length = 107
FEATURE                 Location/Qualifiers
source                  1..107
                        mol_type = protein
                        organism = Homo sapiens
SEQUENCE: 5
EIVLTQSPAT LSLSPGETAI ISCRTSQSGS LAWYQQRPGQ APRLVIYSGS TRAAGIPDRF      60
SGSRWGADYN LSISNLESGD FGVYYCQQYE FFGQGTKVQV DIKRTVA                  107

SEQ ID NO: 6            moltype = AA   length = 125
FEATURE                 Location/Qualifiers
source                  1..125
                        mol_type = protein
                        organism = Homo sapiens
SEQUENCE: 6
QVRLSQSGGQ MKKPGESMRL SCRASGYEFL NCPINWIRLA PGRRPEWMGW LKPRGGAVNY      60
ARKFQGRVTM TRDVYSDTAF LELRSLTSDD TAVYFCTRGK YCTARDYYNW DFEHWGRGAP     120
VTVSS                                                                125

SEQ ID NO: 7            moltype = AA   length = 103
FEATURE                 Location/Qualifiers
source                  1..103
                        mol_type = protein
                        organism = Homo sapiens
SEQUENCE: 7
DIQMTQSPSS LSARVGDTVT ITCQANGYLN WYQQRRGKAP KLLIYDGSKL ERGVPARFSG      60
RRWGQEYNLT INNLQPEDVA TYFCQVYEFI VPGTRLDLKR TVA                      103

SEQ ID NO: 8            moltype = AA   length = 123
FEATURE                 Location/Qualifiers
source                  1..123
                        mol_type = protein
                        organism = Homo sapiens
SEQUENCE: 8
QVHLSQSGAA VTKPGASVRV SCEASGYKIS DHFIHWWRQA PGQGLQWVGW INPKTGQPNN      60
PRQFQGRVSL TRQASWDFDT YSFYMDLKAV RSDDTAIYFC ARQRSDFWDF DVWGSGTQVT     120
VSS                                                                  123

SEQ ID NO: 9            moltype = AA   length = 103
FEATURE                 Location/Qualifiers
source                  1..103
                        mol_type = protein
                        organism = Homo sapiens
SEQUENCE: 9
DIQMTQSPSS LSASVGDTVT ITCQANGYLN WYQQRRGKAP KLLIYDGSKL ERGVPSRFSG      60
RRWGQEYNLT INNLQPEDIA TYFCQVYEFV VPGTRLDLKR TVA                      103

SEQ ID NO: 10           moltype = AA   length = 123
FEATURE                 Location/Qualifiers
source                  1..123
                        mol_type = protein
                        organism = Homo sapiens
SEQUENCE: 10
QVQLLQSGAA VTKPGASVRV SCEASGYNIR DYFIHWWRQA PGQGLQWVGW INPKTGQPNN      60
```

```
PRQFQGRVSL TRHASWDFDT FSFYMDLKAL RSDDTAVYFC ARQRSDYWDF DVWGSGTQVT    120
VSS                                                                 123

SEQ ID NO: 11           moltype = AA   length = 103
FEATURE                 Location/Qualifiers
source                  1..103
                        mol_type = protein
                        organism = Homo sapiens
SEQUENCE: 11
DIQMTQSPSS LSARVGDTVT ITCQANGYLN WYQQRRGKAP KLLIYDGSKL ETGVPSRFTG    60
RRWGQEYNLT INNLQPEDIA TYFCQVYEFI VPGTRLDLKR TVA                     103

SEQ ID NO: 12           moltype = AA   length = 123
FEATURE                 Location/Qualifiers
source                  1..123
                        mol_type = protein
                        organism = Homo sapiens
SEQUENCE: 12
QVRLLQSGAA VTKPGASVRV SCEASGYEIR DYFIHWWRQA PGQGLQWVGW INPKTGQPNN    60
PRQFQGRVSL TRQASWDFDS YSFYMDLKAL RSDDTGVYFC ARQRSDYWDF DVWGSGTQVT    120
VSS                                                                 123

SEQ ID NO: 13           moltype = AA   length = 103
FEATURE                 Location/Qualifiers
source                  1..103
                        mol_type = protein
                        organism = Homo sapiens
SEQUENCE: 13
DIQMTQSPSS LSASVGDTVT ITCQANGYLN WYQQRRGKAP KLLIYDGSKL ERGVPSRFSG    60
RRWGQEYNLT INNLQPEDIA TYFCQVYEFI VPGTRLDLKR TVA                     103

SEQ ID NO: 14           moltype = AA   length = 123
FEATURE                 Location/Qualifiers
source                  1..123
                        mol_type = protein
                        organism = Homo sapiens
SEQUENCE: 14
QVQLLQSGAA VTKPGASVRV SCEASGYNIR DYFIHWWRQA PGQGLQWVGW INPKTGQPNN    60
PRLFQGRVSL TRHASWDFDT FSFYMDLKAV RSDDTAVYFC ARQRSDYWDF DVWGSGTQVT    120
VSS                                                                 123

SEQ ID NO: 15           moltype = AA   length = 103
FEATURE                 Location/Qualifiers
source                  1..103
                        mol_type = protein
                        organism = Homo sapiens
SEQUENCE: 15
DIQMTQSPSS LSASVGDTVT ITCQANGYLN WYQQRRGKAP KLLIYDGSKL ERGVPSRFSG    60
RRWGQEYNLT INNLQAEDIA TYFCQVYEFA VPGTRLDLKR TVA                     103

SEQ ID NO: 16           moltype = AA   length = 123
FEATURE                 Location/Qualifiers
source                  1..123
                        mol_type = protein
                        organism = Homo sapiens
SEQUENCE: 16
QVQLLQSGAA VTKPGASVRV SCEASGYNIR DYFIHWWRQA PGQGLQWVGW INPKTGQPNN    60
PRQFQGRVSL TRHASWDFDT FSFYMDLKGL RSDDTAIYFC ARQRSDYWDF DVWGSGTQVT    120
VSS                                                                 123

SEQ ID NO: 17           moltype = AA   length = 107
FEATURE                 Location/Qualifiers
source                  1..107
                        mol_type = protein
                        organism = Homo sapiens
SEQUENCE: 17
DIQMTQSPSS LSASVGDRVT ITCQAGQGIG SSLQWYQQKP GKAPKLLVHG ASNLHRGVPS    60
RFSGSGFHTT FSLTISGLQR DDFATYFCAV LEFFGPGTKV EIKRTVA                 107

SEQ ID NO: 18           moltype = AA   length = 122
FEATURE                 Location/Qualifiers
source                  1..122
                        mol_type = protein
                        organism = Homo sapiens
SEQUENCE: 18
SQHLVQSGTQ VKKPGASVRI SCQASGYSFT DYVLHWWRQA PGQGLEWMGW IKPVYGARNY    60
ARRFQGRINF DRDIYREIAF MDLSGLRSDD TALYFCARDG SGDDTSWHLD PWGQGTLVIV    120
SA                                                                  122
```

```
SEQ ID NO: 19              moltype = AA   length = 102
FEATURE                    Location/Qualifiers
source                     1..102
                           mol_type = protein
                           organism = Homo sapiens
SEQUENCE: 19
EIVLTQSPGT LSLSPGETAS LSCTAASYGH MTWYQKKPGQ PPKLLIFATS KRASGIPDRF   60
SGSQFGKQYT LTITRMEPED FARYYCQQLE FFGQGTRLEI RR                     102

SEQ ID NO: 20              moltype = AA   length = 125
FEATURE                    Location/Qualifiers
source                     1..125
                           mol_type = protein
                           organism = Homo sapiens
SEQUENCE: 20
QVQLVQSGSG VKKPGASVRV SCWTSEDIFE RTELIHWVRQ APGQGLEWIG WVKTVTGAVN   60
FGSPDFRQRV SLTRDRDLFT AHMDIRGLTQ GDTATYFCAR QKFYTGGQGW YFDLWGRGTL   120
IVVSS                                                              125

SEQ ID NO: 21              moltype = AA   length = 103
FEATURE                    Location/Qualifiers
source                     1..103
                           mol_type = protein
                           organism = Homo sapiens
SEQUENCE: 21
DIQMTQSPSS LSASLGDRVT ITCQASRGIG KDLNWYQQKP GKAPKLLVSD ASILEGGVPS   60
RFSGSGFHQN FSLTISSLQP EDVATYFCQQ YETFGQGTKV DIK                    103

SEQ ID NO: 22              moltype = AA   length = 131
FEATURE                    Location/Qualifiers
source                     1..131
                           mol_type = protein
                           organism = Homo sapiens
SEQUENCE: 22
QVQLVQSGAA VRKPGASVTV SCKFAEDDDY SPHWVNPAPE HYIHFLRQAP GQQLEWLAWM   60
NPTNGAVNYA WQLHGRLTAT RDGSMTTAFL EVRSLRSDDT AVYYCARAQK RGRSEWAYAH   120
WGQGTPVLVS S                                                       131

SEQ ID NO: 23              moltype = AA   length = 103
FEATURE                    Location/Qualifiers
source                     1..103
                           mol_type = protein
                           organism = Homo sapiens
SEQUENCE: 23
DIQMTQSPSS LSASLGDRVT ITCQASRGIG KDLNWYQQKA GKAPKLLVSD ASTLEGGVPS   60
RFSGSGFHQN FSLTISSLQA EDVATYFCQQ YETFGQGTKV DIK                    103

SEQ ID NO: 24              moltype = AA   length = 131
FEATURE                    Location/Qualifiers
source                     1..131
                           mol_type = protein
                           organism = Homo sapiens
SEQUENCE: 24
QVQLVQSGAA VRKPGASVTV SCKFAEDDDY SPYWVNPAPE HFIHFLRQAP GQQLEWLAWM   60
NPTNGAVNYA WYLNGRVTAT RDRSMTTAFL EVKSLRSDDT AVYYCARAQK RGRSEWAYAH   120
WGQGTPVVVS S                                                       131

SEQ ID NO: 25              moltype = AA   length = 103
FEATURE                    Location/Qualifiers
source                     1..103
                           mol_type = protein
                           organism = Homo sapiens
SEQUENCE: 25
DIQMTQSPSS LSASLGDRVT ITCQASRGIG KDLNWYQQKP GRAPKLLVSD ASILEGGVPT   60
RFSGSGFHQN FSLTISSLQA EDVATYFCQQ YETFGQGTKV DIK                    103

SEQ ID NO: 26              moltype = AA   length = 131
FEATURE                    Location/Qualifiers
source                     1..131
                           mol_type = protein
                           organism = Homo sapiens
SEQUENCE: 26
QVQLVQSGAA VRKPGASVTV SCKFAEDDDF SPHWVNPAPE HYIHFLRQAP GQQLEWLAWM   60
KPTNGAVNYA WQLQGRVTVT RDRSQTTAFL EVKNLRSDDT AVYYCARAQK RGRSEWAYAH   120
WGQGTPVVIS A                                                       131

SEQ ID NO: 27              moltype = AA   length = 103
FEATURE                    Location/Qualifiers
source                     1..103
```

```
                         mol_type = protein
                         organism = Homo sapiens
SEQUENCE: 27
DIQMTQSPSS LSASLGDRVT ITCQASRGIG KDLNWYQQKR GRAPRLLVSD ASVLEGGVPS    60
RFSGSGFHQN FSLTISTLQP EDVATYFCQQ YETFGQGTKV DIK                     103

SEQ ID NO: 28            moltype = AA   length = 131
FEATURE                  Location/Qualifiers
source                   1..131
                         mol_type = protein
                         organism = Homo sapiens
SEQUENCE: 28
QVQLVQSGAA VRKPGASISV SCKFADADDY SPHWMNPAPE HYIHFLRQAP GQQLEWLAWM    60
NPTNGAVNYA WYLNGRVTAT RDRSMTTAFL EVRSLRSDDT AVYYCARAQK RARSEWAYAH   120
WGQGTPVVVS S                                                        131

SEQ ID NO: 29            moltype = AA   length = 103
FEATURE                  Location/Qualifiers
source                   1..103
                         mol_type = protein
                         organism = Homo sapiens
SEQUENCE: 29
DIQMTQSPSS LSASLGDRVT ITCQASRGIG KDLNWYQQKA GKAPKLLVSD ASILEGGVPS    60
RFSGSGFHQN FSLTISSLQP EDVATYFCQQ YETFGQGTKV DIK                     103

SEQ ID NO: 30            moltype = AA   length = 131
FEATURE                  Location/Qualifiers
source                   1..131
                         mol_type = protein
                         organism = Homo sapiens
SEQUENCE: 30
QVQLVQSGAA VRKPGASVTV SCKFAEDDDW SPHWVNPAPE HYIHFLRQAP GQQLEWLAWM    60
NPTNGAVNYA WQLNGRLTAT RDTSMTTAFL EVKSLRSDDT AVYYCARAQK RGRSEWAYAH   120
WGQGTPVVVS S                                                        131

SEQ ID NO: 31            moltype = AA   length = 103
FEATURE                  Location/Qualifiers
source                   1..103
                         mol_type = protein
                         organism = Homo sapiens
SEQUENCE: 31
EIVLTQSPGI LSLSPGETAT LFCKASQGGN AMTWYQKRRG QVPRLLIYDT SRRASGVPDR    60
FVGSGSGTDF FLTINKLDRE DFAVYYCQQF EFFGLGSELE VHR                     103

SEQ ID NO: 32            moltype = AA   length = 130
FEATURE                  Location/Qualifiers
source                   1..130
                         mol_type = protein
                         organism = Homo sapiens
SEQUENCE: 32
QVQLVQSGAV IKTPGSSVKI SCRASGYNFR DYSIHWVRLI PDKGFEWIGW IKPLWGAVSY    60
ARQLQGRVSM TRQLSQDPDD PDWGVAYMEF SGLTPADTAE YFCVRRGSCD YCGDFPWQYW   120
GQGTVVVVSS                                                          130

SEQ ID NO: 33            moltype = AA   length = 104
FEATURE                  Location/Qualifiers
source                   1..104
                         mol_type = protein
                         organism = Homo sapiens
SEQUENCE: 33
DIQMTQSPSS LSASVGDKVT ITCQTSAGYL NWYQQRRGRA PKLLMYDGSR LVTGVPSRFS    60
GRRWGTQYNL TIGSLQPEDI ATYYCQVYEF FGPGTRLDLK STVA                    104

SEQ ID NO: 34            moltype = AA   length = 119
FEATURE                  Location/Qualifiers
source                   1..119
                         mol_type = protein
                         organism = Homo sapiens
SEQUENCE: 34
QVQLVQSGTA VKRPGASVRV SCQASGYTFT DYFIYWWRQA PGQGLEWLGW INPLTSQPSY    60
PSRFQGRLTL TRDTFDEMLY MDLRGLRSDD TGIYFCARRH SDYCDFDIWG SGTQIIVSS    119

SEQ ID NO: 35            moltype = AA   length = 103
FEATURE                  Location/Qualifiers
source                   1..103
                         mol_type = protein
                         organism = Homo sapiens
SEQUENCE: 35
DIQMTQSPSS LSARVGDTVT ITCQANGYLN WYQQRRGKAP KLLIYDGSKL ERGVPSRFSG    60
```

```
RRWGQEYNLT INNLQPEDIA TYFCQVYEFA VPGTRLDLKR TVA                    103

SEQ ID NO: 36           moltype = AA  length = 123
FEATURE                 Location/Qualifiers
source                  1..123
                        mol_type = protein
                        organism = Homo sapiens
SEQUENCE: 36
QVQLLQSGAV VTKPGASVRV SCEASGYKIR DYFIHWWRQA PGQGLQWVGW INPQTGQPNI   60
PRPFQGRVTL TRHASWDFDT FSFYMDLKAL RSDDTAIYFC ARRRSDYCDF DVWGSGTHVT  120
VSS                                                                123

SEQ ID NO: 37           moltype = AA  length = 107
FEATURE                 Location/Qualifiers
source                  1..107
                        mol_type = protein
                        organism = Homo sapiens
SEQUENCE: 37
DIQMTQSPSS LSASIGDRVN ITCQASRDTG SALNWYQQKV GRPPRLLISA VSNLGAGVPS   60
RFSGRRSGTQ STLTINTLQP EDIATYFCQH YEFFGPGTKV DIKRTVA                107

SEQ ID NO: 38           moltype = AA  length = 125
FEATURE                 Location/Qualifiers
source                  1..125
                        mol_type = protein
                        organism = Homo sapiens
SEQUENCE: 38
EVQLVQSGSD VRKPGATVTV SCKADEDEDD FTAYNYFMHW VRQAPGHGLE WIGWINPRTG   60
QPNHAKQFQG RVTLTRERST STVFMKLTNL RLDDTAVYFC ARPLRGGDTW HYHSWGRGTS  120
LTVSS                                                              125

SEQ ID NO: 39           moltype = AA  length = 104
FEATURE                 Location/Qualifiers
source                  1..104
                        mol_type = protein
                        organism = Homo sapiens
SEQUENCE: 39
DIQMTQSPSS LSASVGDKVT ITCQTSAGYL NWYQQRRGRA PKLLMYDGSR LVTGVPSRFS   60
GRRWGTQYNL TIGSLQPEDV ATYYCQVYEF FGPGTRLDLK RTVA                   104

SEQ ID NO: 40           moltype = AA  length = 119
FEATURE                 Location/Qualifiers
source                  1..119
                        mol_type = protein
                        organism = Homo sapiens
SEQUENCE: 40
QVQLVQSGTA VKRPGASVRV SCQASGYTFI DHFIYWWRQA PGQGLEWLGW INPLTSQPSY   60
PSRFQGRLTL TRDTFDEMLY MDLRGLRSDD TGIYFCARRH SDYCDFDIWG SGTQIIVSS   119

SEQ ID NO: 41           moltype = AA  length = 122
FEATURE                 Location/Qualifiers
source                  1..122
                        mol_type = protein
                        organism = Homo sapiens
SEQUENCE: 41
DIQMTQSPSS LSASVGDRVT INCQAGQGIG SSLNWYQKKP GRAPKLLVHG ASNLQRGVPS   60
RFSGSGFHTT FTLTISSLQP DDVATYFCAV FQWFGPGTKV DIKRTVAAPS VFIFPPSDEQ  120
LK                                                                 122

SEQ ID NO: 42           moltype = AA  length = 127
FEATURE                 Location/Qualifiers
source                  1..127
                        mol_type = protein
                        organism = Homo sapiens
SEQUENCE: 42
SQHLVQSGTQ VKKPGASVRV SCQASGYTFT NYILHWWRQA PGQGLEWMGL IKPVFGAVNY   60
ARQFQGRIQL TRDIYREIAF LDLSGLRSDD TAVYYCARDE SGDDLKWHLH PWGQGTQVIV  120
SPASTKG                                                            127

SEQ ID NO: 43           moltype = AA  length = 101
FEATURE                 Location/Qualifiers
source                  1..101
                        mol_type = protein
                        organism = Homo sapiens
SEQUENCE: 43
EIVLTQSPGT LSLSPGETAS LSCTAASYGH MTWYQKKPGQ PPKLLIFATS KRASGIPDRF   60
SGSQFGKQYT LTITRMEPED FAGYYCQQVE FFGQGTRLEI R                      101

SEQ ID NO: 44           moltype = AA  length = 125
```

```
FEATURE                 Location/Qualifiers
source                  1..125
                        mol_type = protein
                        organism = Homo sapiens
SEQUENCE: 44
QVQLVQSGSG VKKPGASVRV SCWTSEDIFE RTELIHWVRQ APGQGLEWIG WVKTVTGAVN    60
FGSPNFRHRV SLTRDRDLFT AHMDIRGLTQ GDTATYFCAR QKFERGGQGW YFDLWGRGTL   120
IVVSS                                                              125

SEQ ID NO: 45           moltype = AA   length = 128
FEATURE                 Location/Qualifiers
source                  1..128
                        mol_type = protein
                        organism = Homo sapiens
SEQUENCE: 45
QVQLVQSGGG VKKPGTSASF SCRTSDDIYD NEFFDSAFMH WVRLIPGQRP EWMGWMNPRS    60
GAVNYARQLQ PRVSMYRDRD LSTAYMEFKS LTSADTGTYF CARKKRGDGF NLYFDLWGRG   120
SQVIVSSA                                                           128

SEQ ID NO: 46           moltype = AA   length = 126
FEATURE                 Location/Qualifiers
source                  1..126
                        mol_type = protein
                        organism = Homo sapiens
SEQUENCE: 46
QVQLVQSGSA MKKPGASVRV SCWTSEDIFD TTELIHWVRQ APGQGLEWIG WVKAVSGAVN    60
YGSLDFRHRV SLTRDRDLST AHMDIRGLTQ DDTATYFCAR QKFARGDQGW FFDLWGRGTL   120
IVVSSA                                                             126

SEQ ID NO: 47           moltype = AA   length = 115
FEATURE                 Location/Qualifiers
source                  1..115
                        mol_type = protein
                        organism = Homo sapiens
SEQUENCE: 47
QVQLVQSGAE VKKPGASVKV SCKASGYTFT GYYMHWVRQA PGQGLEWMGW INPNSGGTNY    60
AQKFQGRVTM TRDTISSTAY MELSRLRSDD TAVYYCARYW YFDLWGRGTL VTVSS        115

SEQ ID NO: 48           moltype = AA   length = 119
FEATURE                 Location/Qualifiers
source                  1..119
                        mol_type = protein
                        organism = Homo sapiens
SEQUENCE: 48
QVQLVQSGAA LKKPGASLRI SCLTYGYKFT DHLIYWWRQA PGQGLEWIGW IKPETGQPSY    60
SYRFQGRVSL TRDTFEEIVF MDLRGLRSDD TAIYFCARRH SDYCDFDVWG SGSQVIVSS    119

SEQ ID NO: 49           moltype = AA   length = 119
FEATURE                 Location/Qualifiers
source                  1..119
                        mol_type = protein
                        organism = Homo sapiens
SEQUENCE: 49
QVQLVQSGAA LKKPGASLRI SCQTYGYKFT DHLIYWWRQA PGQGLEWIGW IKPETGQPSY    60
SYRFQGRVSL TRDTFEEIVF MDLRGLRSDD TAIYFCARRH SDYCDFDVWG GGSQVIVSS    119

SEQ ID NO: 50           moltype = AA   length = 119
FEATURE                 Location/Qualifiers
source                  1..119
                        mol_type = protein
                        organism = Homo sapiens
SEQUENCE: 50
QVQLVQSGAA LKKPGASLRI SCQTYGYKFT DHLIYWWRQA PGQGLEWIGW IKPETGQPSY    60
SYRFQGRVSL TRDTFEEIVF MDLRGLRSDD TAIYFCARRH SDYCDFDVWG SGSQVLVSS    119

SEQ ID NO: 51           moltype = AA   length = 119
FEATURE                 Location/Qualifiers
source                  1..119
                        mol_type = protein
                        organism = Homo sapiens
SEQUENCE: 51
QVQLVQSGAA LKKPGASLRI SCQTYGYKFT DHLIYWWRQA PGQGLEWMGW IKPETGQPSY    60
SYRFQGRVSL TRDTFEEIVF MDLRGLRSDD TAIYFCARRH SDYCDFDVWG SGSQVIVSS    119

SEQ ID NO: 52           moltype = AA   length = 119
FEATURE                 Location/Qualifiers
source                  1..119
                        mol_type = protein
                        organism = Homo sapiens
```

```
SEQUENCE: 52
QVQLVQSGAA LKKPGASLRI SCQTYGYKFT DHLIYWWRQA PGQGLEWIGW IKPETGQPSY    60
SYRFQGRVSL TRDTFEEIAF MDLRGLRSDD TAIYFCARRH TDYCVFDVWG SGSQIIVSS    119

SEQ ID NO: 53            moltype = AA   length = 119
FEATURE                  Location/Qualifiers
source                   1..119
                         mol_type = protein
                         organism = Homo sapiens
SEQUENCE: 53
QVQLVQSGAA LKKPGASVRI SCQAYGYKFT DHLIYWWRQA PGQGLEWIGW IKPETGQPSY    60
SYKFQGRVTL TRDTFEEIHF MDLRGLRYDD TATYFCARRH SDYCDFDVWG SGSQVSVSS    119

SEQ ID NO: 54            moltype = AA   length = 119
FEATURE                  Location/Qualifiers
source                   1..119
                         mol_type = protein
                         organism = Homo sapiens
SEQUENCE: 54
QVQLVQSGAA LKKPGASVRI SCQAYGYKFT DHLIYWWRQA PGQGLEWIGW IKPETGQPSY    60
AYKFQGRVTL TRDTFEEIHF MDLRGVRNDD TATYFCARRH SDYCDFDVWG SGSQVIVSS    119

SEQ ID NO: 55            moltype = AA   length = 119
FEATURE                  Location/Qualifiers
source                   1..119
                         mol_type = protein
                         organism = Homo sapiens
SEQUENCE: 55
QVQLVQSGAA LKKPGASVRI SCQAYGYKFT DYLIHWWRQA PGQGLEWIGW IKPETGQPSY    60
SYKFQGRVTL TRDTFEEILF MDLRGLRSDD TAIYFCARRH SDYCDFDVWG SGSQVIVSS    119

SEQ ID NO: 56            moltype = AA   length = 127
FEATURE                  Location/Qualifiers
source                   1..127
                         mol_type = protein
                         organism = Homo sapiens
SEQUENCE: 56
QPQLVQSGSG AEVKKPGASV RISCEASEYN VFDHFMQWVR QAPGQGLEWM GWINPRGGYP    60
SYSPRFQGRL TFTRQPSWDD SSVTFHMELR GLRHDDTAVY YCARPHSPDD AWSLDVWGRG    120
TLVTVSS                                                             127

SEQ ID NO: 57            moltype = AA   length = 123
FEATURE                  Location/Qualifiers
source                   1..123
                         mol_type = protein
                         organism = Homo sapiens
SEQUENCE: 57
QVQLVQSGAD VKKPGASVTV SCKTDEDEDD FRAHLVQWMR QAPGQRLEWV GWIKPQTGQP    60
SYAQKFQGRV TLTREVSTST VFLQLRNLRS DDTAVYYCAR PRGGRDNWSF HVWGRGTLVT    120
VSS                                                                 123

SEQ ID NO: 58            moltype = AA   length = 119
FEATURE                  Location/Qualifiers
source                   1..119
                         mol_type = protein
                         organism = Homo sapiens
SEQUENCE: 58
QVQLVQSGTA VKKPGASVRV SCQASGYTFT DYFIYWWRQA PGQGLEWLGW INPRTSQPSY    60
PYRFQGRVTL TRDIFEEMLY MDLRGLRSDD TGIYFCARRH SDYCDFDIWG SGTQIIVSS    119

SEQ ID NO: 59            moltype = AA   length = 127
FEATURE                  Location/Qualifiers
source                   1..127
                         mol_type = protein
                         organism = Homo sapiens
SEQUENCE: 59
QVQLVPSGSG VKKPGASVRV SCWTSEDIFE RTELIHWVRQ APGQGLEWIG WVKTVTGAVN    60
FGSLDFRHRI SLTRDRDLFT AHMDIRGLTQ GDTATYFCAR QKFESRYTGG QGWYFDLWGR    120
GTHIVVS                                                             127

SEQ ID NO: 60            moltype = AA   length = 94
FEATURE                  Location/Qualifiers
source                   1..94
                         mol_type = protein
                         organism = Homo sapiens
SEQUENCE: 60
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNW                               94
```

```
SEQ ID NO: 61            moltype = AA   length = 95
FEATURE                  Location/Qualifiers
source                   1..95
                         mol_type = protein
                         organism = Homo sapiens
SEQUENCE: 61
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSS                               95

SEQ ID NO: 62            moltype = AA   length = 94
FEATURE                  Location/Qualifiers
source                   1..94
                         mol_type = protein
                         organism = Homo sapiens
SEQUENCE: 62
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ YDNL                                94

SEQ ID NO: 63            moltype = AA   length = 104
FEATURE                  Location/Qualifiers
source                   1..104
                         mol_type = protein
                         organism = Homo sapiens
SEQUENCE: 63
DIQMTQSPSS LSASVGDTVT ITCQTNKGYL NWYQQRRGRA PKLLMYDGSK LVTGVPSRLS    60
GRRWGTQYNL TIGSLQPEDI ATYYCQVYEF FGPGTRLDLK RTVA                     104

SEQ ID NO: 64            moltype = AA   length = 104
FEATURE                  Location/Qualifiers
source                   1..104
                         mol_type = protein
                         organism = Homo sapiens
SEQUENCE: 64
DIQMTQSPSS LSASVGDTVT ITCQTNKGYL NWYQQKRGRA PKLLMYDGSK LVTGVPSRLS    60
GRRWGTQYNL TIGSLQPEDI ATYYCQVYEF FGPGTRLDLK RTVA                     104

SEQ ID NO: 65            moltype = AA   length = 104
FEATURE                  Location/Qualifiers
source                   1..104
                         mol_type = protein
                         organism = Homo sapiens
SEQUENCE: 65
DIQMTQSPSS LSASVGDTVT ITCQTNKGYL NWYQQRRGRA PKLLMYDGSK LVTGVPSRLS    60
GRRWGTQYNL TIGSLQPEDI ATYYCQVYEF FGPGTRLDLK RTVA                     104

SEQ ID NO: 66            moltype = AA   length = 104
FEATURE                  Location/Qualifiers
source                   1..104
                         mol_type = protein
                         organism = Homo sapiens
SEQUENCE: 66
DIQMTQSPSS LSASVGDTVT ITCQTNKGYL NWYQQRRGRA PKLLMYDGSK LVTGVPSRLS    60
GRRWGTQYNL TIGSLQPEDI ATYYCQVYEF FGPGTRLDLK RTVA                     104

SEQ ID NO: 67            moltype = AA   length = 104
FEATURE                  Location/Qualifiers
source                   1..104
                         mol_type = protein
                         organism = Homo sapiens
SEQUENCE: 67
DIQMTQSPSS LSASVGDTVT ITCQTNKGYL NWYQQRRGRA PKLLMYDGSK LVTGVPSRLS    60
GRRWGTQYNL TIGSLQPEDI ATYYCQVYEF FGPGTRLDLK RTVA                     104

SEQ ID NO: 68            moltype = AA   length = 104
FEATURE                  Location/Qualifiers
source                   1..104
                         mol_type = protein
                         organism = Homo sapiens
SEQUENCE: 68
DIQMTQSPSS LSASVGDTVT ITCHTNKGYL NWYQQRRGRA PKLLMFDGSK LVTGVPSRFS    60
GRRWGTQYNL TIGSLQPEDI ATYYCQVYEV FGPGTRLDLK RTVA                     104

SEQ ID NO: 69            moltype = AA   length = 104
FEATURE                  Location/Qualifiers
source                   1..104
                         mol_type = protein
                         organism = Homo sapiens
SEQUENCE: 69
DIQMTQSPSS LSASVGDTVT ITCHTNKGYL NWYQQRRGRA PKLLMFDGSK LVTGVPSRFS    60
```

```
GRRWGTQYNL TIGSLQPEDI ATYYCQVYEV FGPGTRLDLK RTVA                     104

SEQ ID NO: 70           moltype = AA   length = 104
FEATURE                 Location/Qualifiers
source                  1..104
                        mol_type = protein
                        organism = Homo sapiens
SEQUENCE: 70
DIQMTQSPSS LSASVGDTVT ITCQTTKGYL NWYQQRRGRA PKLLMFDGSK LVTGVPSRFS     60
GRRWGTQYNL TIGSLQPEDL ATYYCQVYEF FGPGTRLDLK RTVA                    104

SEQ ID NO: 71           moltype = AA   length = 107
FEATURE                 Location/Qualifiers
source                  1..107
                        mol_type = protein
                        organism = Homo sapiens
SEQUENCE: 71
DIQMTQSPSS LSASVGDRVT ITCQASQGIS NSLNWYQQKP GKAPRLLIYG TSTLQRGVPS     60
RFSGSGSGTR FTVTINSLQP EDIATYFCQH NEFFGRGTKV DIKRTVA                 107

SEQ ID NO: 72           moltype = AA   length = 108
FEATURE                 Location/Qualifiers
source                  1..108
                        mol_type = protein
                        organism = Homo sapiens
SEQUENCE: 72
DIQMTQSPSS VSASVGDRVT ITCQASRDTD NSLTWYQQKP GRPPKLLIYH VVNLGPGVPS     60
RFSGSASSAT QSTLIISDFQ PDDVATYFCQ NYEFFGPGTK VEIKRTVA                108

SEQ ID NO: 73           moltype = AA   length = 103
FEATURE                 Location/Qualifiers
source                  1..103
                        mol_type = protein
                        organism = Homo sapiens
SEQUENCE: 73
DIQMTQSPSS LSARVGDKVT ITYQTSAGYL NWYQQRRGRA PKLLMYDGSR LVTGAPSRFS     60
GRRWGTQYNL TIGSLQPEDI ATYYCQVYEF FGPGTRLDLK RTV                     103

SEQ ID NO: 74           moltype = AA   length = 26
FEATURE                 Location/Qualifiers
REGION                  1..26
                        note = CDRH3
source                  1..26
                        mol_type = protein
                        organism = synthetic construct
SEQUENCE: 74
FCTRGKYCTA RDYYNWDFEH WGRGAP                                         26

SEQ ID NO: 75           moltype = AA   length = 26
FEATURE                 Location/Qualifiers
REGION                  1..26
                        note = CDRH3
source                  1..26
                        mol_type = protein
                        organism = synthetic construct
SEQUENCE: 75
FCTRGKYCTA RDAYNWDFEH WGRGAP                                         26

SEQ ID NO: 76           moltype = AA   length = 22
FEATURE                 Location/Qualifiers
REGION                  1..22
                        note = CDRH3
source                  1..22
                        mol_type = protein
                        organism = synthetic construct
SEQUENCE: 76
FCTRGKYCTY NWDFEHWGRG AP                                             22

SEQ ID NO: 77           moltype = AA   length = 50
FEATURE                 Location/Qualifiers
REGION                  1..50
                        note = gp 120 residue
source                  1..50
                        mol_type = protein
                        organism = synthetic construct
SEQUENCE: 77
QLLLNGSLAE EEIIIKSENL TDNIKTIIVQ LNQSIGINCT RPNNNTRKSV                50

SEQ ID NO: 78           moltype = AA   length = 50
```

```
FEATURE                 Location/Qualifiers
REGION                  1..50
                        note = gp 120 residue
source                  1..50
                        mol_type = protein
                        organism = synthetic construct
SEQUENCE: 78
QLLLNGSLAE EEIIIRSENL TDNTKTIIVH LNESVEIECV RPNNNTRKSV            50

SEQ ID NO: 79           moltype = AA  length = 50
FEATURE                 Location/Qualifiers
REGION                  1..50
                        note = gp120 residue
source                  1..50
                        mol_type = protein
                        organism = synthetic construct
SEQUENCE: 79
QLLLNGSLAE KEIMIRSENL TNNAKTIIVQ LTEAVNITCM RPGNNTRRSV            50

SEQ ID NO: 80           moltype = AA  length = 50
FEATURE                 Location/Qualifiers
REGION                  1..50
                        note = gp120 residue
source                  1..50
                        mol_type = protein
                        organism = synthetic construct
SEQUENCE: 80
QLLLNGSLAE KEIIRSENI TDNVKIIIVH LNESVEINCT RPNNNTRKSI             50

SEQ ID NO: 81           moltype = AA  length = 50
FEATURE                 Location/Qualifiers
REGION                  1..50
                        note = gp120 residue
source                  1..50
                        mol_type = protein
                        organism = synthetic construct
SEQUENCE: 81
QLLLNGSTAE EDIIIRSENL TNNAKTIIVH LNESIEIECT RPGNNTRKSI            50

SEQ ID NO: 82           moltype = AA  length = 50
FEATURE                 Location/Qualifiers
REGION                  1..50
                        note = gp120 residue
source                  1..50
                        mol_type = protein
                        organism = synthetic construct
SEQUENCE: 82
QLLLNGSLAE EEIVIRSENL TDNAKTIIVH LNKSVEIECI RPGNNTRKSI            50

SEQ ID NO: 83           moltype = AA  length = 50
FEATURE                 Location/Qualifiers
REGION                  1..50
                        note = gp120 residue
source                  1..50
                        mol_type = protein
                        organism = synthetic construct
SEQUENCE: 83
QLLLNGSLSE EGIIIRSKNL TDNTKTIIVH LNESVAIVCT RPNNNTRKSI            50

SEQ ID NO: 84           moltype = AA  length = 7
FEATURE                 Location/Qualifiers
REGION                  1..7
                        note = CDRH1
SITE                    5
                        note = MISC_FEATURE - xaa = ile or leu
SITE                    6
                        note = MISC_FEATURE - xaa = asn or asp
source                  1..7
                        mol_type = protein
                        organism = synthetic construct
SEQUENCE: 84
GYEFXXC                                                            7

SEQ ID NO: 85           moltype = AA  length = 6
FEATURE                 Location/Qualifiers
REGION                  1..6
                        note = CDRH2
source                  1..6
                        mol_type = protein
```

```
                        organism = synthetic construct
SEQUENCE: 85
KPRGGA                                                                          6

SEQ ID NO: 86           moltype = AA  length = 12
FEATURE                 Location/Qualifiers
REGION                  1..12
                        note = CDRH3
SITE                    3
                        note = MISC_FEATURE - XAA= ASN OR TYR
SITE                    5
                        note = MISC_FEATURE - XAA= ASP OR THR
source                  1..12
                        mol_type = protein
                        organism = synthetic construct
SEQUENCE: 86
GKXCXYNWDF EH                                                                  12

SEQ ID NO: 87           moltype = AA  length = 16
FEATURE                 Location/Qualifiers
REGION                  1..16
                        note = CDRH3
SITE                    3
                        note = MISC_FEATURE - XAA = ASN OR TYR
SITE                    5
                        note = MISC_FEATURE - XAA = ASP OR THR
source                  1..16
                        mol_type = protein
                        organism = synthetic construct
SEQUENCE: 87
GKXCXARDYY NWDFEH                                                              16

SEQ ID NO: 88           moltype = AA  length = 9
FEATURE                 Location/Qualifiers
REGION                  1..9
                        note = CDRL1
SITE                    5
                        note = MISC_FEATURE - XAA = SER or TYR
source                  1..9
                        mol_type = protein
                        organism = synthetic construct
SEQUENCE: 88
RTSQXGSLA                                                                       9

SEQ ID NO: 89           moltype = AA  length = 7
FEATURE                 Location/Qualifiers
REGION                  1..7
                        note = CDRL2
source                  1..7
                        mol_type = protein
                        organism = synthetic construct
SEQUENCE: 89
SGSTRAA                                                                         7

SEQ ID NO: 90           moltype = AA  length = 5
FEATURE                 Location/Qualifiers
REGION                  1..5
                        note = CDRL3
source                  1..5
                        mol_type = protein
                        organism = synthetic construct
SEQUENCE: 90
QQYEF                                                                           5
```

What is claimed is:

1. A method of increasing potency and breadth of an isolated anti-CD4 binding site (anti-CD4bs) VRC01-related antibody variant composition having a heavy chain variable region and a light chain variable region, comprising substituting a target amino acid at position 54 of the heavy chain variable region according to Kabat numbering with a hydrophobic amino acid, wherein the heavy chain variable region and the light chain variable region comprise an amino acid sequence pair set forth in: SEQ ID NOs: 2 and 1; SEQ ID NOs: 4 and 3; SEQ ID NOs: 6 and 5; SEQ ID NOs: 8 and 7; SEQ ID NOs: 10 and 9; SEQ ID NOs: 12 and 11; SEQ ID NOs: 14 and 13; SEQ ID NOs: 16 and 15; SEQ ID NOs: 18 and 17; SEQ ID NOs: 20 and 19; SEQ ID NOs: 22 and 21; SEQ ID NOs: 24 and 23; SEQ ID NOs: 26 and 25; SEQ ID NOs: 28 and 27; SEQ ID NOs: 30 and 29; SEQ ID NOs: 32 and 31; SEQ ID NOs: 34 and 33; SEQ ID NOs: 36 and 35; SEQ ID NOs: 38 and 37;

SEQ ID NOs: 40 and 39; SEQ ID NOs: 42 and 41; SEQ ID NOs: 44 and 43; SEQ ID NOs: 45 and 19; or SEQ ID NOs: 46 and 19.

2. The method of claim 1, wherein the substitute hydrophobic amino acid is selected from the group consisting of alanine, isoleucine, leucine, methionine, phenylalanine, tryptophan, tyrosine, and valine.

3. The method of claim 1, wherein the anti-CD4bs PVL antibody is selected from the group consisting of VRC01, VRC02, NIH-45-46, 3BNC117, 3BNC62, 3BNC95, 3BNC176, 12A21, VRC-PG04, VRC-CH30, VRC-CH31, VRC-CH32, VRC-CH33, VRC-CH34, VRC03 heavy chain with VRC01 light chain, gVRC-H5(d74) heavy chain with VRC-PG04 light chain, gVRC-H12(d74) heavy chain with VRC-PG04 light chain, VRC03, VRC01 heavy chain with VRC03 light chain, 3BNC55, 3BNC91, 3BNC104, 3BNC89, 12A21, and VRC-PG04b.

* * * * *